(12) United States Patent
Gostjeva et al.

(10) Patent No.: US 7,977,092 B2
(45) Date of Patent: Jul. 12, 2011

(54) METHODS FOR IDENTIFYING CANDIDATE ANTI-TUMORIGENIC AGENTS

(75) Inventors: Elena V. Gostjeva, Winchester, MA (US); William G. Thilly, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 415 days.

(21) Appl. No.: 12/284,521

(22) Filed: Sep. 23, 2008

(65) Prior Publication Data
US 2009/0081720 A1    Mar. 26, 2009

Related U.S. Application Data

(62) Division of application No. 11/156,251, filed on Jun. 17, 2005, now Pat. No. 7,427,502.

(60) Provisional application No. 60/580,575, filed on Jun. 17, 2004.

(51) Int. Cl.
*C12N 5/00* (2006.01)
*G01N 1/30* (2006.01)

(52) U.S. Cl. ............... 435/325; 435/40.5; 435/40.52; 435/29; 435/32; 435/4

(58) Field of Classification Search ............ None
See application file for complete search history.

(56) References Cited

U.S. PATENT DOCUMENTS

| | | |
|---|---|---|
| 7,427,502 B2 | 9/2008 | Thilly et al. |
| 7,850,961 B2 | 12/2010 | Clarke et al. |
| 2006/0083682 A1 | 4/2006 | Bergstein |
| 2009/0098562 A1 | 4/2009 | Gostjeva et al. |
| 2009/0304662 A1 | 12/2009 | Thilly et al. |
| 2010/0075366 A1 | 3/2010 | Gostjeva et al. |
| 2010/0284905 A1 | 11/2010 | Gostjeva et al. |

FOREIGN PATENT DOCUMENTS

| | | |
|---|---|---|
| WO | WO 2006/009860 | 1/2006 |
| WO | WO 2007/067795 A2 | 6/2007 |
| WO | WO 2008/115517 A2 | 9/2008 |
| WO | WO 2008/156629 A2 | 12/2008 |
| WO | WO 2010/036322 A1 | 4/2010 |

OTHER PUBLICATIONS

Muzio, Lo L., et al., "Primary introral leiomyosarcoma of the tongue: an immunohistochemical study and review of the literature," *Oral Oncology*, Elsevier Science, Oxford, GB, 36(6), pp. 519-524, (2000).
Hirokawa, Mitsuyoshi, et al., "Gastrointestinal Stromal Tumor with Skeinoid Fibers of the Ileum," *Diagnostic Cytopathology*, 23(4), pp. 266-268 (2000).
Maly, B., et al. "Fine Needle Aspiration Biopsy of Intraparotid Schwannoma: A case report," *ACTA Cytologica*, 47(6), pp. 1131-1134 (2003).
Liu, Katharine, et al., "Logistic Regression Analysis of High Grade Spindle Cell Neoplasms," *ACTA Cytologica*, 43(4), pp. 593-600 (1999).
Al-Hajj, M. and M.F. Clarke, "Self-Renewal and Solid Tumor Stem Cells," *Oncogene*, 23:7274-7282 (2004).
Chari, R.S., et al., "Preoperative Radiation and Chemotherapy in the Treatment of Adenocarcinoma of the Rectum," *Annals of Surgery*, 221:778-787 (1995).
Ying, Z., et al., "Expression of Neural Stem Cell Surface Marker CD133 in Balloon Cells of Human Focal Cortical Dysplasia," *Epilepsia*, 46(11): 1716-1723 (2005).
Silverman, J.S. and S. Brustein, "Myxoid Dermatofibrohistiocytoma: An Indolent Post-Traumatic Tumor Composed of CD34+ Epitheliod and Dendtritic Cells and Factor XIIIa+ Dendrophages," *J. Cutan. Pathol.* 23:551-557 (1996).
Scheidl, S.J., et al., "mRNA Expression Profiling of Laser Microbeam Microdissected Cells from Slender Embryonic Structures," *Am. Jour. Path.*, 160:801-813 (2002).
Lodding, P., et al., "Cellular Schwannoma," *Virchows Archiv.*, 416:237-248 (1990).
Drezek, R., et al., "Light Scattering from Cervical Cells Throughout Neoplastic Progression: Influence of Nuclear Morphology, DNA Content, and Chromatin Texture," *J. Biomed. Optics*, 8:7-16 (2003).
Itoi, T., et al., "Detection of Telomerase Activity in Biopsy Specimens for Diagnosis of Biliary Tract Cancers," *Gastrointestinal Endoscopy*, 52:380-386 (2000).
Ruddy, J.M.B., and S.K. Majumdar, "Antitumorigenic Evaluation of Thalidomide Alone and in Combination with Cisplatin in DBA2/J Mice," *Jour. Biomedicine and Biotechnology*, 2:7-13 (2002).
Herrero-Jimenez, P., et al., "Mutation, Cell Kinetics, and Subpopulations at Risk for Colon Cancer in the United States," *Mutat. Res.* 400:553-578 (1998).
Herrero-Jimenez, P., et al., "Population Risk and Physiological Rate Parameters for Colon Cancer. The Union of an Explicit Model for Carcinogenesis with the Public Health Records of the United States," *Mutat. Res.* 447:73-116 (2000).
Fujiu, K. and O. Numata, "Reorganization of Microtubules in the Amitotically Dividing Macromolecules of *Tetrahymena*," *Cell Motility and Cytoskeleton*, 46:17-27 (2000).
Merok J.R., et al., "Cosegregation of Chromosomes Containing Immortal DNA Strands in Cells that Cycle with Asymmetric Stem Cell Kinetics," Cancer Res. 62:6791-5 (2002).
Gostjeva, E.V., et al. "Bell-Shaped Nuclei Dividing by Symmetrical and Asymmetrical Nuclear Fission Have Qualities of Stem Cells in Human Colonic Embryogenesis and Carcinogenesis," *Cancer Gen. and Cytogenetics*, 164:16-24(2006).
Gostjeva, E.V. and W.G. Thilly, "Stem Cell Stages and the Origins of Colon Cancer," *Stem Cell Reviews*, 1:243-252 (2005).

(Continued)

*Primary Examiner* — Rebecca Prouty
*Assistant Examiner* — Paul Martin
(74) *Attorney, Agent, or Firm* — Hamilton, Brook, Smith & Reynolds, P.C.

(57) ABSTRACT

Methods for identifying stem cells and other cells specific to embryogenesis and carcinogenesis, classifying tissue samples, diagnosing precancerous and cancerous or atherosclerotic lesions, testing the value of anticancer agents, discovering macromolecules specifically expressed in particular cell types, using stem cells in restorative tissue therapy as well as methods for preparing tissue samples so heteromorphic nuclear morphotypes remain intact are disclosed.

14 Claims, 38 Drawing Sheets
(38 of 38 Drawing Sheet(s) Filed in Color)

OTHER PUBLICATIONS

Office Action, Israeli Appl. No. 179972 with reply due Feb. 7, 2010.
Office Action, China Application No. 200580027499.4, dated Oct. 21, 2010.
Office Action, Japan Application No. 2007-516787, dated Dec. 14, 2010.
Office Action, U.S. Appl. No. 12/283,727, dated Jan. 27, 2011.
Reply to Office Action, Application No. EP 08768379.3, filed Feb. 11, 2011.
Reply to Restriction Requirement, U.S. Appl. No. 12/085,533, filed Jan. 31, 2011.
Reply to Restriction Requirement, U.S. Appl. No. 12/283,727, filed Mar. 1, 2011.
Office Action, U.S. Appl. No. 12/085,533, dated Mar. 18, 2011.
Notification Concerning Transmittal of International Preliminary Report on Patentability (IPRP), PCT/US2008/007327 with IPRP and Written Opinion, mailed Dec. 30, 2009.
Notification of Transmittal of the International Search Report (ISR) and the Written Opinion (WO) of the International Searching Authority, or The Declaration, PCT/US2009/005241 with ISR and WO, mailed Jan. 2, 2010.
Andersson, G.K.A., et al., "Exposure and Removal of Stainable Groups DuringFeulgen Acid Hydrolysis of Fixed Chromatin at Different Temperatures," *Histochemie* 27:165-172 (1971).
Biesterfeld, S., et al., "DNA Image Cytometry in the Differential Diagnosis of Endometrial Hyperplasia and Adenocarcinoma," *Analyt. Quant. Cytol. Histol.*, 23:123-128 (2001).
Cairns, J., "Mutation Selection and the Natural History of Cancer," *Nature* 255:197-200 (May 1975).
Fischer, P.M., "Recent Progress in the Discovery and Development of Cyclin-Dependent Kinase Inhibitors," *Expert Opinion on Investigational Drugs* 14(4): abstract only (Apr. 2005).
Folkman, J. and Ingber, D., "Inhibition of Angiogenesis," *Cancer Biology* 3:88-96 (1992).
Gibson, P.R., et al., "Isolation of Colonic Crypts That Maintain Structural and Metabolic Viability in Vitro," *Gastroenterology* 96:283-291 (1989).
Gómez-Vidal. J.A., et al, "Actual Targets in Cytodifferentiation Cancer Therapy," *Current Topics in Medicinal Chemistry* 4:175-202 (2004).
Gostjeva, E. V., et al., "Nuclear Morphotypes in Human Embryogenesis and Carcinogenesis: Bell-Shaped Nuclei Show Stem-like Properties in Vivo," *Environmental and Molecular Mutagenesis* 47(6), p. 405 (2006) (Abstract Only).
Gosteva, E.F., "Densitometric Scanning of Plant Chromosomes Aimed at Their Identification," *Cytology and Genetics* 32(5):13-16 (1998).
Hardie, D.C., et al., "From Pixels to Picograms: A Beginners' Guide to Genome Quantification by Feulgen Image Analysis Densitometry," *J. Histochemistry & Cytochemistry* 50(6):735-749 (2002).
Kjellstrand, P., "Mechansism of the Feulgen Acid Hydrolysis," *J. Microscopy* 119(3):391-396 (1980).
Otto, W.R., "Lung Epithelial Stem Cells," *J. Pathology* 197:527-535 (May 2002).
Potten, C.S., et al., "Intestinal Stem Cells Protect Their Genome by Selective Segregation of Template DNA Strands," *J. Cell Science* 115:2381-2388 (2002).
Sell, S., "Stem Cell Origin of Cancer and Differentiation Therapy," *Critical Reviews in Oncology/Hematology* 51:1-28 (2004).
Sperr, W.R., et al., "Human Leukaemic Stem Cells: A Novel Target of Therapy," *European J. Clinical Investigation* 34(Suppl. 2):31-40 (2004).
Venezia, T.A., et al., "Molecular Signatures of Proliferation and Quiescence in Hematopoietic Stem Cells," *PLoS Biology* 2(10):1640-1651 (Oct. 2004).

Wadkins, R.M. et al., "Actinomycin D Binds to Metastable Hairpins in Single-Stranded DNA," *Biochemistry* 37(34): 11915-11923 (Aug. 1998).
White, R.J., et al., "Development of Mitoxantrone," *Investigational New Drugs* 3(2):85-93 (1985).
Mar. 24, 2006, Invitation to Pay Additional Fees with Partial International Search Report, PCT/US2005/021504.
May 5, 2006, Notification of Transmittal of International Search Report (ISR) and Written Opinion (WO), with ISR and WO, PCT/US2005/021504.
Jan. 4, 2007, Notification Concerning Transmittal of International Preliminary Report on Patentability (IPER), with IPER and Written Opinion, PCT/US2005/021504.
Jun. 27, 2007, Notification of Transmittal of the International Search Report (ISR) and the Written Opinion (WO) of the International Searching Authority, or the Declaration, with ISR and WO, PCT/US2006/047136.
Jun. 19, 2008, Notification Concerning Transmittal of International Preliminary Report on Patentability (IPER), with IPER and Written Opinion, PCT/US2006/047136.
Aug. 12, 2008, Invitation to Pay Additional Fees and, Where Applicable, Protest Fee with Partial International Search Report, PCT/US2008/003604.
Jan. 19, 2009, Notification of Transmittal of the International Search Report (ISR) and the Written Opinion (WO) of the International Searching Authority, or the Declaration, with ISR and WO, PCT/US2008/003604.
Dec. 2, 2008, Notification of Transmittal of the International Search Report (ISR) and the Written Opinion (WO) of the International Searching Authority, or the Declaration, with ISR and WO, PCT/US2008/007327.
U.S. Appl. No. 12/085,533, filed Dec. 8, 2006.
U.S. Appl. No. 12/283,727, filed Sep. 15, 2008.
Office Action, U.S. Appl. No. 12/283,727, dated Apr. 7, 2011.
Cutts, S.M., et al. "Defective Chromosome Segregation, Microtubule Bundling and Nuclear Bridging in Inner Centromere Protein Gene (Incenp)- Disrupted Mice", *Human Molecular Genetics* 8(7):1145-1155 (1999).
Klijanienko, J., et al., "Fine-Needle Aspiration of Leiomyosarcoma: A Correlative Cytohistopathological Study of 96 Tumors in 68 Patients", *Diagn. Cytopathol.* 28:119-125 (2003).
Özkinay, C. and Mitelman, F., "A Simple Trypsin-Giemsa Technique Producing Simultaneous G- and C-Banding in Human Chromosomes", *Hereditas* 90:1-4 (1979).
Notification Concerning Transmittal of International Preliminary Report on Patentability (IPRP) with IPRP, PCT/US2009/005241, mailed Apr. 7, 2011.
Sakaki, M., et al., "Gallbladder Adenocarcinoma with Florid Neuroendocrine Cell Nests and Extensive Paneth Cell Metaplasia," *Endocrine Pathology* 11(4):365-371 (2000).
Boman, B.M., et al., "Cancer Stem Cells: A Step Toward the Cure," *J. Clinical Oncology* 26(17):2795-2799 (2008).
Notification Concerning Transmittal of International Preliminary Report on Patentability (IPRP) with IPRP, PCT/US2008/003604, issued Sep. 22, 2009.
Office Action, EP 05761437.2, dated Mar. 26, 2010.
Reply filed Mar. 3, 2010, Israel Appl. No. 179972.
Office Action dated Jun. 11, 2010, Australia 2006321710.
Office Action rec'd Mar. 31, 2010, India 3481/CHENP/2008.
Office Action, EP 08768379.3, dated Aug. 2, 2010.
Office Action, Israel 191746, dated Jul. 14, 2010.
James, H.A., "The Potential Application of Ribozymes for the Treatment of Hematological Disorders," *J. Leukocyte Biology* 66:361-368 (1999).
Office Action, Israel 179972, dated Jul. 6, 2010.
Office Action, China 200680052588, dated Sep. 14, 2010.
Restriction Requirement, U.S. Appl. No. 12/085,533, date of mailing Sep. 1, 2010.

FIG. 1

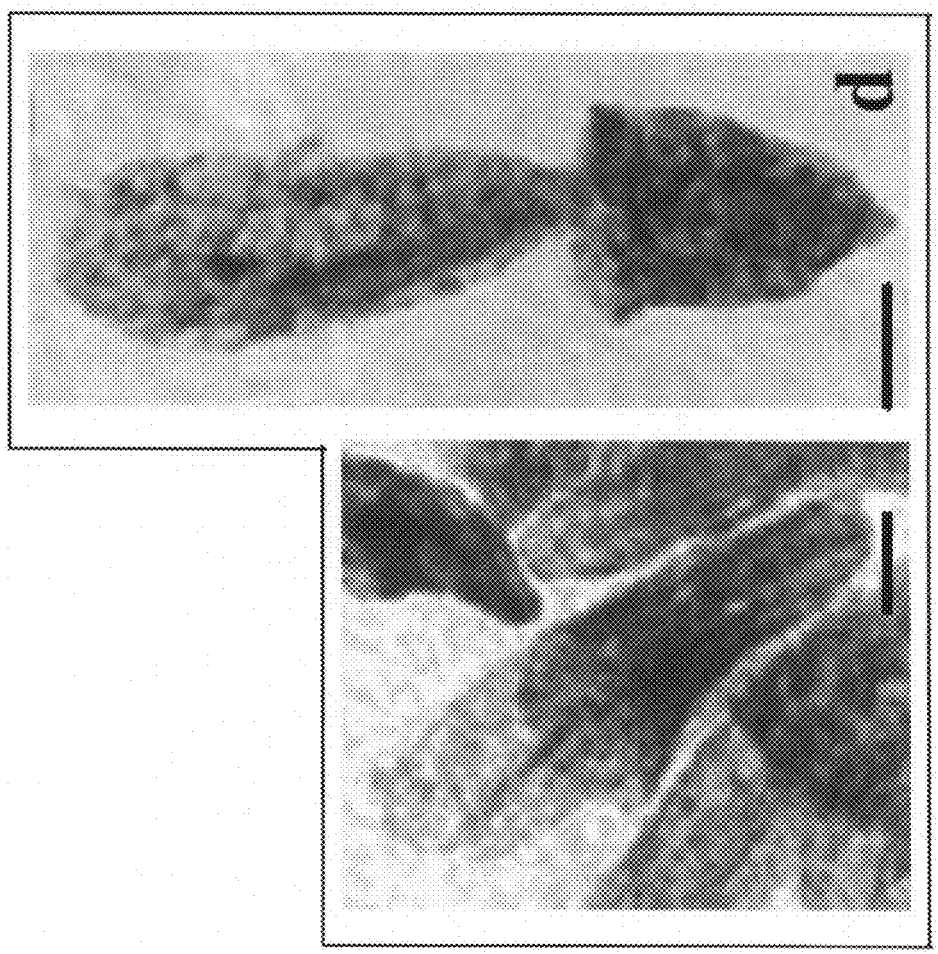

METHODS FOR IDENTIFYING CANDIDATE ANTI-TUMORIGENIC AGENTS

RELATED APPLICATIONS

This application is a divisional of U.S. Application No. 11/156,251, filed Jun. 17, 2005 now U.S. Pat. No. 7,427,502, which claims the benefit of U.S. Provisional Application No. 60/580,575, filed Jun. 17, 2004. The entire teachings of the above applications are incorporated herein by reference

BACKGROUND OF THE INVENTION

The processes that lead to growth and differentiation in animal embryos, fetuses, neonates and juveniles share certain characteristics with the processes that lead to growth and differentiation of cell types preceding and creating tumors. Methods that recognize antigenic molecules in tumors and fetuses have shown that there are many molecules observable in both fetuses and tumors that are not observed in adult organs. In the nineteenth century it was argued that tumors might arise from residual embryonic cells in adults. Current views point to the existence of self-renewing stem cells in which genetic changes occur in lineal descent from embryonic through adult stem cells that create tumor stem cells that give rise to tumors. The summarized argument is that a single normal tissue stem cell could be the progenitor of preneoplastic lesions that in turn give rise to a founding stem cell for tumors that in turn give rise to a founding stem cell for clonal metastases and transplanted tumors. Based on the clear presence of histologically differentiable cell types in preneoplastic lesions, tumors and metastases, and by analogy to embryological growth and development, it can be inferred that the originating stem cell of tissues, preneoplastic lesions, tumors and metastases must be capable of differentiation as well as self-renewing growth. If the stem cell theory of tumor growth is correct, then there is a tremendous need to identify, sort, classify and manipulate tumor stem cells. However, identification or isolation of such cells has not been described in the art.

SUMMARY OF THE INVENTION

The present invention derives from the process of identification of and method for classifying organ-specific and/or tumor stem cells and other specific cell forms in a cell culture, tissue, pre-neoplastic lesion or tumor sample. The invention relates to the process of determining the nuclear morphotypes, the modes of nuclear division and the involvement of nuclei of particular morphotype in multicellular aggregates and multinuclear syncytia among all cells in a cell culture, tissue, preoplastic lesion or tumor sample and identification of organ-specific or tumor stem cells on the basis of a particular nuclear morphotype alone. Multiple forms (nuclear morphotypes) of clear and reproducible non-spherical nuclei in fetal tissue, preneoplastic lesions (adenomas of the colon) and neoplastic lesions or tumors (adenocarcinomas of the colon, carcinomas of the pancreas) were observed that were absent in normal adult tissue such as colonic crypts or liver parenchyma. These morphotypes, disclosed herein, included nuclei of size and shapes previously unreported in the annals of histology or pathology of human tissues.

The nuclear forms or morphotypes in fetal and neoplastic tissues included the spherical and ovoid nuclear forms commonly seen in adult tissues but also presented a diverse set of reproducible morphotypes that ranged in size from the 40 micron "sausage-shaped", through shorter (~8-20 micron) "cigar-shaped", "bullet-shaped" and "kidney shaped" to "condensed spherical" nuclei of some 4 microns diameter. One remarkable, previously unreported, nuclear morphotype had the form of cups or bells with an open "mouth" designated "bell-shaped". These bell-shaped nuclei were observed in symmetric nuclear divisions resembling the separation of two stacked paper cups.

These "cup-from-cup" divisions were also remarkable in that they were amitotic, e.g., did not involve condensation of all human chromosomes and separation as in mitosis. They were symmetrical nuclear divisions insofar as two apparently identical bell-shaped nuclei resulted from the cup-from-cup division. These bell-shaped nuclei were also observed to undergo amitotic asymmetric nuclear divisions in which a bell-shaped nucleus appeared to give rise to an enclosed nucleus of one of the other nuclear morphotypes. This production of the original bell-shaped nucleus and a nucleus of a different morphotype is the first known visualization of an asymmetrical nuclear division. The appearance of a heteromorphic nuclear morphotype distinct from the bell-shaped nucleus in asymmetrical amitotic cell divisions involving bell-shaped nuclei is disclosed herein to distinctly define a cell with a heteromorphic nuclear morphotype distinct from the phenotype of a cell with a bell-shaped nucleus.

Asymmetric nuclear division is widely considered as a necessary characteristic of stem cells in normal development. The discovery of nuclear morphotypes common to both fetal tissue, preneoplasia and neoplasia bear on the hypothesis that tumors are a re-expression of embryonic phenotypes, specifically stem cells forming clonal populations with derived differentiated cellular phenotypes. The nuclear morphotype that identifies a stem cell appears as a bell- or cup-shaped nucleus in which stained DNA creates a hollow structure easily differentiated from all other nuclear morphotypes in a fetal tissue or tumor sample in which stained DNA images show a nucleus fully encased by a DNA-containing structure.

Further observations confirmed and extended the discovery that adenocarcinomas and embryos partially share lineages of cells with distinct nuclear morphotypes arising from what appears to be the identical processes of symmetrical and asymmetrical nuclear divisions of bell-shaped nuclei without the appearance of a mitotic apparatus. While the picture of the appearance and disappearance of these nuclear forms from early embryo through fetal and juvenile growth to adult organ and reappearance in carcinogenesis is incomplete, the potential value of these findings in cancer prevention and therapy is of obvious importance offering benefits in diagnosis and treatment of cancers and other diseases such as atherosclerosis that also arise from slowly growing monoclonal colonies. Benefits are expected from growing these bell-shaped nuclei independently for applications such as, for example, restorative therapy for complex tissues and organs.

The value of the process described herein to specifically identify these previously unrecognized cells as stem cells by their nuclear morphotype, modes of nuclear division and/or involvement in multi-nuclear structures in normal and tumor tissues is clear. The claimed processes make it possible to specifically recognize stem cells and other fetal and tumor-specific nuclear morphotypes, permit their isolation and study, and provide for their use in tests to discover which of many plausible preventative or therapeutic regimens for cancer are effective. The methods described herein also provide means to discover specific stem cells for regeneration and transplantation therapies for human tissues and organs (e.g., tissue restoration therapy).

In one embodiment, the invention is directed to a method for characterizing (e.g., classifying) a cell or tissue sample based on nuclear structures associated with stages of development or pathology, comprising: a) visualizing the nuclei of cells distributed throughout the tissue sample, wherein the tissue sample is prepared by a method that substantially preserves the integrity of structures of substantially all nuclei having maximum diameters up to about 50 microns; and b) determining the presence and/or absence of a class or classes of nuclear morphotypes, wherein presence or absence of a particular class is indicative of a stage of development or pathology. In one embodiment, the tissue sample is obtained by surgical excision. In a particular embodiment, the tissue sample is physically (e.g., frozen) or chemically fixed (e.g., treated with one or more chemical fixing agents selected from the group consisting of: alcohols, aldehydes, organic acids and combinations thereof such as, for example, methanol and acetic acid). In a particular embodiment, the tissue sample is fixed prior to cellular degradation of nuclei. In another embodiment, the cells of the tissue sample are partially dissociated by tissue maceration and spreading. In one embodiment, the cells or macromolecules of the tissue sample are stained, thereby allowing visualization of nuclei. In another embodiment, DNA is stained, thereby allowing visualization of nuclei. In another embodiment, the tissue sample is fixed within 30 minutes of surgical removal.

In another embodiment, the tissue sample is obtained from a multicellular animal (e.g., a vertebrate, e.g., a mammal, e.g., primates, rodents, canines, felines, porcines, ovines, bovines and rabbits). In a particular embodiment, the mammal is a human.

In a particular embodiment, the presence or absence of a particular class or classes of nuclear morphotypes is indicative of a particular stage of development (e.g., embryonic, fetal (organogenesis), neonatal, juvenile and adult stages of development). In another embodiment, the presence or absence of a particular class or classes of nuclear morphotypes is indicative of a tissue sample selected from the group consisting of: normal, preneoplastic, neoplastic and metastatic. The class or classes of nuclear morphotypes is selected from the group consisting of: bell-shaped, cigar-shaped, condensed spherical, spherical, oval, sausage-shaped, kidney-shaped and bullet-shaped.

In another embodiment, the methods of the present invention further comprise determining the spatial or numerical distribution of one or more classes of nuclear morphotypes within the tissue sample, wherein the spatial or numerical distributions of the one or more classes of nuclear morphotypes further characterizes the tissue sample. A particular spatial or numerical distribution is indicative of a normal, preneoplastic, neoplastic or metastatic tissue.

In another embodiment of the invention, the nuclei are contained in multinuclear syncytia or in mononuclear cells and wherein the tissue sample is adult tissue. In one embodiment, the presence of bell-shaped, cigar-shaped or bullet-shaped nuclei are indicative of preneoplasia, neoplasia or metastasis. In another embodiment, the appearance of multinuclear syncytia is indicative of neoplasia or metastasis. In one embodiment, structures indicative of amitotic symmetrical nuclear division are indicative of neoplasia or metastasis. In another embodiment, the presence of bell-shaped nuclei and the absence of multinuclear syncytia are indicative of preneoplasia. In yet another embodiment, the presence of non-spherical and non-oval nuclei in blood vessel wall tissue is indicative of an incipient atherosclerotic condition.

In another embodiment, the invention is directed to a method for identifying a cell of interest or multinuclear syncytium of interest in a cell culture or tissue sample, wherein the cell of interest or syncytium of interest is identified by visualizing nuclear morphology, wherein the cell of interest comprises a heteromorphic nuclear morphotype. In a particular embodiment, the cell or multinuclear syncytium is isolated from the tissue sample. In another embodiment, the cell of or multinuclear syncytium is isolated by microdissection, e.g., pressure-assisted laser microdissection. In one embodiment, the cell of interest or multinuclear syncytium is identified in a population of cells in culture. In another embodiment, the cell of interest or multinuclear syncytium is identified in a tissue sample. In another embodiment, the cell of interest or syncytium of interest comprises one or more amitotic nuclear division complexes. In yet another embodiment, the cell of interest is present within a multicellular aggregate of cells. In a particular embodiment, the cell of interest is present within a cluster of multicellular aggregates.

In another embodiment, the invention is directed to a cell of interest isolated or identified by the methods disclosed herein. In one embodiment, the invention is directed to a method for using a cell of interest isolated or identified by the methods disclosed herein to identify one or more macromolecular markers specific to the cell of interest, wherein the marker is indicative of a particular stage of development or pathology. In a particular embodiment, the macromolecular marker is an antigen, cell-surface marker, nucleic acid, protein, phosphorylated protein or glycosaminoglycan.

In another embodiment, the invention is directed to a method for diagnosing preneoplasia or neoplasia comprising identification of one or more macromolecular markers, wherein the identification of the one or more macromolecular markers in adult tissue is indicative of preneoplasia or neoplasia.

In another embodiment, the invention is directed to a method of identifying one or more anti-tumorigenic agents comprising: a) treating a mammal having a tumor with one or more candidate agents; b) determining the nuclear morphology of cells contained within a tumor sample obtained from the mammal; and c) comparing the nuclear morphology of the cells from the mammal treated with the candidate anti-tumorigenic agent with cells obtained from a mammal having a tumor but not treated with the candidate anti-tumorigenic agent, wherein elimination of cells comprising neoplastic nuclear morphotypes is indicative of the effectiveness of the agent as an anti-tumorigenic agent. In a particular embodiment, the neoplastic nuclei are selected from the group consisting of: bell-shaped nuclei, cigar-shaped nuclei and bullet-shaped nuclei. In another embodiment, the alteration in nuclear morphology comprises the elimination of bell-shaped nuclei. In one embodiment, the mammal is a rodent (e.g., a rat or mouse. In a particular embodiment, the nuclei are arranged in syncytia and the elimination of neoplastic nuclear morphotypes comprises a disruption of the syncytia.

In another embodiment, the invention is directed to a method of identifying one or more anti-tumorigenic agents comprising treating a cultured tumor tissue or cell sample with one or more candidate agents and evaluating the nuclear morphology of cells contained in the tumor sample, wherein the cells comprise heteromorphic nuclear morphotypes, wherein in the absence of an anti-tumorigenic agent, the cultured tumor cells maintain their heteromorphic nuclear morphotypes, and wherein the elimination of neoplastic nuclear morphotypes is indicative of the effectiveness of the agent as an anti-tumorigenic agent, and wherein the elimination of preneoplastic nuclear morphotypes is indicative of a tumor preventative agent. In a particular embodiment, the altered nuclear morphology comprises the elimination of one or more nuclear morphotypes selected from the group consisting of: bell-shaped nuclei, cigar-shaped nuclei and bullet-shaped nuclei. In one embodiment, the alteration in nuclear morphology comprises the elimination of bell-shaped nuclei. In one embodiment, the nuclei are arranged in syncytia and the elimination of neoplastic nuclear morphotypes comprises a disruption of the syncytia.

In another embodiment, the invention is directed to a method for preparing a mammalian tissue sample suitable for the identification of cells comprising nuclei having maximum diameters up to about 50 microns, comprising: a) disrupting cellular adhesions of cellular sheets of the tissue sample; and b) spreading the cells with disrupted adhesions onto a hard surface, wherein the structural integrity of the nucleus of the cells remains intact, thus rendering the sample suitable for the identification of heteromorphic nuclear morphotype cells. In one embodiment, the tissue sample is sectioned into layers wherein the layers obtained exceed the thickness of a cell. In another embodiment, the tissue sample forms a layer on the microscope slide of about 0.5 millimeters. In a particular embodiment, the tissue sample forms a layer greater than about 50 microns. In another embodiment, cellular adhesions of the tissue sample are chemically disrupted (e.g., by treatment with 45% acetic acid). In a particular embodiment, the fixed, chemically disrupted tissue samples prior to spreading are about 1 mm$^2$ in area. In a particular embodiment, the tissue sample is a human tissue sample. In a particular embodiment, the cellular sheets are about 1 mm$^2$ in area. In another embodiment, the hard surface is a microscope slide.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 shows nuclear morphotypes observed in interphase and early prophase (E.P.) cells in human embryo gut, normal colonic mucosa, adenomas and adenocarcinomas. * Bell-shaped nuclei are rarely observed in adult colon. Scale bar, 5 μm.

FIG. 2A shows fetal gut, 5-7 weeks, at low magnification (140×) with stained nuclei (left image) and phase contrast/autofluorescent images of different gut sections (right image). Distinctly non-spherical nuclei appear to be arranged in a linear order (indicated by dashed lines) that is defined by "tube-like" structures in phase contrast images. These tube-like structures appear throughout the gut sections observed with other cell groupings interspersed among the tubes. FIG. 2B shows a phase contrast image (left frame) and stained nuclei image (middle) of the identical gut section overlaid (right) to demonstrate that the apparent linear orientation of the nuclei are in fact constrained by the tube-like structure which is itself about 50 microns in diameter. Magnification (280×) of the nuclei (middle frame) shows that these non-spherical nuclei appear to be in the form of cups or bells. FIG. 2C shows magnified images (1400×) of nuclei in linear array. These arrayed nuclei have a reproducible bell shape that is apparently hollow. The "head to toe" orientation of the bells is preserved in all embryonic tubes observed, but tubes snake backwards and forwards such that parallel tubes can have locally anti-parallel bell-shaped nuclei orientation. Scale bars, 100 μm at low and 5 μm at high magnification.

FIG. 3A: Symmetrical amitosis: a bell-shaped nucleus apparently emerges from a bell-shaped nucleus. A variety of bell-shaped morphotypes are observed but their amitoses show indistinguishable bell-shaped morphotypic characteristics such as the ratio bell mouth width/length as shown in these three examples; FIG. 3B: Asymmetrical amitosis: a solid nuclear form apparently emerges from within the bell-shaped nucleus. Shown are four images in which a spherical condensed nucleus is seen to be formed deep in the bell, and apparently emerges with nucleoplasmic connections to the bell before separating completely; FIG. 3C: spherical uncondensed nucleus coming out of the mouth of the bell-shaped nucleus; FIG. 3D: egg-shaped ("oval") nucleus emerging from bell; FIG. 3E: bean-shaped ("kidney-shaped") nucleus emerging from bell; FIG. 3F: cigar-shaped nucleus emerging from bell. Scale bar, 5 μm.

FIG. 4A shows crypts of about 2000 spherical and ovoid nuclei occasionally (<1/100) contained a recognizable bell-shaped nucleus (arrow in lower left corner) located at the bottom of the crypt (right corner: enlarged image of the nucleus). FIG. 4B shows the crypt base with another bell-shaped nucleus among other nuclear morphotypes peculiar to the base. FIG. 4C shows various morphotypes of interphase and mitotic nuclei of the walls and luminal surface in a well-spread crypt. The enlarged images show: (i) spherical and ovoid interphase nuclei, (ii, ii) early prophases of spherical and oval-shaped nuclei, and (iv) an anatelophase nucleus. Scale bars, 100 μm for low and 5 μm for high magnification images.

FIG. 5A shows a large branching crypt characteristic of adenomas. Crypt bases and luminal openings are regularly arranged in a manner similar to normal colonic sections. FIG. 5B shows an irregular crypt-like structure that was also observed throughout the adenoma samples. Typically two, but sometimes one, four or even eight bell-shaped nuclei (insert) appear at the base of these large (>4000 cell) irregular crypts. FIG. 5C shows a cluster of cells of similar nuclear morphotype containing one bell-shaped nucleus. These simple clusters contain 16, 32, 64, and 128 total cells. Left panel: Feulgen-Giemsa stain. Right panel: phase contrast autofluorescent image. FIG. 5D illustrates different contexts in which bell-shaped nuclei appear in adenomas: (i) cluster with 31 ovoid nuclei and one bell-shaped nucleus, (ii) multiple bell-shaped nuclei in "shoulder-to-shoulder" arrangement, (iii) bell-shaped nuclei arranged in "shoulder-to-shoulder" pattern (arrowed) in larger "circles", (iii) irregular mixture of ~250 nuclei of with several bell-shaped nuclei suggestive of nascent crypt bases found scattered throughout adenomas. FIG. 5E shows an irregular crypt-like structure containing apparently clonal patches of cells of five different nuclear morphotypes with one bell-shaped nucleus (arrow) at the base. Scale bar, 100 μm for low and 5 μm for high magnification images.

FIG. 6A shows very large crypt-like structures (>8000 cells), with branches with frequent break points. The bases of these structures were indistinguishable from those of normal colonic crypts except for the presence of two (typically) bell-shaped nuclei as in adenomas. The base to lumen orientation of crypt-like structures preserved in adenomas is not observed in adenocarcinomas in which crypt orientations appear to be random. The arrow indicates a small ~250 cell crypt-like structure commonly found near the surface of the tumor. FIG. 6B shows shoulder to shoulder groupings of bell-shaped nuclei found throughout the tumor interior. FIG. 6C shows the interior tumor mass with multiple examples of bell-shaped nuclei locally oriented in both shoulder to shoulder and head to toe configurations. The head to toe orientation is found only in the tumor interior, the shoulder-to-shoulder orientation found both interiorly and near the tumor surface among the crypt-like structures. Bell-shaped nuclei account for ~0.2% of all nuclei in the tumor interior. Scale, 100 μm for low and 5 μm for high magnification images.

FIGS. 7A-7E are enlarged images depicting amitoses in adenocarcinomas. FIG. 7A shows symmetrical amitoses creating two bell-shaped nuclei of distinct morphologies in irregular crypts. The arrow in the left image indicates the bottom of the bell of the newly arising nucleus. FIG. 7B shows asymmetrical amitosis creating a spherical nucleus. FIG. 7C shows asymmetrical amitoses creating oval-shaped nucleus. FIG. 7D shows symmetrical amitoses forming "cigar"-shaped nuclei. FIG. 7E shows asymmetrical amitosis creating a "sausage"-shaped nucleus with curious dark staining element (upper arrow) distinct from what appear to be condensed chromosomes at the lip of the bell-shaped nucleus (lower arrow). Scale, 5 μm.

DETAILED DESCRIPTION OF THE INVENTION

Figure 2A:
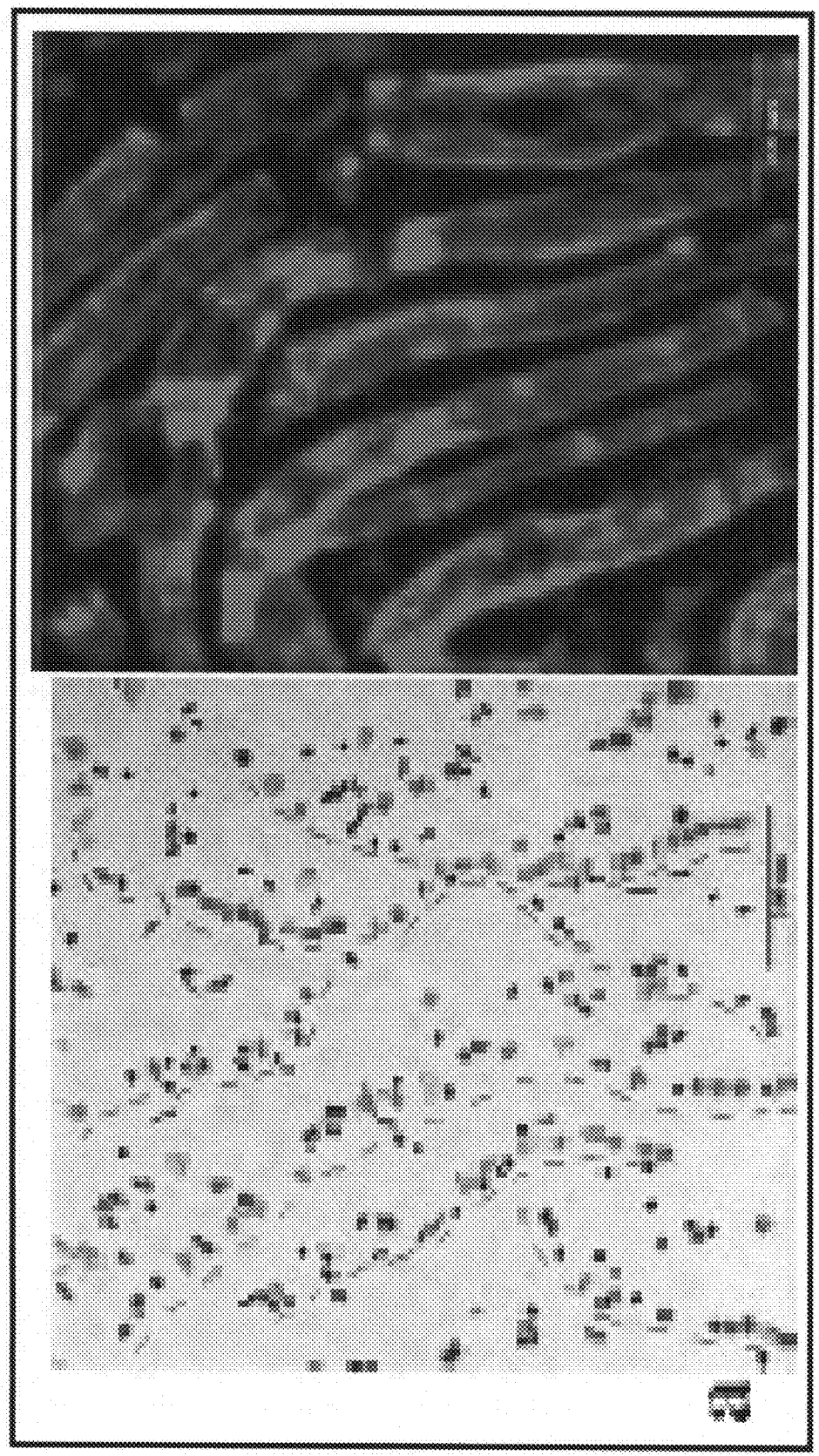
FIGS. 2A-2C show microscopic images of embryonic gut.

The present invention relates to the unexpected discovery of large cell nuclei with distinct morphologies throughout fetal gut (5-7 wks), colonic adenomas, and adenocarcinomas, some of which are not present in normal (non-neoplastic) adult colon. These "heteromorphic nuclear morphotypes" (e.g., nuclear morphotypes that differ from the normally spheroid or ovoid nuclei of cells in adult organs), were observed in embryonic tissues and only rarely in adult tissues. One remarkable nuclear morphotype has a nucleus shaped like a hollow bell (approximately 10-15 microns in height and approximately 7-12 microns in bell mouth diameter). These bell-shaped structures appear to divide symmetrically by an amitotic process resembling the separation of two paper cups. Furthermore, at least seven other nuclear forms were observed to emerge from bell-shaped nuclei in asymmetrical amitoses. Cells containing these derivative nuclear forms subsequently divide by mitoses forming clonal populations of identical nuclear morphotypes in embryos, adenomas and adenocarcinomas. Cells with bell-shaped nuclei thus appear to be responsible for both net growth and differentiation in embryonic gut, adenomas and adenocarcinomas and fulfill the requirements for generative, multipotent stem cells in embryogenesis and carcinogenesis. The specific differential occurrence of bell-shaped nuclei in cells demonstrating both symmetrical and asymmetrical amitoses theoretically required for net stem cell growth and differentiation in embryonic/fetal tissue sample as opposed to adult tissue, allows for one skilled in the art of microscopic histology/pathology to classify cells as stem cells or not-stem cells according to their nuclear morphology.

A concept shared in both embryology and oncology is that the multiple cell types that are observed in organs and tumors derived from particular organs arose from precursor "stem" cells capable of net growth by symmetrical cell divisions in which a cell division produces two identical precursor "stem" cells and differentiation by asymmetrical cell division producing one precursor "stem" cell and one differentiated cell. This differentiated cell may then divide an additional number of times to create a large number of differentiated cells that eventually reach a non-dividing terminal stage followed by programmed cell death. An "extinction" division occurs when a cell differentiates into two more highly differentiated cells.

The term "stem cell" has many different levels of definition in the scientific literature. In general it is meant to comprise the set of cells that maintain an undifferentiated or partially differentiated phenotype but can in certain circumstances give rise to cells with different phenotypes. The use of the generic term and more specific terms used herein distinguish among types of stem cells based on the scientific observations that comprise the teachings disclosed herein.

The term "embryonic stem cell" as used herein comprises the set of cells in the early mammalian embryo that divide by ordinary mitosis and can, upon transplantation into a uterine environment, give rise to a complete placenta and fetus. They are thus characterized as "totipotent". Such cells can be cultivated ex vivo, dividing by mitosis, to form very large numbers of embryonic stem cells—each capable of giving rise to a placenta and fetus. It is not known whether or not any embryonic stem cells persist as such in a growing mammalian fetus, neonatal, juvenile or adult animal. It is possible that certain clusters of undifferentiated cells found throughout tissues in adult mammals represent colonies of totipotent embryonic stem cells. With regard to nuclear morphotype, this form of stem cell contains spherical or nearly spherical nuclei.

The term "fetal-juvenile stem cell" as used herein comprises the set of cells and multinuclear syncytia observed in human fetuses by the fifth week of gestation and in human preoplastic, neoplastic and metastatic lesions that contain bell-shaped nuclei. As used herein, "syncytia" are multinuclear structures lacking cell septa. Multiple nuclei are present but they are not segregated into individual compartments within the syncytia by membranes. The fetal juvenile stem cell undergoes both symmetrical nuclear division creating two identical bell-shaped nuclei, and asymmetrical nuclear division creating one bell-shaped nucleus and one nucleus of the several heteromorphic nuclear morphotypes observed in tissue and tumor samples such as, for example, kidney-shaped, cigar-shaped, sausage-shaped, oval or spherical nuclei that subsequently increase in number by mitosis. Both symmetrical and asymmetrical nuclear divisions of bell-shaped nuclei are amitotic insofar as there is no general condensation of the genome as chromosomes, no formation of a mitotic spindle, and no condensation or separation of chromosomes as in prophase, metaphase, anaphase and telophase as observed for more than a century and previously believed to be the only relevant form of nuclear division in mammalian cells (including mammalian tumors). Symmetrical division permits the net growth of fetal-juvenile stem cells and presumably accounts for the growth of tissues and organs throughout fetal, neonatal and juvenile stages of life. Asymmetrical divisions of fetal-juvenile stem cells permits creation of cells with alternate phenotypes and presumably accounts for the differentiated cell types that comprise the parenchyma of developing and growing organs. Insofar as nuclear morphotype is a recognizable characteristic of a cell and/or nucleus, cells differing in nuclear morphotype can be characterized as differing in cellular or nuclear phenotype without reference to a characteristic other than nuclear morphotype.

The term "adult maintenance stem cell" as used herein comprises the theoretical form of cell that by regular asymmetrical cell division creates a first transitional cell that, by subsequent mitotic division and ultimately programmed cell death, defines the differentiated turnover unit of differentiated cell tissues such as, for example, the colonic crypts. The same asymmetrical division of the adult maintenance stem cell would also create a new adult maintenance stem cell. As very few colonic crypts have been observed with the bell-shaped nuclei characteristic of the observed fetal-juvenile stem cells in the base of the crypts, it is reasonable to conclude that fetal-juvenile stem cell nuclei undergo a metamorphosis marking the cessation of net growth of juvenile organs and the beginning of the adult stage of life. It is unknown whether the asymmetric divisions of adult maintenance stem cells are mitotic or amitotic in nature.

The term "preneoplastic stem cell" as used herein describe mononuclear cells comprising the observed bell-shaped nuclei found in the base of adenomatous colonic crypts. These cells are observed in small aggregates of cells of identical nuclear morphotypes, in large clusters of such aggregates in which each aggregate creating the cluster contains nuclei of the same morphotype with different aggregates contain nuclei of differing morphotype, and in subregions of the colonic preneoplastic lesions. These cells can have nuclei arranged in a "shoulder-to shoulder" relationship. Syncytia containing bell-shaped nuclei have not been observed in human colonic preneoplastic lesions nor have the individual bell-shaped nuclei been observed in symmetrical nuclear division, a condition interpreted as consistent with the slow growth of preneoplastic lesions at approximately the growth rate of the juvenile tissues from which they were derived.

The term "neoplastic stem cell" or "tumor stem cell" as used herein comprises the bell-shaped nuclei found in cancerous tumors, e.g., adenocarcinomas of the human colon, metastases of colonic tumors and tumors of the human pancreas. These neoplastic stem cells are differentiated from preneoplastic stem cells by their presence in all of the observed multicellular aggregates of preneoplasia, but, in addition, being found and found to be dividing by amitotic symmetrical nuclear divisions in multinuclear tubular syncytia. The syncytia found in tumors are less extensive than those observed in early fetal gut tissue, but the syncytia and bell-shaped structures undergoing symmetrical nuclear divisions appear to be clear distinguishing characteristics between pre-neoplastic and neoplastic tissue.

The heteromorphic nuclear morphotypes described herein can also be found in cells and syncytia derived from, for example, a tissue sample or cells grown in culture. The methods described herein can be applied to any tissue sample to identify cells or syncytia containing the heteromorphic nuclear morphotypes. In particular, tumor tissue samples can be used to identify and enumerate heteromorphic nuclear morphotypes.

As used herein, "tumor" refers to an abnormal growth of tissue resulting from progressive multiplication of cells serving no physiological function that is beneficial to the carrier (also referred to as a "neoplasm"). A 'benign' tumor is a tumor limited to the site of origin without invasion of the surrounding tissue. Malignant tumors are those that can or do spread by invasion of surrounding tissue and metastasis while benign tumors neither invade nor metastasize. As used herein, "neoplastic" refers to a cellular condition of rapid net cell growth giving rise to a lethal tumor, whether benign or malignant. Neoplastic cells lead to tumors, although not necessarily invasive or metastatic tumors. "Cancer" refers to the disease of one or more rapidly growing colonies of cells that cause death by interfering with bodily functions. Cancer cells can break away from a primary tumor, penetrate into lymphatic and blood vessels, circulate through the bloodstream, and grow in a new site (metastasize) in normal tissues elsewhere in the body.

As used herein, a "pre-cancerous condition" is characterized as a slowly growing colony that, if unchecked, has the potential to give rise to cancer (e.g., neoplastic tumors). This condition is characterized, for example, by the presence of an abnormal microanatomical structure or structures such as, for example, polyps in the colon or bell-shaped nuclei within an adult tissue sample.

The "net stem cell growth rate" is the rate (divisions per unit time) of symmetrical fetal-juvenile stem cell divisions that account for net growth of a tissue, organ or organism. In general stem cell net growth rates decrease with increased development of an organism throughout fetal, neonatal and juvenile life to zero in adults.

Tumors display many of the characteristics of the adult organ/system from which they are derived including formation of complex multi-cellular structures, such as, for example, colonic crypts in adenocarcinomas of the colon. Insofar as tumors have been derived from a single precursor cell that had the ability of both net growth and differentiation, it has been reasoned that "tumor stem cells" must exist and share many characteristics organ-specific stem cells (partially undifferentiated cells capable of giving rise to specific organ cells and tissues). For example, in the case of the cells of the bone marrow from which leukemias arise, certain antigens have been recognized that allow identification of marrow cell sub-populations that contain one or a small number cells capable of giving rise to a complete blood cell system on transplantation. Similarly a subfraction of tumor cells can be recognized by specific antigens expressed by some tumor cells. According to this logic, one cell among the sub-population so recognized gives rise to a new differentiated tumor upon experimental transplantation of mixtures of tumor cells. Continuing with this reasoning, the "organ-specific stem cells" and "tumor stem cells" exist among such antigen expressing sub-populations. These antigens are used to identify and isolate cell populations containing at least one pluripotent stem cell, but will also identify a large majority of cells that cannot act as stem cells. None of the cells of these populations as isolated have been found to undergo asymmetrical cellular divisions that are considered a "shibboleth" of true stem cells or organs and tumors.

Presented here are methods for identifying cells that are in fact "organ-specific stem cells" or "tumor stem cells" as opposed to subfractions of organs or tumors enriched for such cells. The identification is based on the heteromorphic nuclear morphotypes and nuclear divisions and/or arrangements described herein. With these methods, it would be possible to isolate such stem cells and discover their specific biochemistry and molecular biologies with the goals of isolating cells permitting organ regeneration, interfering with the growth of pre-cancerous lesions and/or the killing of the cells specifically responsible for tumor growth and reappearance after attempts at therapy.

Such organ-specific and tumor stem cells are further identified in fetal organs, tumors and tumor metastases by their participation as a class in two specific previously unreported, microscopically visible forms of nuclear division. In the first of these two forms of nuclear division there is no general condensation of chromosomes and formation of a mitotic apparatus; instead one bell-shaped nucleus appears to give rise to an identical bell-shaped nucleus in a manner similar to separation of two paper cups. This symmetrical, amitotic division provides for the net growth of stem cells in fetal and tumor samples. In the second form of stem cell-specific nuclear division there is also no general condensation of chromosomes and formation of a mitotic apparatus; instead one bell-shaped nucleus appears to give rise to a bell-shaped nucleus and a nucleus of a nucleus having one of the several nuclear morphotypes observed in fetal tissue and tumor samplers (FIG. 3). This asymmetrical, amitotic division provides for creation of differentiated cells by stem cells in fetal tissue and tumors. Mitotic division of nuclei without bell-shaped nuclei are observed in fetal tissue and tumor samples creating the majority of total cells in such samples. Thus the process of identification of stem cells permits direct observation of cells with bell-shaped nuclei undergoing both symmetrical and asymmetrical nuclear divisions, both necessary for classification as organ-specific and tumor-specific stem cells.

Such organ-specific and tumor stem cells are further identified in fetal organs, tumors and tumor metastases by their participation as a class in specific previously unreported multi-nuclear structures resembling long tubes in which bell-shaped nuclei are regularly aligned in a fashion resembling a series of separated paper cups retaining the head-to-toe relationship as in the stacked cup set.

These stem cell-specific nuclear morphotypes (bell-shaped), specific forms of nuclear division (symmetrical and asymmetrical amitotic nuclear divisions) and specific form of participation in multinuclear structures (long multinuclear tubes) are essentially absent from adult organs. However, the stem cell-specific nuclear morphotype is observed among the cells of preneoplastic lesions and rarely, as single nuclei, widely dispersed in adult organs (for example, somewhat fewer than one in two million nuclei of adult colonic crypts have been found to be bell-shaped nuclei).

The unexpected discovery of these heteromorphic nuclear morphotypes and their differential occurrence in stem cells, normal adult tissue and tumor tissue allows for one skilled in the art to classify cells according to their nuclear morphology. In addition, stem cells can be isolated based on their nuclear morphology, anti-tumorigenic agents can be screened or identified based on the appearance or disappearance of tumor-specific morphotypes, and tissue samples can be classified (e.g., normal or abnormal; neoplastic or non-neoplastic) by determining the morphotypes present in the cells of the tissue. As a result of this cell classification, a diagnosis can be made as to whether or not an individual has cancer or a pre-cancerous lesion. Although a particular method (see below) is used in the Examples to allow for the visualization of these novel morphotypes, any method that allows for the identification and evaluation of nuclear morphotypes is suitable for the classification of cells, tissues and samples, and subsequent diagnosis of disease, as well as provide the basis for assays used to identify anti-tumorigenic agents (e.g., agents effective in inhibiting or decreasing tumorigenic cell growth). Such methods include phase contrast microscopy, confocal microscopy, two electron or two wavelength microscopy and small angle scatter flow cytometry.

Figure 1:
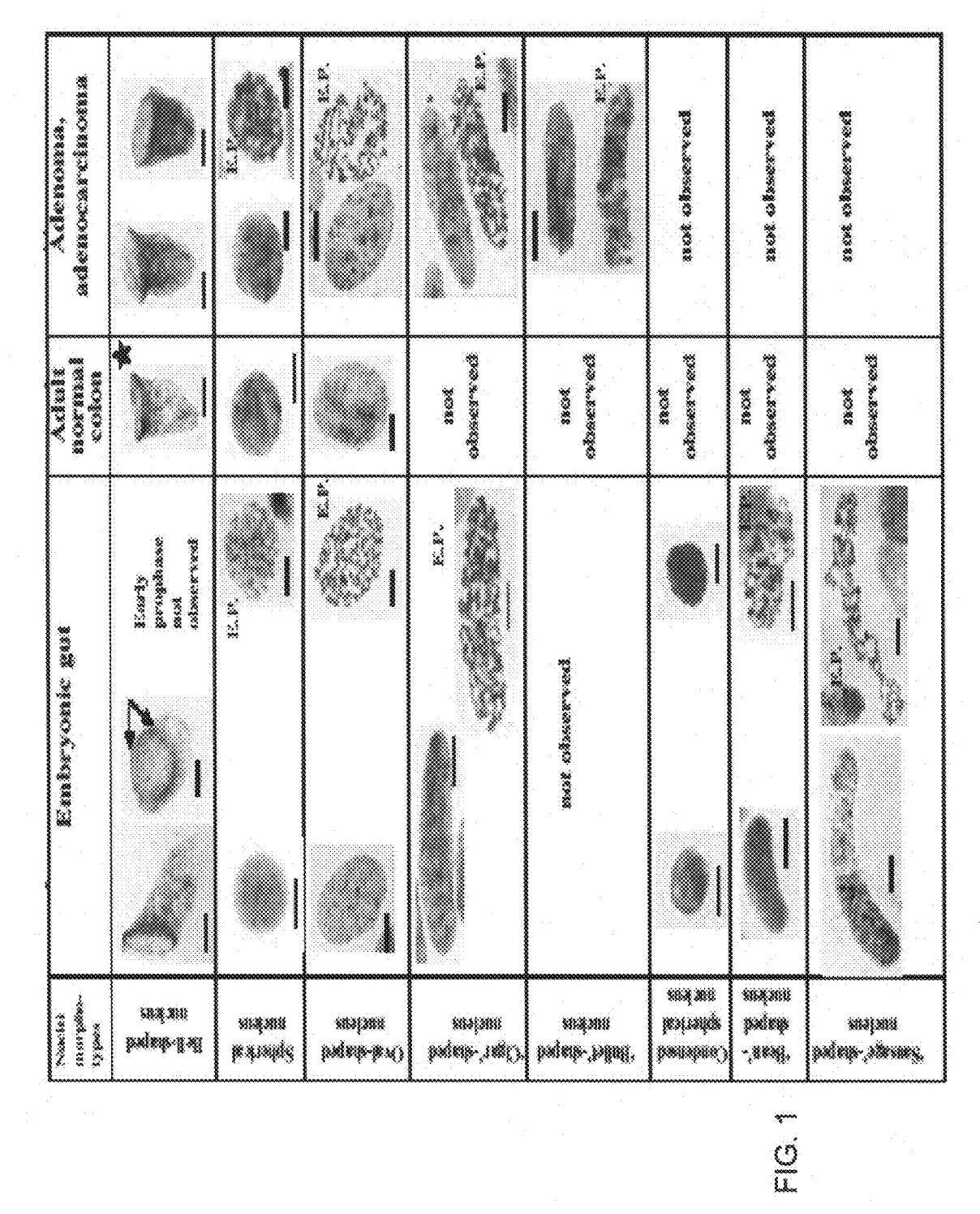

For the purposes of the present invention, thick, ~0.5 mm, sections of normal adult human colonic epithelium, colonic adenomas, colonic adenocarcinomas, and fetal gut were prepared for microscopic observation as described in the Exemplification below. The thickness of the tissue sheet layer should be at least the thickness of an intact cell (and not just a section or slice of the cell). An array of large spheroidal and non-spheroidal nuclear forms appeared in all samples as summarized in FIG. 1. All of the samples contained the spheroid and ovoid nuclei normally observed in histological sections of adult colonic crypts but also contained extraordinary, previously unreported nuclear morphotypes. Embryonic tissue contained nuclei shaped like bells, tapered cigars, kidney beans, sausages and small spheres. Normal adult colonic crypts contained an occasional bell-shaped nucleus in the crypt bases but the vast majority were the large spheres and ovoid structures. In some views it appears that cell nuclei near the crypt bases may be "discoid". In adenomas and adenocarcinomas the nuclear shapes, in addition to the spheroid and ovoid nuclei, included tapered cigars and an additional form that looks like a cigar with a bitten off end dubbed "bullet-shaped".

Crypt structures were preserved by the preparative procedure and were clearly observed in normal colon, adenomas and adenocarcinomas. The ~0.5 mm sample sections employed were much thicker than the largest nuclear form observed, the sausage-shape, which was ~40 microns in length. All of the nuclear structures, except the 4 micron "condensed spherical nuclei", had at least one internal axis longer than the 5 micron sections usually employed in pathological evaluations. Furthermore, there is a fair degree of morphological variation among nuclei that can be classified as "bell-shaped" or "cigar-shaped" etc., suggesting independent lineages and physiological functionalities.

The phenomena of bell-shaped nuclei, their symmetric and asymmetric forms of amitosis, or the collection of nuclear morphotypes in adult, preneoplastic, neoplastic and embryonic tissue described herein have not been previously reported (see Example 2). The tubular encasement of linearly arrayed bell-shaped nuclei in embryos and adenocarcinomas is also apparently a novel observation. The reason that they have not been previously observed may lie in the differences between standard histological practices and those employed and disclosed herein. Two clear procedural differences are evident. First, all tissues for fixation were sectioned and fixed within a short period of time (for example, within 30 minutes) of surgical removal. Preparations after 30 minutes may begin to show degradation of the nuclear forms, although careful tissue preparation may prevent degradation. Second is the difference between thin section procedures practiced in medical pathology and thick section fixation protocols, disclosed herein—the latter preserving, and the former apparently destroying, the structures/conditions that maintain these nuclear shapes.

Amitosis, as a phenomenon, has been reported in a number of protozoans and primitive metazoans (Orias, E., 1991, *J. Protozool.*, 38:217-221; Prescott, D., 1994, *Proc. Natl. Acad. Sci USA*, 92:136-140). However, these amitoses were unlike those reported here insofar as protozoan amitotic nuclear division occurred by formation of a nuclear cleft and pinching off two separate approximately equal nuclei (Fujiu, K. and Numata, O., 2000, *Cell Motil. Cytoskeleton*, 46:17-27). Amitotic divisions of the sort similar to those seen in protozoans have been reported, however, in a number of different tumors (Okuyama, S. 1991, *Tohoku J. Exp. Med.*, 164:247-249; Okuyama, S., 1992, *Tohoku J. Exp. Med*, 168:445-448; Elias, H. and Fong, B., 1978, *Hum. Pathol.*, 9:679-684; Elias, H. and Hyde, D., 1982, *Hum. Pathol.*, 3:635-639).

The observations showing that the arrangement of chromosomes in early prophase nuclei of the mitotic cells maintains the shape of the interphase nucleus also deserve attention. It appears that the different chromosomes form a highly structured mosaic that may have important consequences in defining a cell's phenotype. The relationship between the spatial arrangement of chromosomes in interphase nuclei and cell physiology is an active area of exploration (Misteli, T., 2001, *Science*, 291:843-847; Thomas, C. et al., 2001, *Proc. Natl. Acad. Sci. USA*, 99:1972-1977; Parada, L. et al., 2004, *Exp. Cell Res.*, 296:64-70).

Based on the observations cited below, cells with bell-shaped nuclei are pluripotent cells that represent the generative cell of the developing and growing tumors and preneoplastic lesions such as, for example, colorectal tumors, adenomas and adenocarcinomas. Thus, the bell-shaped nuclear morphotype is indicative of pluripotent stem cells and can be used as diagnostic criteria for preneoplastic and neoplastic tissue in adult tissue samples. In addition, the organization of bell-shaped nuclei (e.g., into tube-like structures or spider-web-like structures) can be further indicative of the progression of tumor development (e.g., neoplasia or metastatic tumors).

The pluripotency of bell-shaped nuclei is demonstrated by the images of multiple forms of nuclei emerging from bell-shaped nuclei in asymmetrical amitotic divisions. Insofar as egg-, sausage, kidney-, bullet- and cigar-shaped nuclei are observed emerging from bell-shaped nuclei and no other nuclear forms are observed, they represent the set of functions necessary for the tissue in which they reside to persist. There can indeed be multiple forms of cells with bell-shaped nuclei as suggested by the morphological variations among bell-shaped nuclei observed.

The numbers and symmetrical amitotic frequencies of cells with bell-shaped nuclei are consistent with the generative element of this hypothesis. They are observed in large numbers in embryos, rare in normal adult colon free of neoplasia, present, in small numbers (for example, about 1,000) in adenomas of a few cubic millimeters and large numbers (for example, less than about 1,000,000) in adenocarcinomas of several cubic centimeters. Their division rates in the embryo and adenocarcinomas are estimated to be approximately 20 divisions per year consistent with the estimated net growth rates of colonic adenocarcinomas (Herrero-Jimenez, P. et al., 1998, *Mutat. Res.*, 400:553-578). Their symmetrical amitotic fraction in adenomas is less than $1/1000$ and none have been seen to date. This negative observation is important in itself. The frequency of cell divisions for the generative cell or "cell at risk of promotion" in human colonic preneoplastic lesions has been estimated by calculation to be about one in six years (Herrero-Jimenez, P. et al., 2000, *Mutat. Res.*, 447:73-116). Assuming amitosis could be recognized for a three hour period, a frequency of less than $6/100,000$ would be expected. Thus, the very low symmetrical amitotic rate of adenomas is consistent with expectation for the generative cells of colonic preneoplasia.

It is possible that the cells with bell-shaped nuclei are phased out at the end of juvenile growth. Retinoblasts phase into retinocytes in early childhood and remove the risk of retinoblastoma in retinoblastoma gene heterozygotes (Knudson, A., 1971, *Proc. Natl. Acad Sci. USA,* 68:820-823). It could be that colon tumor "initiation" by mutations in genes such as APC prevents this phasing out process. If so, bell-shaped nuclei should be found in the bases of colonic crypts in neonates and juveniles.

From the appearance of bell-shaped nuclei in embryonic and carcinogenic tissues, relationships between embryogenesis and carcinogenesis can be inferred. Cancer researchers have considered tumors to reflect characteristics of embryos for more than a century. Erenpresia, J. and Helmtrud, I. (1999, *Mech. Aging and Develop.,* 108:227-238) cited J. Cohnheim (1875, Virchows Arch., 65:64; 1877-1880, Vorelesungen uber allgemeine Pathologie. Ein Handbuch fur Artzte und Studierende. Berlin, Hirchswald 1-2 691S) as first hypothesizing that tumors arise from fetal cells that inappropriately persist in adult tissues. The expression of carcino-embryonic antigens in tumors and appearance in tumors of a wide spectrum of gene products, mRNAs and proteins, that are also found in embryos has reinforced the broad hypothesis that oncogenesis involves the appearance of cells with embryo-like qualities. The finding of morphological cell types essentially identical in form, amitotic and mitotic behavior in adenocarcinomas and embryonic colon calls for a more specific restatement of the carcino-embryonic hypothesis in terms closely echoing Cohnheim and using the more recent arguments and experimental demonstrations indicating the existence of tumor stem cells (Pardal et al., 2003, *Nature Rev.,* 3:895-902).

These new observations, integrated into the body of cancer research and ideas of the past 130 years, suggest a simple hypothesis about the origin and characteristics of late-onset colonic adenomas and adenocarcinomas: tumor initiating mutations, e.g., APC gene inactivations, occur in a cell with a bell-shaped nucleus before this cell form is phased out during or at the end of the juvenile period. Such initiated cells with bell-shaped nuclei would simply continue to divide and create new colonic crypts at the same rate as they did in juveniles (Herrero-Jimenez, P. et al., 1998, *Mutat. Res.,* 400:553-578; Herrero-Jimenez, P. et al., 2000, *Mutat. Res.,* 447:73-116). The resultant local crowding creates the "polyp". Either actively, by an additional genetic change or changes (including changes in gene imprinting), or passively by biochemical changes occurring within the growing adenoma, a single cell with a bell-shaped nucleus reverts to an earlier embryonic condition and gives rise, as in the embryo, to a rapidly growing array of cells almost indistinguishable from embryonic tissue. Untreated, this continued growth leads to colonic obstruction and/or metastases and death.

In the most general sense these observations point to a highly ordered nature of carcinogenesis in which distinctly non-chaotic behavior is observed in adenomas that preserve the slow but constant growth rate of juveniles and in adenocarcinomas that recreate an ordered ensemble of cell types and growth rates observed during embryogenesis. In the sense that the existing biological forms have been selected from a myriad of degenerate possibilities ("trying all combinations"), it is perhaps not surprising that carcinogenesis in humans might represent a rare but simple failure to cease juvenile growth and a subsequent rare reversion to an ordered embryonic cell state.

These observations suggest that cells with bell-shaped nuclei would be targets for more specific and therefore more effective forms of tumor prevention and therapy. Were it possible to drop the net growth rate of preneoplastic colonies by 50%, most late onset cancer types would not appear during a human lifetime of 100 years (Herrero-Jimenez, P. et al., 1998, *Mutat. Res.,* 400:553-578; Herrero-Jimenez, P. et al., 2000, *Mutat. Res.,* 447:73-116). It is reasonable to believe that cells with heteromorphic nuclear morphotypes such as, for example, bell-shaped nuclei are the tumor stem cells in adenomas and adenocarcinomas of the colon, one might target the mechanisms that confer their special characteristics in DNA synthesis and segregation either in symmetrical divisions of net growth or the asymmetric divisions that provide the cells that divide by mitosis and provide the bulk of the tumor mass. It may be that these cell types or entubated bell-shaped nuclei operate under different biochemical rules and that these, if understood, might also be exploited in tumor prevention and/or therapy (see, for example, the findings of Otto Warburg who discovered marked differences in mitochondrial biochemistry among embryonic, adult organ and cancer tissues (Warburg, O., 1956, *Science,* 123:309-314; Warburg, O. et al., 1960, *Z. Naturforsch B.,* 15B:378-379).

Reference to basic texts on invertebrates shows that a large sausage-shaped nucleus exists among the ciliated protozoans such as the pertirich *Vorticella* and the heterotrich "Stentor has a remarkable type of large nucleus resembling a string of beads . . . " (Buchsbaum, R. et al., 1971, *Animals Without Backbones,* 3rd ed., University of Chicago Press, Chicago, Ill.). These peculiarities of nuclear metamorphoses might even be linked in evolutionary time with the biochemistry of cells surviving in the pre-oxic environment insofar as they appear to grow in embryos, adenomas and adenomas in local milieu that would be expected to be oxygen poor prior to neo-vascularization. Warburg's discovery that amino acids provide the oxygen reducing equivalents for ATP generation in embryos and tumors suggests selection of a phenotype that treats oxygen as the limiting nutrient.

The heteromorphic nuclear morphotypes (e.g., bell-shaped nuclei) thus appear to represent a three-fold physiological nexus uniting evolutionary biology, embryogenesis and oncogenesis. To the genetic cycle of meiosis and mitosis, symmetrical and asymmetrical amitotic stages of lineal descent between the mitotic divisions of the post-fertilization period and the mitotic divisions that create most of the cellular mass of an animal must now be added.

The present invention is specifically directed to methods of classifying cell types based on nuclear morphology, their involvement in symmetrical and asymmetrical amitoses and their association in multicellular aggregates. For example, a tissue sample obtained from a mammal can be classified based on the presence or absence of heteromorphic nuclear morphotypes (e.g., bell-shaped nuclei, cigar-shaped nuclei and bullet-shaped nuclei). As FIG. 1 demonstrates, heteromorphic nuclear morphotypes are present in different stages of development and also at different stages of tumor development. For example, bell-shaped nuclei are found in fetal samples, rarely in adult samples, and prevalently in adenoma and adenocarcinoma samples. This supports the notion that heteromorphic nuclear morphotypes can be used to identify fetal juvenile stem cells as well as neoplastic stem cells in adult tissues. These results demonstrate a previously undocumented link between fetal stem cells and cancer stem cells. Thus, heteromorphic nuclear morphotypes that are indicative of fetal juvenile stem cells in fetuses are also indicative of cancer stem cells in adult tissues.

Figure 2B:
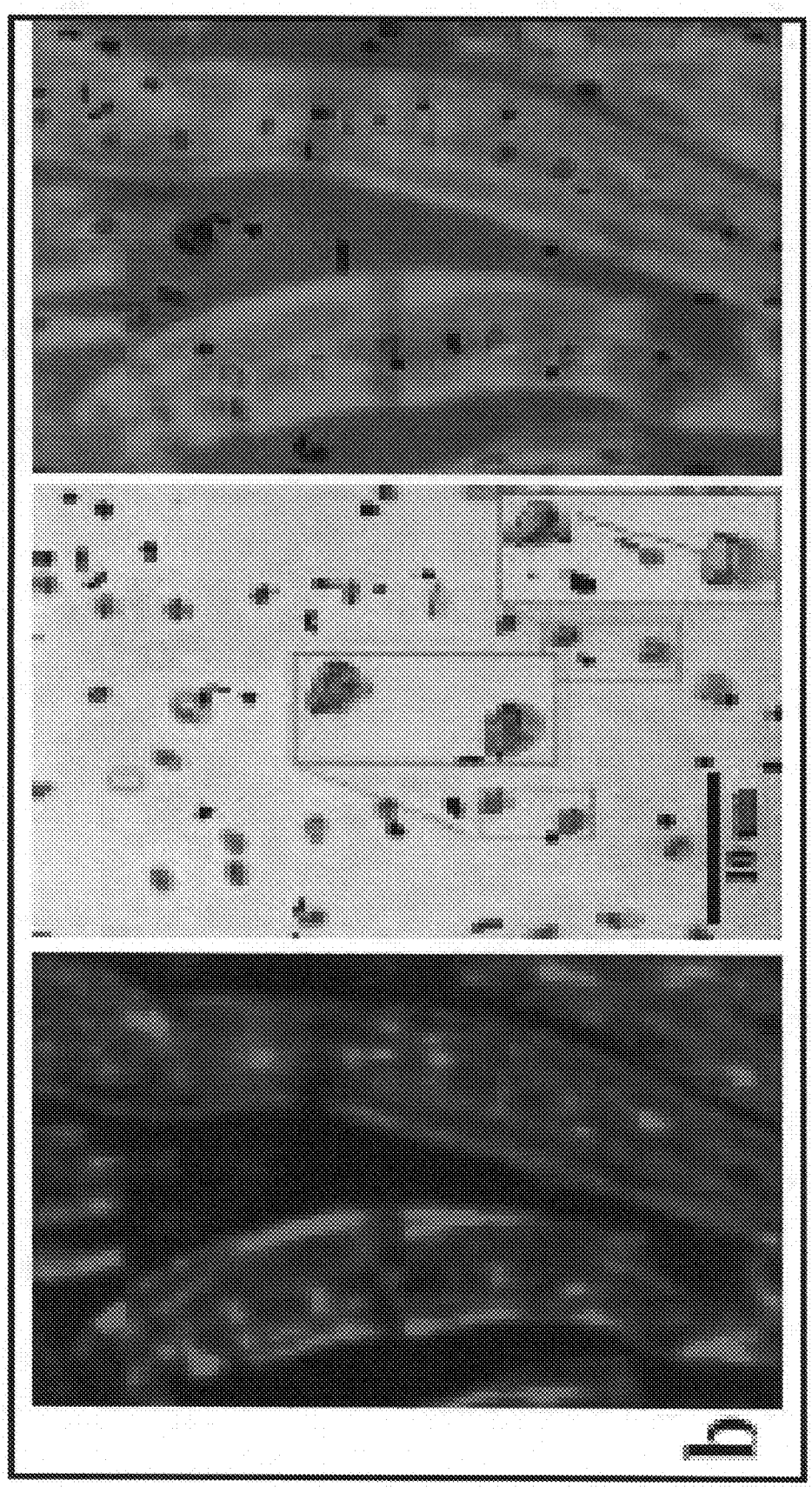
Figure 2C:
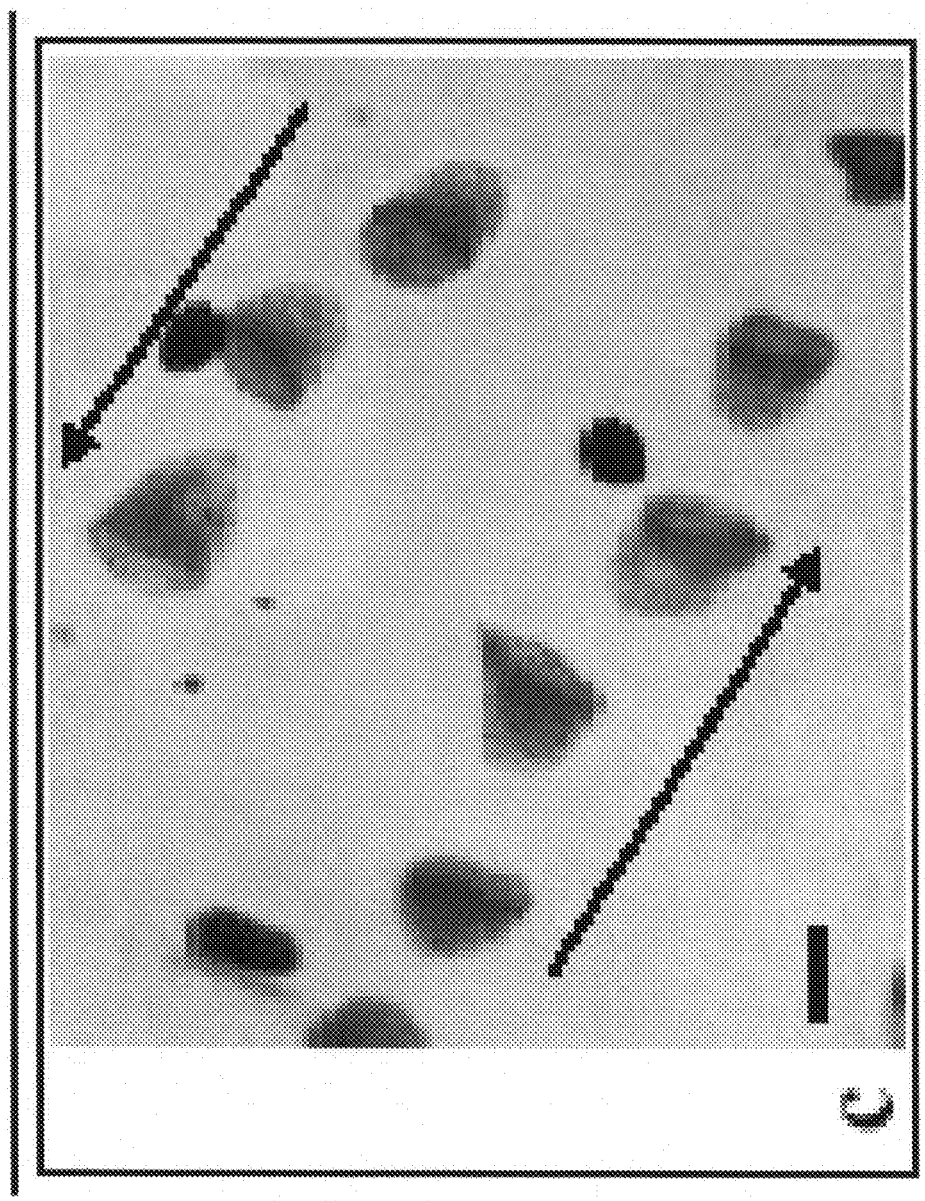

In addition, FIGS. 2A-2C show that heteromorphic nuclear morphotypes align in tube-like structures. As these tube-like structures are present in fetal samples and contain heteromorphic nuclear morphotypes (e.g., bell-shaped nuclei, cigar-shaped nuclei and bullet-shaped nuclei), the tube-like structures themselves can be used as indicia of fetal juvenile stem cells or neoplastic (e.g., tumor or cancer) stem cells in adult tissues.

Alternatively, the arraying of heteromorphic nuclear morphotypes into syncytia as shown in FIG. 5A-5E is indicative of differences between adenomas and adenocarcinomas. Therefore, the arrangement of nuclear morphotypes in multinuclear structures in a tissue sample can be used to differentiate among neoplastic samples at different stages of disease.

As heteromorphic nuclear morphotypes have been observed in other adult tissues and tumor samples (e.g., liver), one of skill in the art would recognize a preneoplastic or neoplastic lesions based on the presence of heteromorphic nuclear morphotypes in any adult tissue.

The present invention is also directed to methods for identifying anti-tumorigenic agents based on the appearance or disappearance of heteromorphic nuclear morphotypes specifically associated with preneoplastic or neoplastic tissues (e.g., bell-shaped nuclei, cigar-shaped nuclei and bullet-shaped nuclei). Candidate anti-tumorigenic agents can be screened, for example, in vivo in particular animal models (e.g., mammalian models, e.g., rodents such as, for example, mice or rats). Candidate anti-tumorigenic agents can be screened, for example, in clinical studies to discover if a trial regimen actually destroys the tumor stem cell component as opposed to the non-stem cell population that constitutes >99% of the cells in a tumor. With the process described herein candidate anti-tumor agents or tumor prevention agents can be screened in experimental animals using transplants from human tumors or tumors that arise de novo in experimental animals. Thus, agents that kill or interfere with the symmetrical or asymmetrical divisions of cells with bell-shaped nuclei in cell culture would be recognized as candidates for tumor prevention or therapy in patients.

Alternatively, anti-tumorigenic agents can be screened in vitro or ex vivo (e.g., in cultured samples where nuclear morphologies are maintained). Methods for preserving tissues in primary cultures for extended periods of time are known in the art. Anti-tumorigenic agents can be identified in cultured samples where heteromorphic nuclear morphotypes are preserved. Thus, if such a cultured sample is treated with a candidate anti-tumorigenic agent and the prevalence of heteromorphic nuclear morphotypes is diminished, then the candidate anti-tumorigenic agent would be expected to be useful in treating tumors in patients in vivo.

The invention will be further described with reference to the following non-limiting examples. The teachings of all the patents, patent applications and all other publications and websites cited herein are incorporated by reference in their entirety.

EXEMPLIFICATION

Example 1

Experimental Procedures

Sources of Cells and Tissues

All adult tissue and tumor specimens were obtained as surgical discards at the Massachusetts General Hospital through the Department of Pathology and the MGH Center for Cancer Research. Each tissue section was immediately placed in fresh ice-cold fixative and transported to the MIT cytogenetics laboratory for further analyses. Use of the anonymous discarded sections had been approved by the Institutional Review Boards of both MGH and MIT. The fetal gut sections analyzed were not obtained for this research but were drawn from the archival slide collection of the Chernobyl Scientific Expedition charged with the task of discovering signs of genetic radiation damage in developing fetuses and children after the meltdown of the nuclear reactor at Chernobyl, Ukraine in 1985. Two normal adult colons that were discarded after surgery not related to cancer (five ~2 to 10 mm diameter polyps of two FAPC colons, four colon tumors, one pancreatic tumor and several independent colorectal metastases of the liver from two patients) were analyzed.

Tissue Excision, Fixation, Spreading and DNA Staining

The procedure uses fixed and stained tissue sections some 0.5 mm in thickness in which cellular adhesions are chemically disrupted to a degree that permits an orderly spreading of tissue on a microscope slide. This technique allows for the cells to retain the structural integrity of their nuclei. Small morphological structures such as stained nuclei and larger structures such as colonic crypts may still be observed albeit with some minimal distortion inherent in tissue spreading.

Nuclear morphotypes are visible especially where the colonic surgical discards are provided soon after resection (e.g., less than an hour after resection, more preferably, about or less than 30 minutes after resection). Sheets (~1 cm$^2$) of stripped colonic mucosa or 1 mm thick sections of adenomas or adenocarcinomas were placed immediately upon dissection into freshly prepared 4° C. Carnoy's fixative (3:1, methanol:glacial acetic acid). The volume of fixative is at least three times the volume of the tissue sample. Fresh fixative is replaced three times every 45 minutes for a total of three hours of fixation. Carnoy's fixative is then replaced by 4° C. 70% methanol and may be stored up to a year at −40° C.

About 1 mm$^2$ pieces (length □ width as distinct from section thickness) are excised from the whole fixed tissue sample for spreading and DNA staining. Each piece is rinsed in distilled water and placed in 2 mL of 1 N HCl at 60° C. for precisely 8 minutes for partial hydrolysis of macromolecules and DNA depurination. The hydrolysis is terminated by a rapid rinse in cold distilled water. The rinsed sample is steeped in 45% acetic acid (room temperature) for 15 to 30 minutes. This last step is known in botanical cytogenetics as "tissue maceration" that allows subsequent tissue cell spreading and observation of plant tissue sections with gentle pressure on microscope slides (Gostev, A. and Asker, S., 1978, *Hereditas*, 101:98-104; Gostjeva, E., 1998, *Genetika*, 32:17-21). This "macerated" fixed tissue sample is used immediately for spreading on microscope slides. Each ~1 mm² macerated section is bisected to form two ~0.5 □ 1 mm pieces of fixed, macerated tissue. Each piece is transferred into ~5 μL of acetic acid on a clean microscope slide and covered with a 22 □ 22 mm cover slip. Holding the cover slip by the edges slight pressure is applied on the tissue sample to locate it in the middle of the slide.

For the spreading step, 5 layers of filter paper are folded and placed on the cover slip taking extreme care not to move the cover slip. A tweezer handle is moved steadily in one direction along the filter paper covering the cover slip with slight and even pressure. "Slight" means markedly less pressure than used in chromosome "squashes". The quality of the spreading is checked using a 20× phase-contrast objective for each individual sample. An indication of a good colonic tissue spread is that there are no damaged nuclei on the edges of the whole tissue spread while crypts are pressed into what is essentially a monolayer preserving the morphological integrity of the crypts. Each well-spread sample slide is placed immediately on a dry ice surface. In 2 minutes, when the spread tissue sample is completely frozen, a razor blade is inserted under one edge the cover slip that is gently lifted off. Slides are allowed to dry in a dust free environment for not less then one hour.

Staining procedures are performed at room temperature. Slides are placed in Coplin jars and filled with Schiff's reagent (Art. 9033, Merck) to stain the partially depurinated DNA of the nuclei. Slides are immersed in staining solution for one hour, rinsed in the same Coplin jar two times in 2□SSC (trisodium citrate 8.8 g/L, sodium chloride 17.5 g/L), once for 30 sec and once quickly. Slides are then rinsed with distilled water. The slides at this stage are suitable for observation of the distribution of DNA in nuclei including measurement of Feulgen DNA amounts in nuclei or condensed chromosomes by quantitative image analysis (Hardie, D. et al., 2002, *J. Histochem. Cytochem.*, 50:735-749).

To achieve superior resolution and imaging of interphase nuclei slides may be further stained with Giemsa. Immediately after rinsing in 2□SSC slides are placed in 1% Giemsa solution (Giemsa, Art. 9204, Merck) for 5 minutes then rinsed quickly first in Sörenssen buffer (disodium hydrogen phosphate dihydrate 11.87 g/L, potassium dihydrogen phosphate 9.07 g/L) and then distilled water. Water drops are shaken off the slide as if one were shaking a thermometer to avoid erosion of the stain. The slides are placed in a dust free environment to dry at room temperature for one hour. They are then placed in a Coplin jar filled with Xylene for at least 3 hours to remove fat. Cover slips are glued to the slides with DePex mounting media and permitted to dry for 3 hours at which time they are ready for high resolution scanning.

Microscope and Image Processing System

A KS-400 Image Analysis System™, Version 3.0, (Zeiss, Germany) was used to observe and record images for future quantitative analyses of nuclear dimensions and DNA content. The system consists of a motorized light microscope, Axioscope™, color CCD camera, AxioCam™ (Zeiss, Germany) linked to a personal computer. Images were transmitted from the microscope at $1.4/100$ magnification of the planar apochromatic objective using visible light and 560 nm (green) filter when Feulgen stain alone was employed. No filter was used when Feulgen-Giemsa staining was employed.

The frame grabber and optimal light exposure were adjusted prior to each scanning session. Nuclear images were recorded at a pixel size 0.0223 □ 0.0223 um. Scanning parameters such as magnification, resolution and light exposure were saved to permit reproducible scans of the same slide.

Example 2

Detection of Bell-Shaped Nuclei

Embryonic Hindgut

Observations described herein are from two independent embryo gut sections are shown in FIGS. 1, 2A-2C and 3A-3F. Three observations were made. First, there was the array of seven distinct nuclear morphotypes summarized in FIG. 1. Secondly there was the orderly linear head to toe arrangement of bell-shaped nuclei organized in long (~20 to 50 micron diameter) tubes as shown in FIGS. 2A-2C. Thirdly, there were the extraordinary forms of symmetrical and asymmetrical amitoses involving bell-shaped nuclei as shown in FIGS. 3A-3F.

Phase contrast images (left frame, FIG. 2B) and stained nuclear images (middle frame, FIG. 2B) of the identical hindgut section when overlaid (right frame, FIG. 2C) showed that the a linearly oriented nuclei were contained in a previously unreported tube-like structure which is itself about 20-50 microns in diameter. 280× magnification of the nuclei (middle frame, FIG. 2B) shows that these non-spherical nuclei appear to be in the form of cups or bells. Higher resolution images (1400×) of nuclei in linear array shows them to have a reproducible bell shape that is apparently hollow. The "head to toe" orientation of the bells was preserved in all embryonic tubes observed but tubes snake backwards and forwards such that parallel tubes may have locally anti-parallel orientation of bell-shaped nuclei.

Figure 3A:
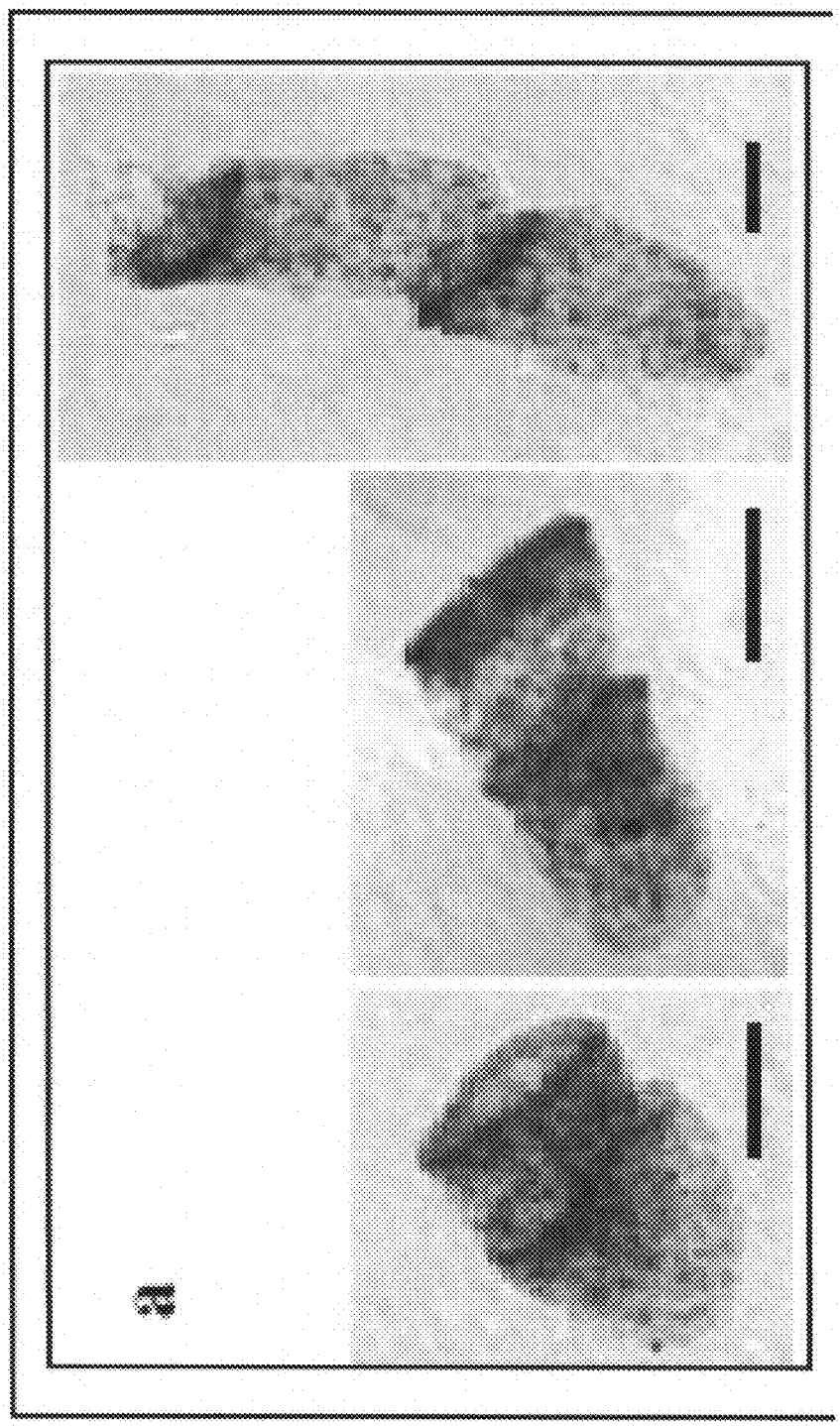
FIGS. 3A-3F show amitoses of bell-shaped nuclei embryonic gut.
Figure 3B:
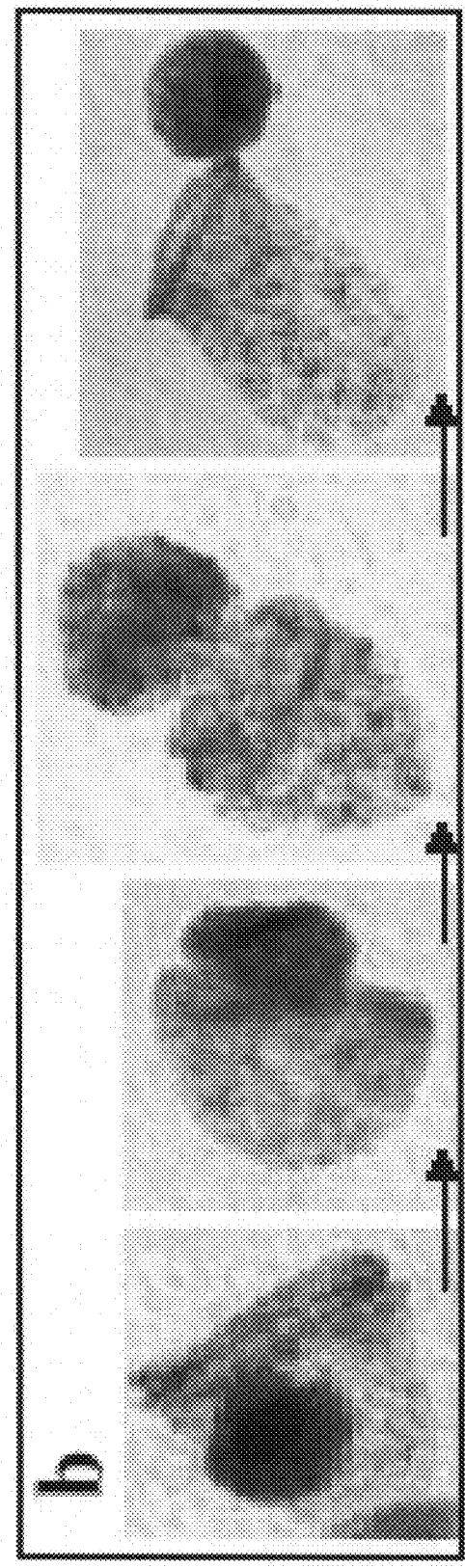

Bell-shaped nuclei were observed undergoing symmetrical or asymmetrical amitoses only within the tube-like structures. Symmetrical amitoses of bell-shaped nuclei resembled a simple separation of two stacked paper cups. At the highest resolution, the upper lip of these bells-in-division appeared to have a pair of condensed or partially condensed chromatids (see FIG. 1, arrows) encircling perhaps ¾ths of the bell's outer rim, as seen in FIGS. 3A and 3B. A variety of different bell shapes were found within the various tubes and these morphological variations were faithfully reproduced in symmetrical amitoses, FIG. 3A.

Figure 3C:
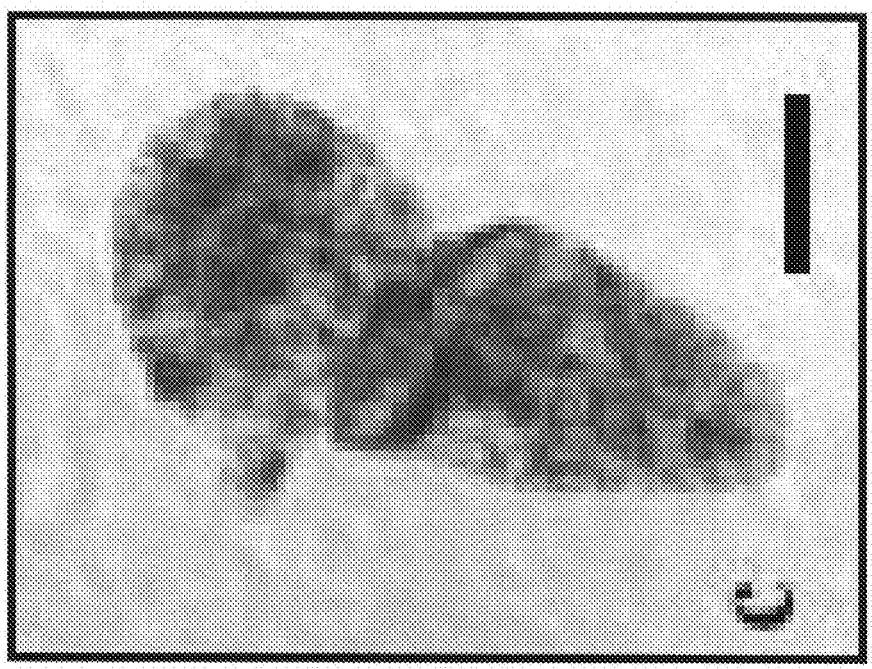
Figure 3D:
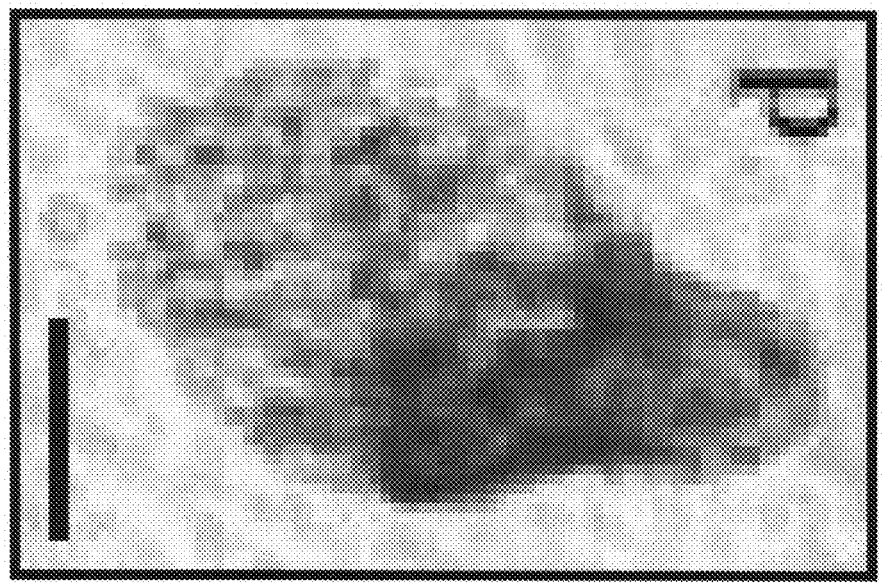
Figure 3E:
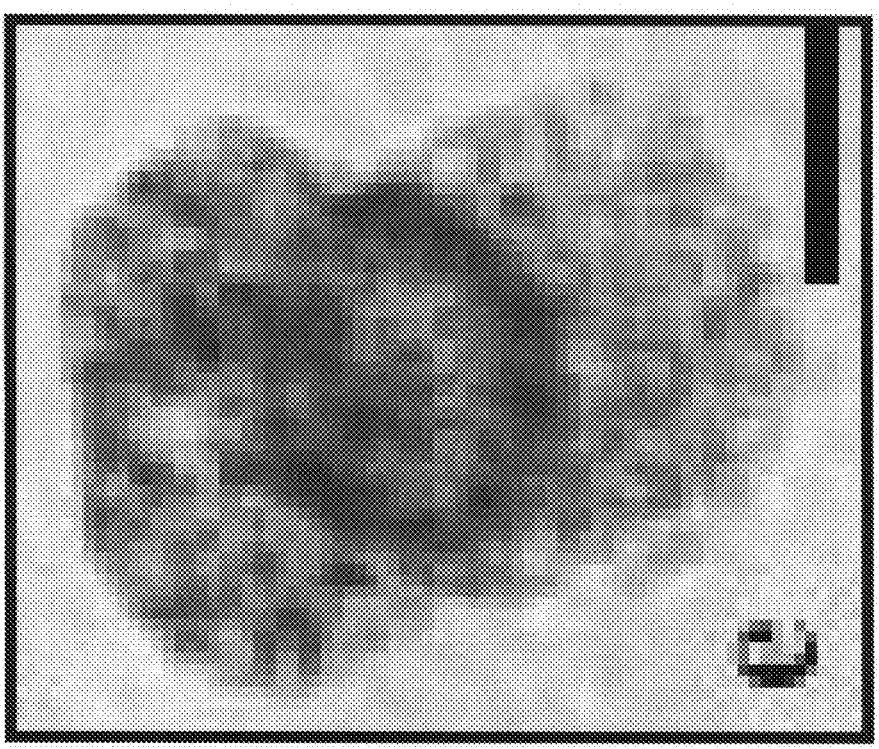
Figure 3F:
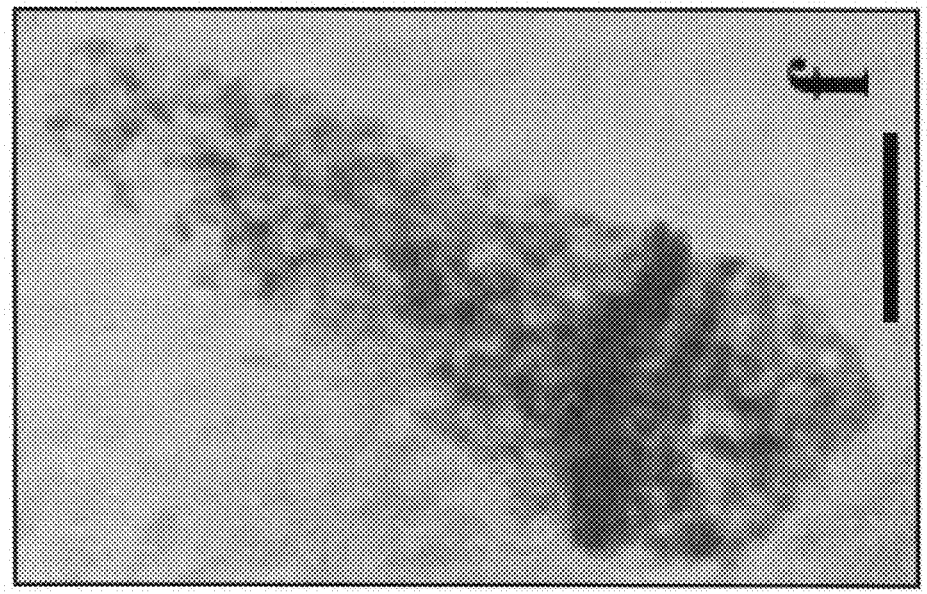
Figure 4A:
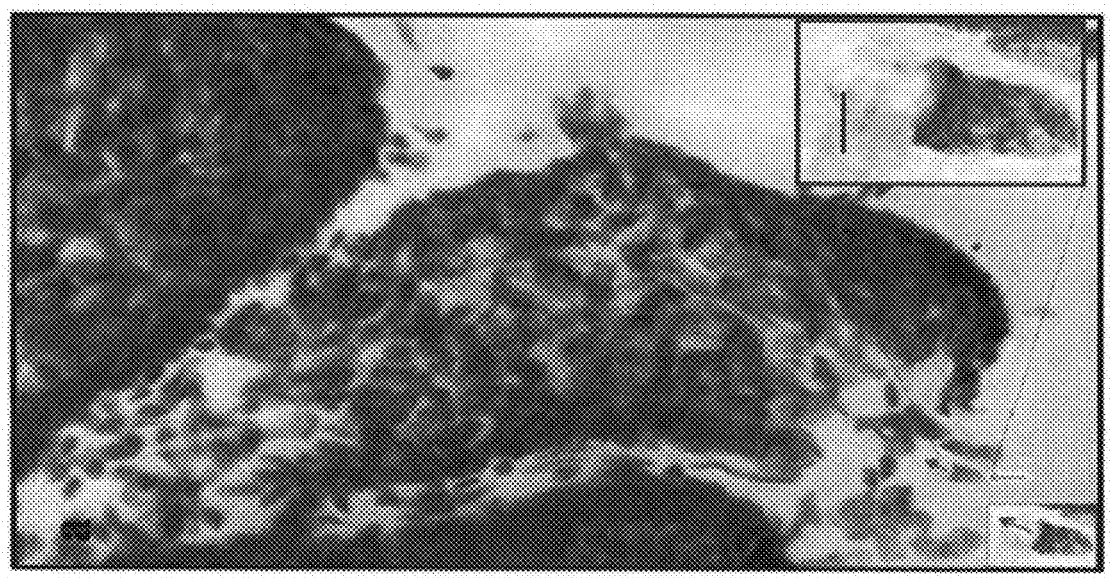
FIGS. 4A-4C show normal adult colonic crypts.
Figure 4B:
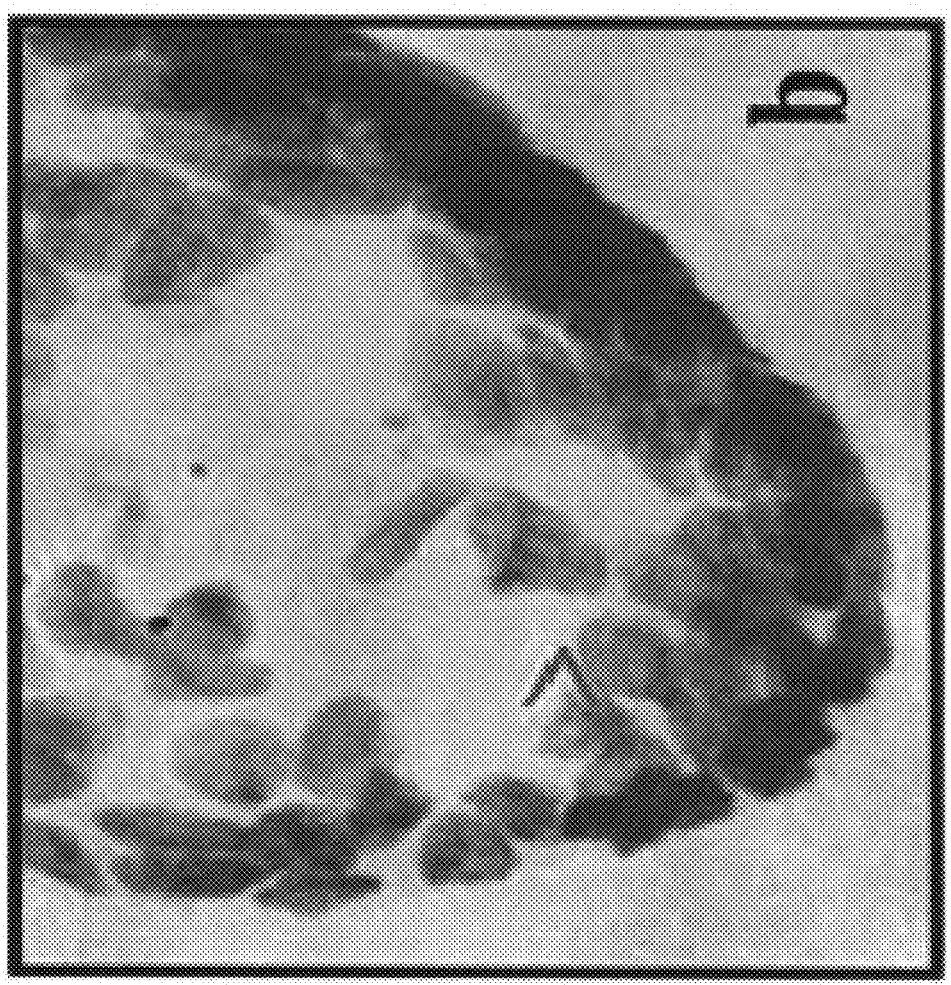
Figure 4C:
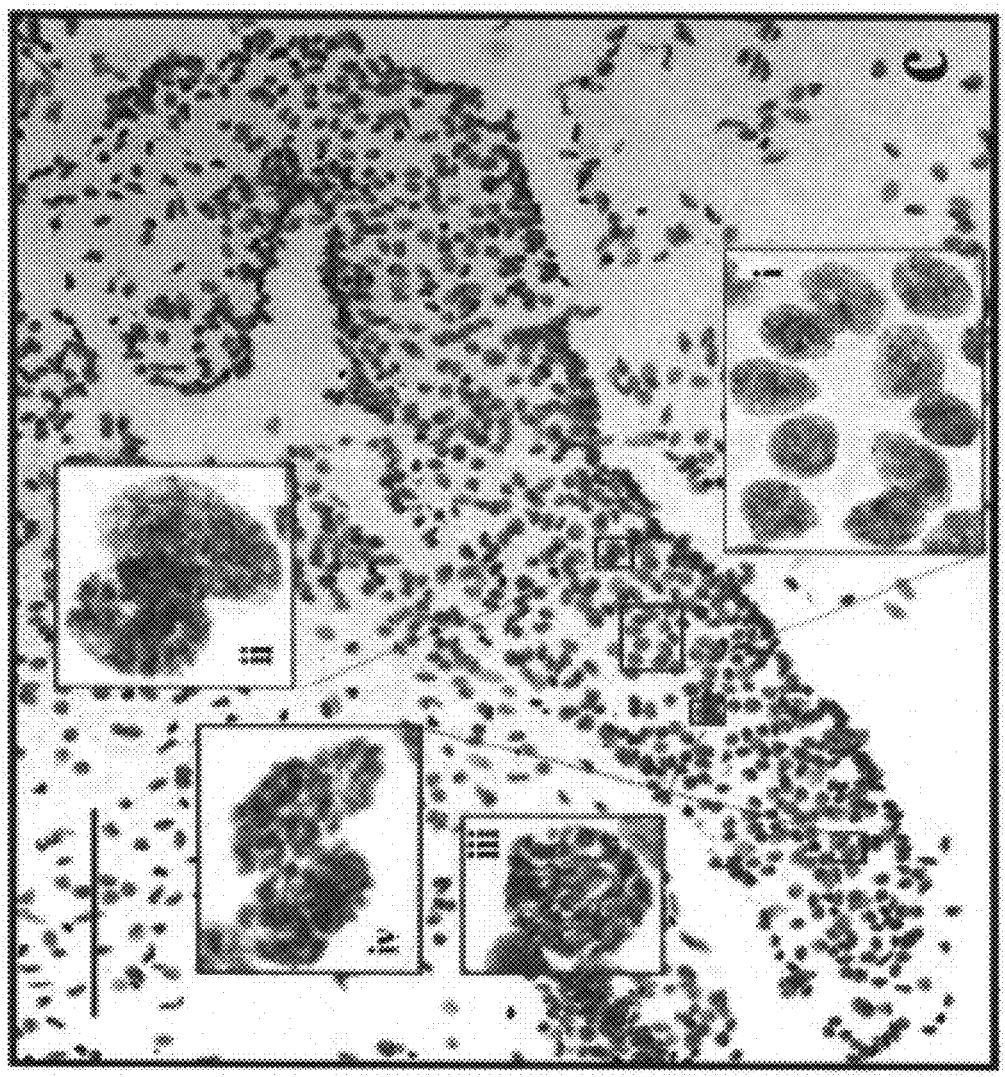

This previously undiscovered form of amitotic nuclear division of bell-shaped nuclei was, of course, surprising. But the fetal sections had more surprises than this. Throughout the gut sections bell-shaped nuclei within tubular structures were found apparently "giving birth" to nuclei. Examples of every form of nuclear shape found in the fetal sections and shown in FIG. 1 were found emerging from bell-shaped nuclei. These extraordinary amitotic asymmetrical forms of nuclear division are shown in FIG. 3C.

With regard to the nuclear morphotypes other than bell-shaped, all appeared to undergo mitoses forming local colonies of identical nuclear morphotypes. These mitotic divisions always occurred outside of the long tubes containing bell-shaped nuclei. Curiously, the specific nuclear morphology was preserved in prophase, and even recreated by association of the chromosomes in late anatelophases, as is also shown in FIG. 1.

Normal Colonic Epithelium

The combination of ~0.5 mm sections, the tissue maceration (see below) and gentle spreading combined with the DNA-specific staining to create particularly clear images of nuclei permitted recognition of three dimensional features. All, or nearly all, nuclei in crypts could be observed from the crypt base to the luminal surface. Many crypts either fractured or spread in such a way that individual nuclear shapes could be discerned. Cells with ovoid or spheroid nuclei line the crypt from just above the base to the epithelial extension into the lumen. However, in the first ~25 cells of the crypt base itself a nuclear morphotype that may be characterized as "discoid" (~2-3 microns thick and ~10 microns diameter) predominated. In less than 1% of crypt bases in which the cells were well separated a bell-shaped nucleus was discerned among the discoid nuclei. A similar low frequency of bell-shaped nuclei has been observed in preparations of adult liver. In an adult colon without any indication of neoplasia or pre-neoplasia no other nuclear morphological variant was observed in a cell by cell scan of about 800 well spread crypts.

Adenomas

Figure 5A:
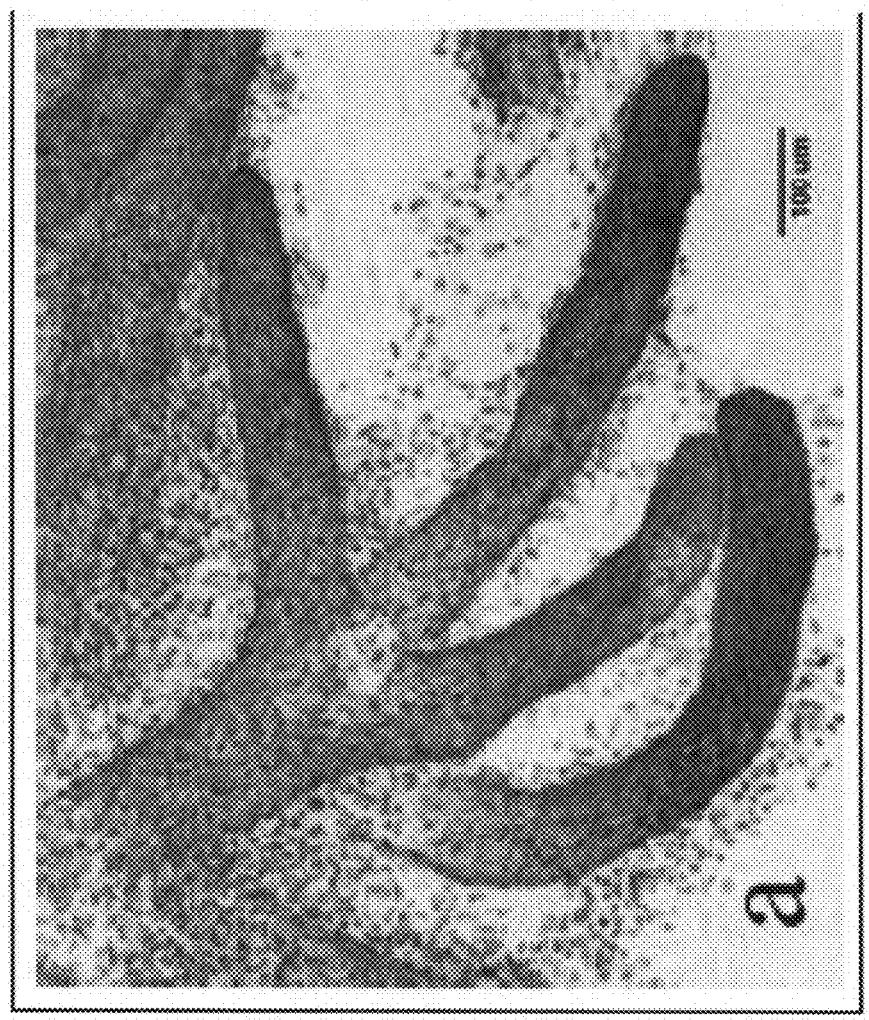
FIGS. 5A-5E show enlarged images of adenomas.
Figure 5B:
Figure 5C:
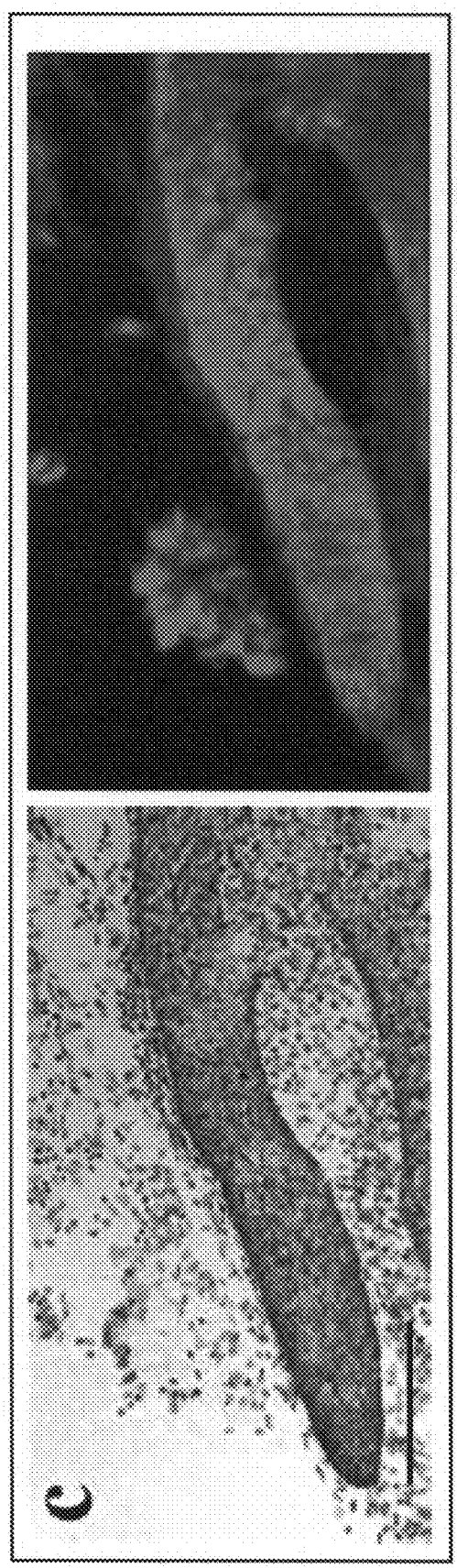
Figure 5D:
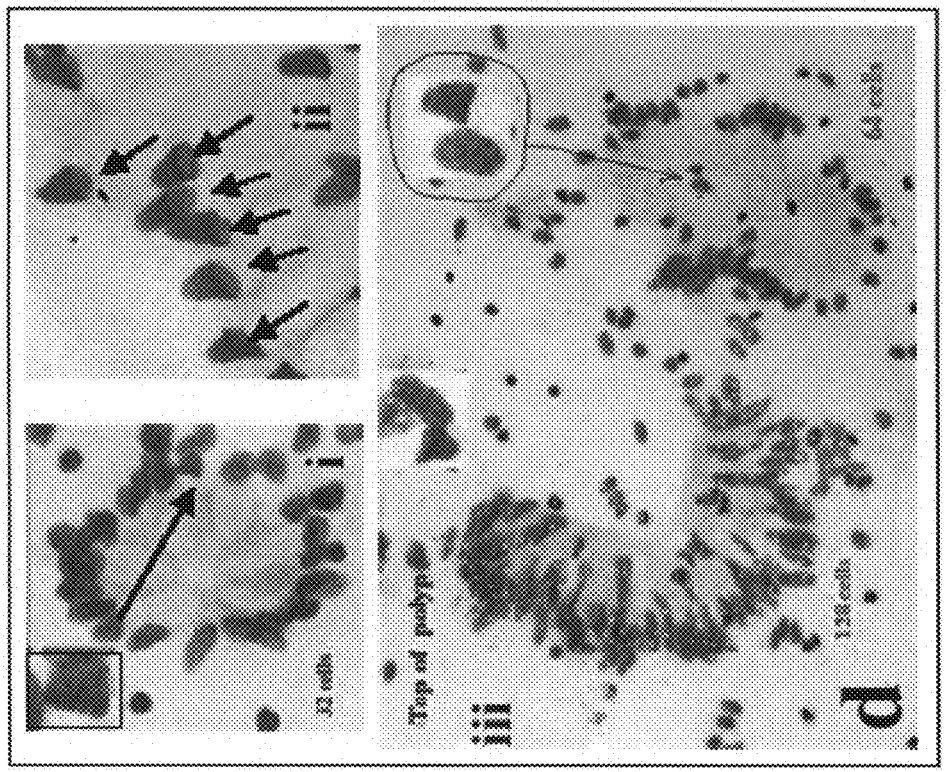
Figure 5E:
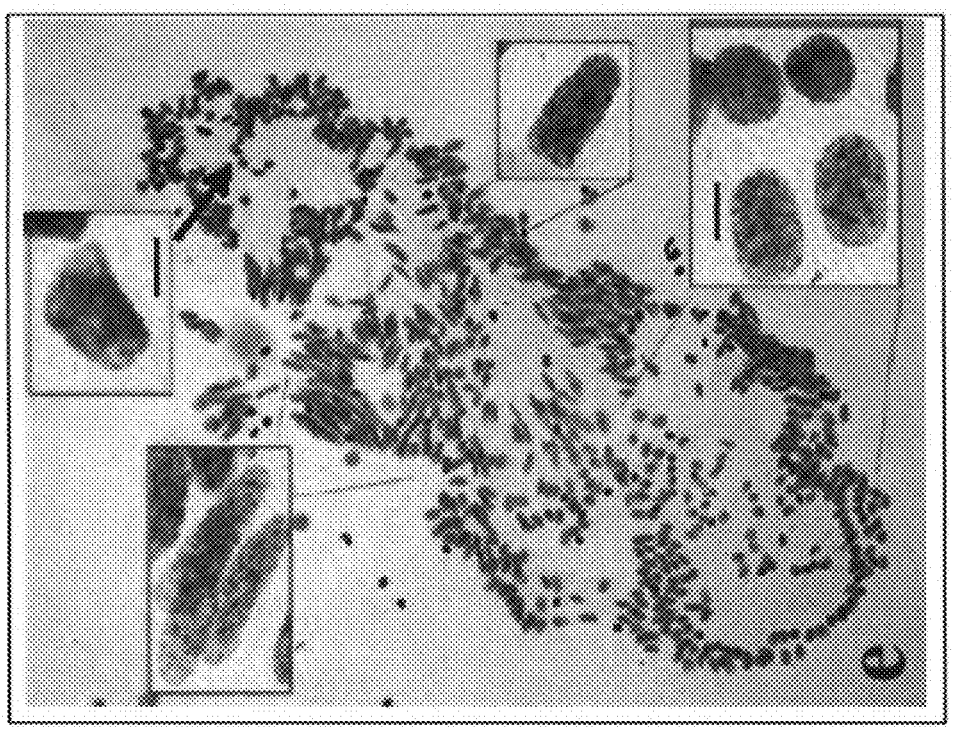

The adenomas contained many crypts, indistinguishable from normal colonic crypts, each with ~2000 cells. These were frequently found in branching forms as shown in FIG. 5A. The same spheroid and ovoid nuclei were present in the crypt walls, as in the normal colonic crypts, but frequently displayed one or two bell-shaped nuclei in the crypt base. Irregular crypt-like structures were also observed containing up to ~8000 cells, which were more easily spread by tissue maceration (FIG. 5B). In addition, many diverse cells and groups were interspersed among the crypts and crypt-like structures (FIG. 5C). Some structures appeared to be growing toward full-sized normal crypts containing ~250, ~500 or ~1000 cells (The spreading technique employed generally permitted exact cell counts in structures of up to several hundred cells.). Many cell groups were seen as "rings" of exactly 8, 16, 32, 64 and 128 cells each. (FIG. 5D). Higher magnification examination revealed that while most of the cells of the walls of the crypt-like structures had spherical or oval nuclei as in the normal adult colonic crypt, colonies of cells with either oval, cigar-shaped or bullet-shaped nuclei appeared at crypt wall breaches. Colonies with oval and cigar-shaped nuclei had been observed in fetal gut but the "bullet-shaped" nuclear morphotype was seen only in adenomas and adenocarcinomas (FIG. 5E).

The "bullet-shaped" nuclear morphotype also appeared to arise from bell-shaped nuclei by asymmetrical amitoses with the irregular end ("bitten off") emerging first. Small colonies of cells with bullet-shaped nuclei were seen and these colonies contained cells undergoing ordinary mitoses save for the interesting fact that the curious nuclear morphology was retained from early prophase through anatelophase.

While rare in the normal adult colon the bell-shaped nuclei were obviously playing an important role in adenomas. They appeared in a number of adenoma contexts. Some were found as one to ten or more "bells" in the spaces among the crypt-like structures as shown in FIG. 5D. Others were found as single "bells" in multicellular ring structures in which one bell nucleus was always seen in the ring with 2n−1 cells of spherical or other morphology as in FIGS. 5C and 5D. In the smaller to full-sized structures that cohered under spreading conditions as did normal colonic crypts, bell-shaped nuclei appeared as single bells, more often as a pair of bells or occasionally 4 or 8 bells within the crypt-like structures basal cup. In the much larger irregular crypt-like structures, bell-shaped nuclei were anatomically integrated into the walls of the aberrant structures mixed with cells of other nuclear morphologies. It appeared as if these larger irregular crypt-like structures were mosaics of multiple different kinds of clusters each with it's own nuclear morphotype.

The bell-shaped nuclei of the adenomas differed in another remarkable way from the other nuclear morphotypes and from bell-shaped nuclei in embryos: though just more than a thousand bell-shaped nuclei have been observed in individual adenomas not a single bell-shaped nucleus in any adenoma has been observed in the symmetrical amitotic form found in fetal sections. It is also notable that no bell-shaped nucleus in a condition that could be described as pyknotic was observed among the adenomas scanned. Nuclei of all other morphological forms were frequently found in mitosis or pyknosis at roughly equal frequencies (about 1-5/1000 total nuclei) when whole sections were scanned. Small subsections varied greatly with regard to mitotic and pyknotic counts. As used herein, "pyknotic" refers to a condition of nuclear rupture and chromatin condensation in irregular clumps that is indicative of a dying cell.

Adenocarcinomas

Figure 6A:
FIGS. 6A-6C show enlarged images of adenocarcinomas.
Figure 6B:
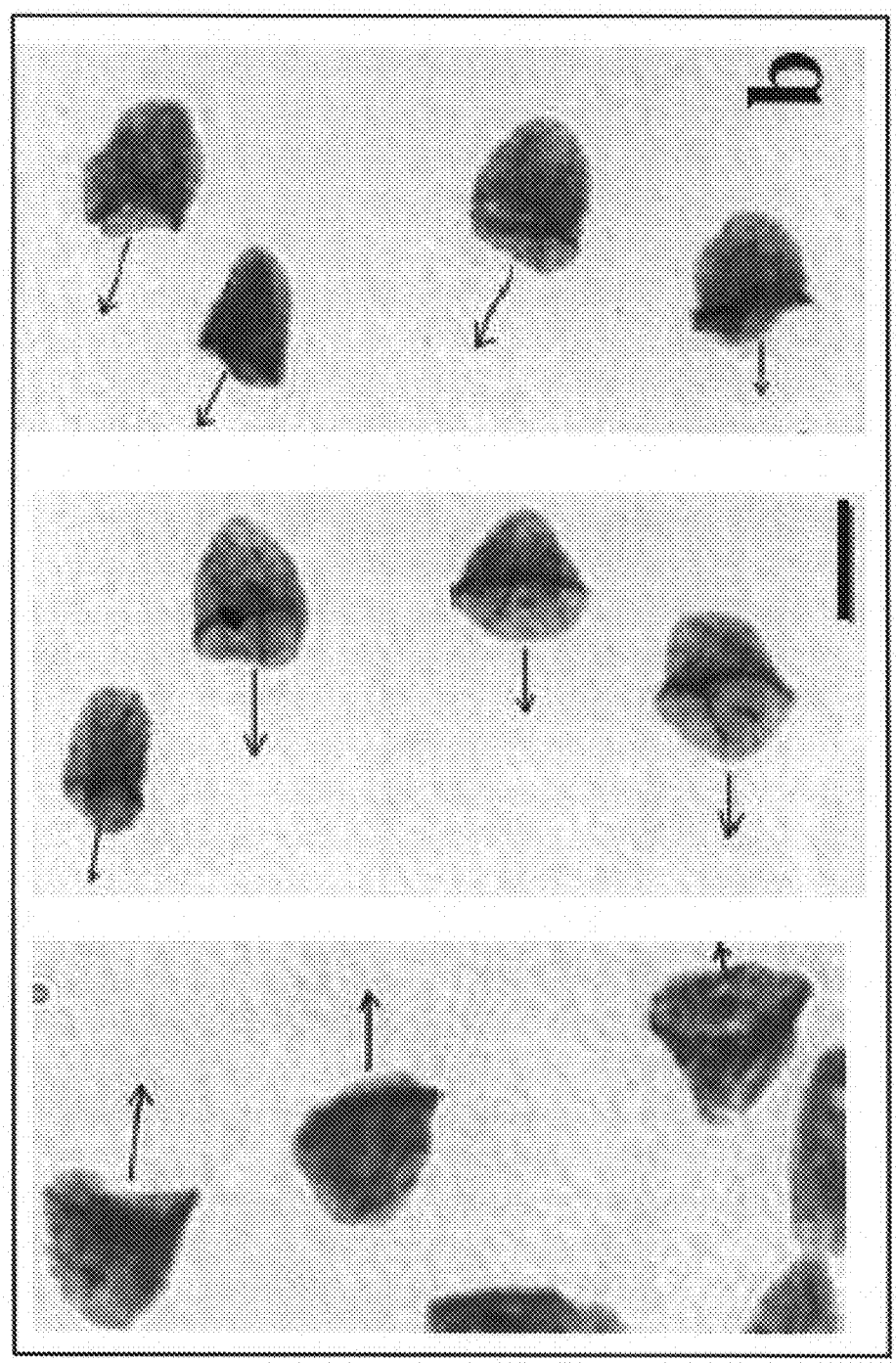
Figure 6C:
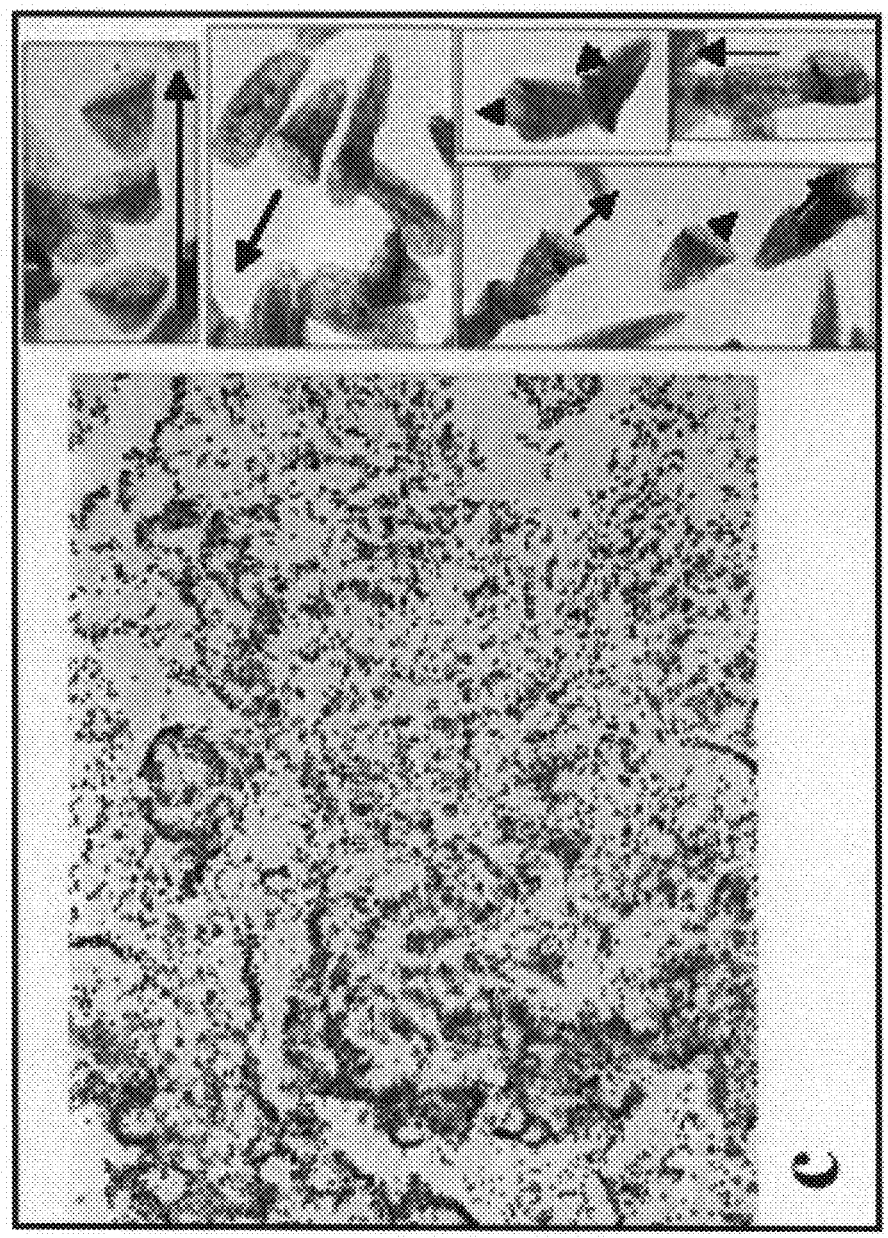
Figure 7A:
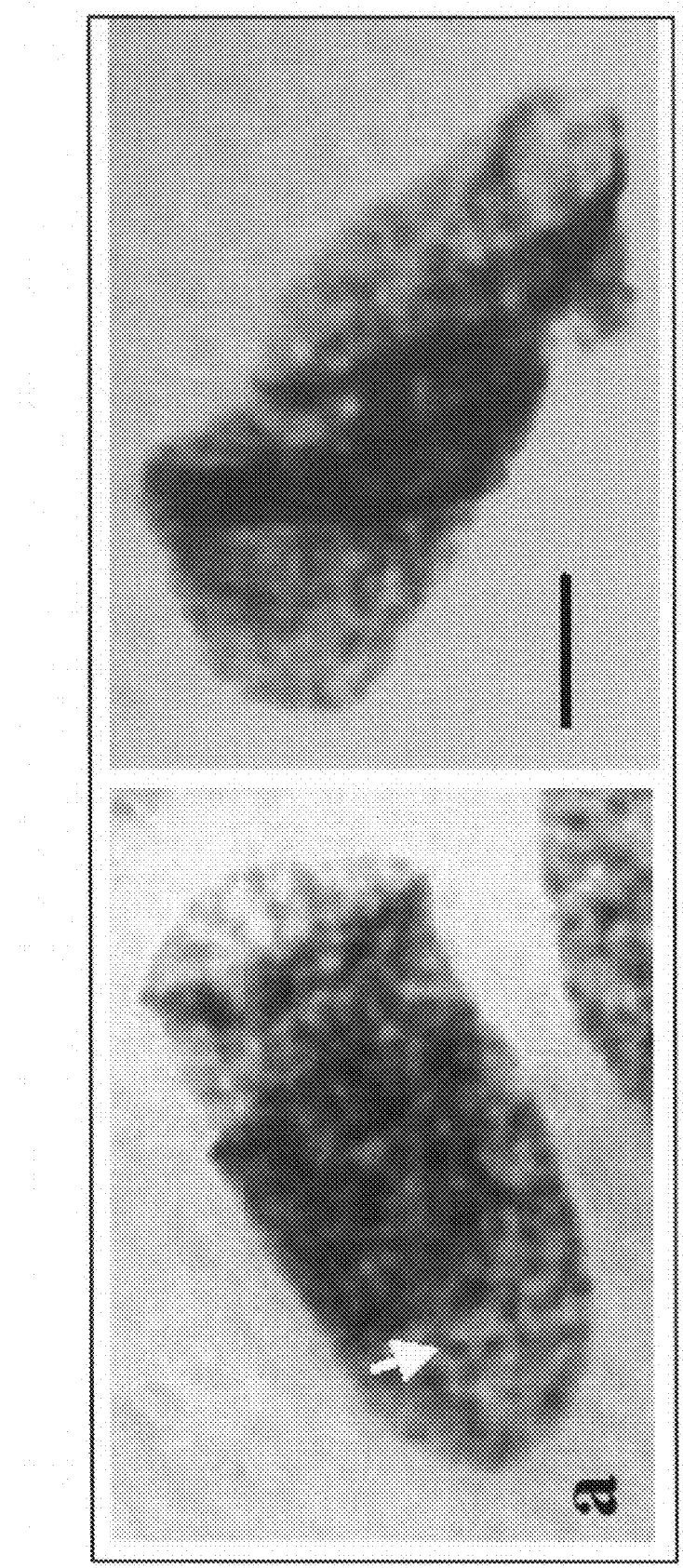
Figure 7B:
Figure 7C:
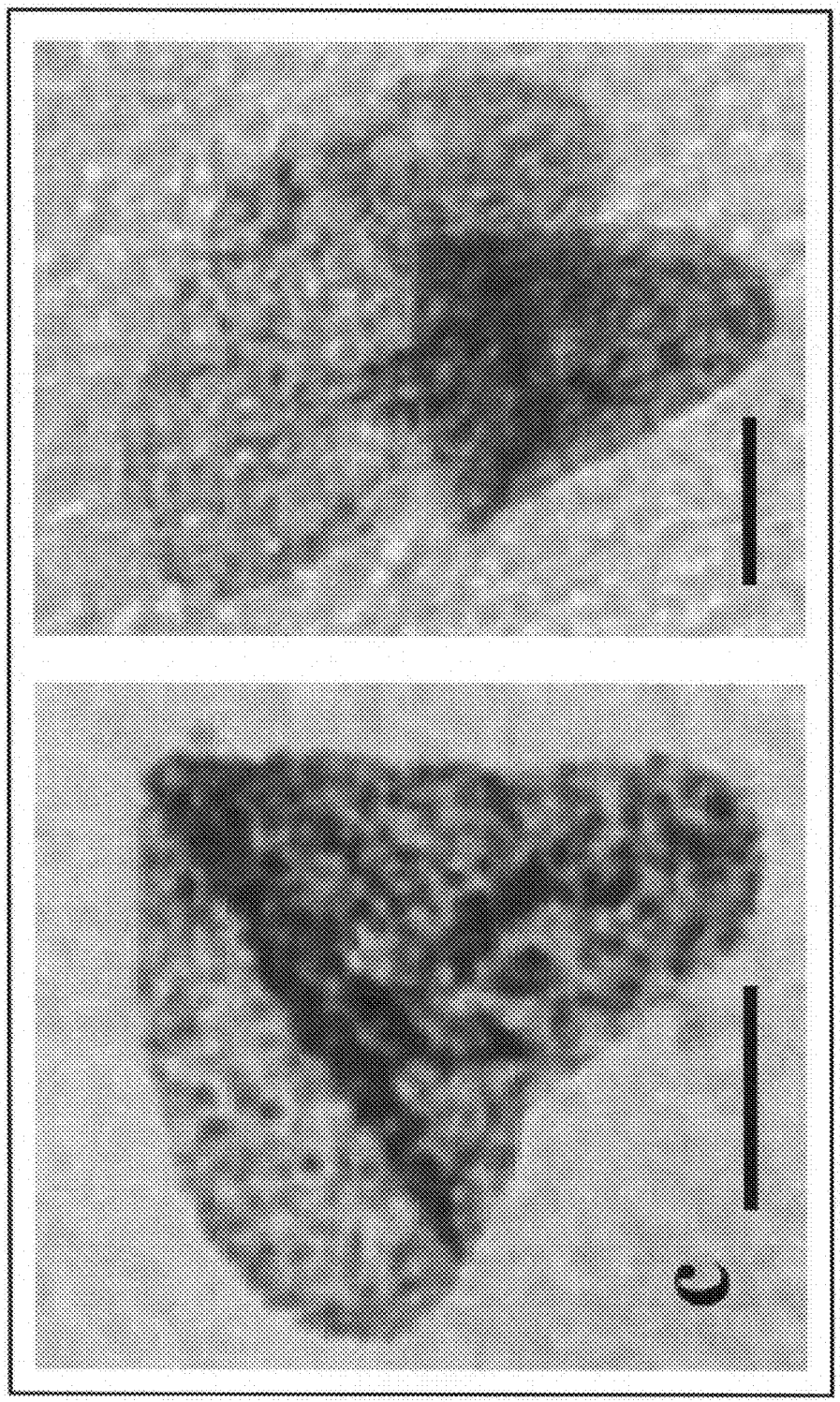
Figure 7E:
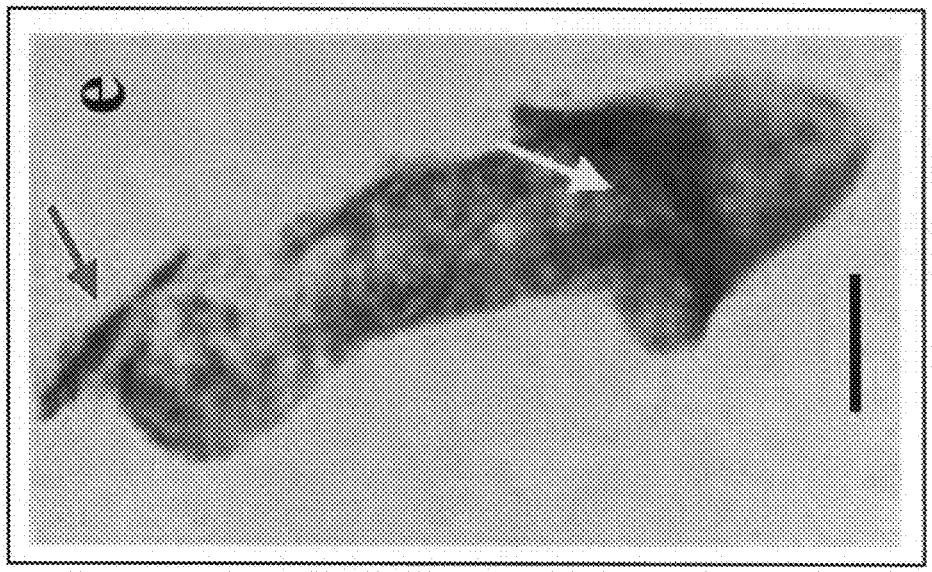

While adenocarcinomas had much greater masses and many individual sections resisted spreading by gentle pressure, the admixture of crypts, larger irregular crypt-like structures and inter-crypt presence of rings of 16, 32, 64 and 128 cells was essentially the same as in the much smaller adenomas. Breaches in the walls of the crypt-like structures were associated with colonies of cells with identical nuclear morphologies persisting into the three dimensional distributions of condensed prophase chromosomes. Bell-shaped nuclei were still found as singlets, pairs or larger numbers in the basal cup of crypts and embedded in complex whorls in the walls of the larger aberrant crypt-like structures. FIGS. 6A-6C show a series of these bell-shaped nuclei all typical of what is seen in adenocarcinomas. The set of nuclear morphotypes in the adenocarcinomas appear to be identical with the set seen in adenomas. In particular the "bullet-shaped" nuclear morphotype not observed in fetal sections or adult colons was frequently observed.

A discernible difference between adenomas and adenocarcinomas was that the orientation of the crypt-like structures was haphazard with base to lumen directions apparently randomly oriented with regard to the tumor surface. Also crypts and irregular crypt-like structures were not found frequently in the tumor interior, which may be better characterized as an eclectic but not chaotic collection of smaller, locally organized structures. It is possible that these interspersed colonies of cells with different nuclear forms represent a symbiotic community.

An important characteristic by which the adenocarcinomas differed from adenomas was the frequent appearance of apparently organized groupings of hundreds of bell-shaped nuclei, many of which were frequently (~1%) involved in symmetrical amitoses. At low magnification these appeared in the spaces among crypt-like structures and looked like a spider web or leaf vein skeleton. At higher magnification the thin "veins" were found to be partially ordered strands of cells with bell-shaped nuclei having the curious characteristic of having their "mouths" oriented in the same direction, 90° from the axis: the shoulder-to-shoulder orientation (FIG. 6C). Furthermore, scanning through multiple sections of adenocarcinomas uncovered bell-shaped nuclei in the "head-to-toe" orientation observed in the fetal gut but not in the adenomas. These linearly arrayed nuclei were also encased in the tubular structure (syncytium) seen in the fetus. An occasional pyknotic figure that might have been a bell-shaped nucleus was observed but at a much lower frequency than symmetrical amitoses among bell-shaped nuclei.

Further Observations

Metastases of colorectal tumors in the liver recreate the pattern of nuclear morphotypes, crypts and crypt-like structures seemingly indistinguishable from adenocarcinomas. Scanning sections of sections of adult human liver has revealed occasional bell-shaped nuclei as were observed in adult colonic crypts. Scans of adult mouse colons similarly revealed cells with bell-shaped nuclei in crypt bases as in adult humans. In a potentially important observation for growth and study of cultured cells with bell-shaped nuclei, a low frequency, ~1/10,000 cells, have been found in mouse cell cultures in which stem-like behavior has been postulated and studied with regard to symmetrical and symmetrical cell division kinetics (Sherley, J. et al., 1995, *Proc. Natl. Acad. Sci USA*, 92:136-140; Merok, J. et al., 2002, *Cancer Res.*, 62:6791-6795).

Example 3

Post-embryonic organizing stem cells of the fetal colon were specifically identified by an opened-mouth, bell-shaped nuclear morphotype. These peculiar nuclei undergo both symmetric and asymmetric nuclear fission without general chromosome condensation. Nuclear fissions drive net growth and differentiation throughout fetal, neonatal and juvenile life before a final metamorphosis into adult maintenance stem cells. These bell-shaped nuclear morphotypes are rarely found in adult colonic crypt bases but reappear prominently in preneoplasia and neoplasia and appear to drive net growth and differentiation in colon adenomas, adenocarcinomas and metastases.

Combining these observations with inferences derived from analyses of historical age-specific colorectal cancer rates, present day age-specific colonic adenoma prevalence and direct measurements of genetic change in human tissues suggests a default hypothesis for late-onset carcinogenesis in the colon and perhaps other sites: oncomutations required for tumor initiation occur at markedly higher rates in juvenile stem cells than in adult maintenance stem cells because of their peculiar DNA biochemistry and mode of segregation. The higher juvenile mutation rates have the effect of limiting tumor initiation events to the juvenile years. Initiated juvenile stem cells continue to create local patches of juvenile tissue eventually observed in the colon as polyps and these cells maintain the "mutator" phenotype imputed to juvenile cells. Additional oncomutation(s) and/or local biochemical conditions during the slow but inexorable growth of the preneoplastic colony switch one of the preneoplastic "juvenile" stem cells to a fetal stem cell phenotype that rapidly creates a lethal tumor mass.

Organogenesis

The idea that organogenesis is accomplished by a linear cascade of stem cells capable of net growth by self propagation in symmetrical divisions and responsible for differentiation by asymmetric divisions giving rise to a stem cell and an alternate cellular form is generally held by developmental biologists. Confusion arises when attempts are made to differentiate the identities and functions of the various forms and potentials of cells from the early embryonic stem cells of the blastocyst capable of giving rise to viable embryos on transplantation and stem cells such as those isolated from the bone marrow of animals capable of repopulating an hematopoietic system and possibly other organs. Adult stem cells or maintenance stem cells are posited to be responsible for repopulation of the many tissue elements that turn over in organs such as the colon. In adults one may imagine small depositories of stem cells capable of repopulating tissues and organs on demand. One can also imagine a different form of adult maintenance stem cell that defines clonal turnover units by intermittent asymmetrical divisions that produce an initial transition cell that is lost by subsequent binary divisions to secondary transition cells up to differentiated terminal cells.

Disclosed herein are structures containing easily identifiable nuclear forms that appear to undergo both symmetric and asymmetric nuclear fission. These forms are identified by their bell-shaped nuclear morphotypes that comprise some 30% of all nuclei of human gut in 5-7 week fetuses but are found in the basal apex in somewhat less than 1% of adult colonic crypts.

Carcinogenesis

The idea that carcinogenesis is accomplished by a linear cascade of stem cells capable of net growth by self propagation in symmetrical divisions and responsible for differentiation by asymmetric divisions to create the heterogeneity evidenced in adenocarcinomas is less widely held. The concept of carcinogenesis as "loss of cellular control" accompanied by seemingly random expression of genes such as those expressed in early embryogenesis is fairly widespread. However, dilution and transplantation experiments, similar to those demonstrating the physical existence of organ restoring stem cells in hemoleukopoiesis have established the existence of a very small fraction of tumor cells having the ability to give rise to a growing tumor containing a variety of cell types. These practical demonstrations of the existence of tumor stem cells requires reflection on the idea of cancer as a highly degenerate state and probing the possibility that it, like organogenesis, is the expression of specific changes that define a pathway from normal stem cells to tumor stem cells. Relevant to this line of thought is the finding of bell-shaped nuclei identical to those found in colonic embryogenesis in both colonic polyps (adenomas, preneoplastic lesions) and tumors (adenocarcinomas, neoplasia) and subsequent metastases. Preliminary enumeration of these nuclear forms and their frequency of symmetrical nuclear divisions permit comparison to the expected low division rates of preneoplasia and rapid division of neoplasia.

Relationship of Stem Cell Biology to Age-Specific Cancer Rates.

It is reasonable to infer the hypothesis that initiated stem cells grow at near juvenile rates to form a preneoplastic colony (adenoma, polyp) from which inexorably emerged a neoplastic stem cell that grows at near fetal rates to form a lethal tumor. The hypothesis that neoplasia is a re-expression of the fetal phenotype is not original with us being ascribed to mid 19$^{th}$ century pathologists such as Cohnheim (1875, Virchows Arch., 65:64; 1877-1880, Vorelesungen uber allgemeine Pathologie. Ein Handbuch fur Artzte und Studierende. Berlin, Hirchswald 1-2 691S). The hypothesis arises that preneoplasia, adenomas or polyps in the human colon is a simple continuation of the phenotype of the juvenile colon.

Data and derived inferences about the growth rate of preneoplasia were augmented by a fortuitous discovery about the growth rates of children's weights as a function of age: male and female juveniles increase in average mass exponentially with a doubling time of about 6 years from about 1.5 years to 14.5 years in females and to 16.5 years in males. The growth rate during these age intervals is 0.158 for males, 0.167 for females. Relating the growth rate of the colon to that of body mass required modeling of the surface area of a cylinder inside a growing sphere that would increase as the mass$^{2/3}$ or in this case, ~0.16$^{2/3}$~0.11, a value equal to that estimated for the colonic preneoplastic growth rate.

As the estimated growth rates of preneoplastic lesions of the colon are about equal to the estimated growth rate of the juvenile colon, the hypothesis developed that preneoplasia in some way recreated conditions of juvenile growth (Herrero-Jimenez et al., 2000). As net growth of juvenile stem cells would presumably be required for juvenile tissue growth, the idea arose that adenomas, which contain many of the histological attributes of organized colon, might in fact be equivalent to patches of juvenile tissue expansion in a background of non-growing adult crypts. This hypothesis has been tested by computations limiting the age of initiation to the age of maximum body mass and found that it is indeed possible to derive sets of parameters that accord with the age-specific colorectal cancer rates if the process of initiation is limited to the juvenile period. Indeed parameters can be derived that fit the cancer rate data if initiation is limited to age five or lower. Such calculations demonstrate that the hypothesis of limitation of initiation to within the juvenile period is consistent with the age-specific cancer rate data but do not, however, demonstrate the hypothesis' validity.

Age-Specific Detection of Adenomas.

These theoretical constructs would remain in the domain of untestable hypotheses were it not for an important set of clinical observations that seem to bear directly on the hypothesis that tumor initiation is bounded by the juvenile period. In studies designed to define the optimal age and number of proctoscopic examinations to detect and remove potentially neoplastic colonic adenomas, the fraction of persons with adenomas detectable by flexible sigmoidoscopy was found to reach a stable maximum at about sixty years of age. When observations by proctologists with consistently high records of adenomas detection were analyzed, ~15% of males and some ~10% of females had somewhat more than one adenoma on average. From these clinical data, it is reasonable to infer: first, the slowly growing preneoplastic adenomas must have had their origins far earlier in life than age sixty (with a growth rate of 0.11 a tissue stem cell initiated at age 1 would have increased to only $2^7=128$ preneoplastic stem cells by age 63. The number of total cells in such an adenoma would be much larger on the order of a million total cells); second, the similarity between the fraction of males with polyps, ~15%, and the estimated minimum fraction of males (1890s cohort) at lifetime risk of colon cancer, 18-20%, suggests that the individuals with adenomas at age sixty and those at lifetime risk may be identical (if this inference is confirmed on further analysis it would be important for two reasons: (a) it would eliminate any role for inherited or genetic risk factors in the eventual transformation of preneoplastic lesions into neoplastic lesions in the colon, and (b) it would eliminate any important role for competing forms of mortality with risk factors shared with colorectal cancer); third, the appearance of an average of more than one polyp in persons with polyps implies the male population consists of a subpopulation of some 20% in whom tumor initiation and preneoplastic growth occur and a separate distinct subpopulation of some 80% in which either tumor initiation and/or preneoplastic growth do not occur; fourth, insofar as calculations of preneoplastic growth rates in males and females yield identical results, the male/female ratio of persons with polyps over age sixty with polyps and the gender differences in the average number of polyps/individual with polyps permits the hypothesis that gender differences in cancer rates may be ascribed entirely to the number of initiated colonic stem cells created through the initiation susceptible juvenile or pre-juvenile years (for instance, if oncomutation rates were the same in males and females, the ratio of expected preneoplastic colonies created in the juvenile years would simply be the ratio of stem cell years experienced up to maturation at about 14.5 years in females and 16.5 years in males).

Histopathology.

Throughout the $20^{th}$ century, molecular, biochemical and histolopathological analytical methods have been applied in parallel but independent studies of tumors and embryos. Rich and extensive data obtained showed that many normal ontogenic characteristics associated with the growth and development of humans re-appear much later in life as abnormal pathological growth that is cancers. At the beginning of $21^{st}$ century scientists put forward the hypothesis that similarity between embryos and tumors (both monoclonal in origin, both appearing in explicit heterogeneity of cells populations) can be explained from a single point, that is the very specific cell such as a stem cell, can give rise to a whole embryo, organs and tissues of an embryo as well as of a large tumor.

Table 1 shows the stem cells hierarchy in early human development. Between gestational age of 2 weeks (the stage of blastocyst and gastrulation) and 5-12 weeks (the stage of organogenesis) there is a cascade of stem cells arising to correspond to each particular stage of early fetal development.

TABLE 1

Table 1. The hierarchy of stem cells arising through ontogenesis and through 'blocking' and-'reversing' mutagenesis of a stem cell to become a cancer stem cell.

| Ontogenesis | | | | | |
|---|---|---|---|---|---|
| Fertilized egg | Blastocyst | Elaboration of a body plan<br>Development of pre-organ structures | Fetal organ analagen ↓<br>Neonatal organ →<br>growth and development | Juvenile growth<br>→ | Adult tissues maintenance |
| → | →<br>Embryonic stem cells | →<br>Stem cells of organogenesis | →<br>Fetal stem cells | →<br>Juvenile stem cells | Adult stem cells |
| Carcinogenesis | | | | | |
| | → | → | → | | |
| | Embryonic stem cell | Stem cell of organogenesis | Fetal stem cell | Juvenile stem cell | Initiated stem cell: juvenile stem cell blocked in transition |
| | Embryonal teratocarcinoma | Metastatic adeoncarcinoma | Adenocarcinoma | Adenoma | Single cell gives rise to a mutated clone |

The importance of distinguishing among ontogenetically different stem cells has come from the disclosed cytogenetic evaluations of human fetal and adult tissues.

Embryonic stem cells of epiblast are the cells that are not committed to anything in pre-implanted embryo, divide by mitosis and their nuclei are simply spherical in shape. They have no evidence of retainable polarity of the cell, nor of the nucleus. At the stage of elaboration of a body plan and organogenesis the cells acquire the polarity thought to be necessary to start spatially 'directed' migration of cells and cell layers to create bilaterally symmetrical body of a human, to outline positions of internal organs in a body cavity.

Figure 8:
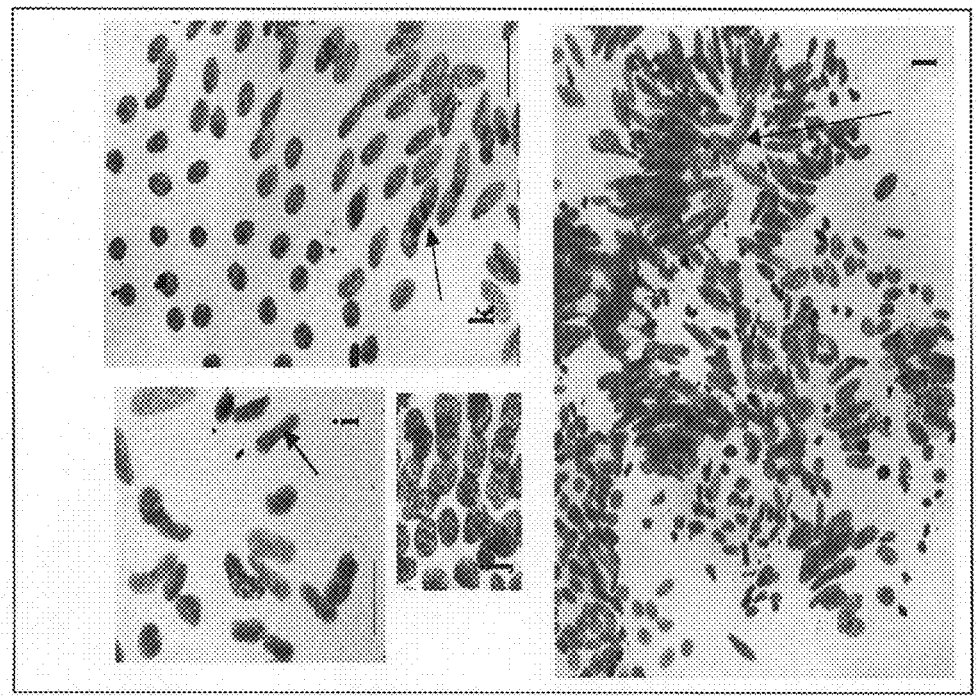
FIG. 8 shows Feulgen-DNA stained nuclei of human colonic epithelium: a, b: the bell-shaped nuclei of gut; c: of colon adenoma; d: symmetrical nuclear fission of the bell-shaped nucleus in gut; e: asymmetrical nuclear division; f: asymmetrical nuclear fission (condensed spherical nucleus emerges from the bell-shaped nucleus) in colon adenocarcinoma; g: bell-shaped nuclei at the bottom of normal looking crypts (arrowed) and h: throughout 'incipient' crypt of adenoma; i: diversity of nuclei morphotypes in gut. The 'cigar'-shaped nuclei arrowed in cell spreads obtained from adenoma (k) and colon adenocarcinoma (l). In 'j' the nuclei of spherical shape, typical for adult normal colonic crypts, are shown. The bar size is 5 μm.
Figure 8:
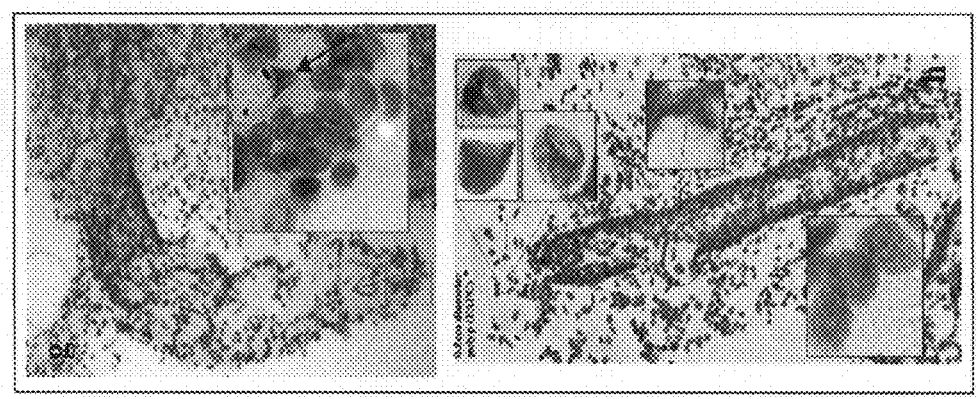
Figure 8:
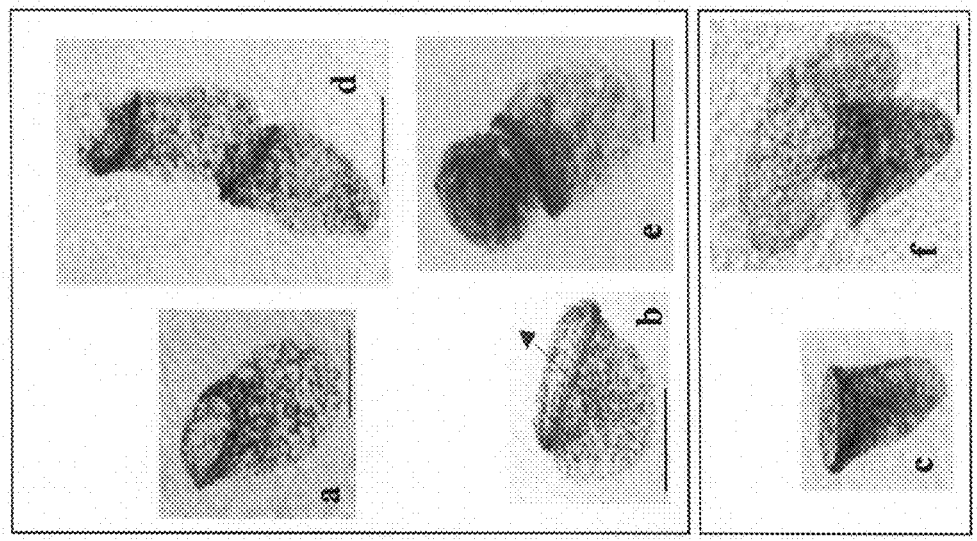

The middle stage of organogenesis of a gut (5-7 weeks), from which all major parts of a digestive system will arise, includes cells comprising nuclei that are not just spherical but have diverse nuclear morphotypes. Nuclei of some of the cells have distinct polarity and divide not by mitosis but by the process more associated with "cup-from-cup" nuclear fission (FIG. 8). This particular observation has led to the conclusion that the stem cells of organogenesis could be quite different from that observed in blastomeres of an embryo.

In postnatal growth of a child and later of a juvenile the epithelial tissue continue to grow by multiplication of the stem cell to increase the number of turnover units per organ, and the number of cells per turnover unit until both features reach an organ-specific size maintained throughout life of an adult. For this matter, the stem cells taking over the growth and function of organs in juveniles should be distinguished from the stem cells of fetal growth and development as juvenile stem cells. Embryonic, fetal and adult stem cells are different in their capacity: embryonic stem cells are capable of creating the whole organ or tissue by combining different cell lineages (pluripotency), while the adult stem cells can only give rise to a 'tissue-committed' specific cells of a turnover units (multipotency).

If Sell's hypothesis of a 'relationship between the stage of differentiation of cancer stem cells and type of tumors' is correct, the ability to identify a single stem cell in it's 'adult', 'juvenile', 'fetal' or 'embryonic' form would be a significant breakthrough in the analysis of quantitative and qualitative characteristics of cancers (Sell, S., 2004. *Crit. Rev. Oncol. Hematol.*, 51:1-28). Technical tools to identify and collect a pure population of same type stem cells in a test tube are clearly useful.

Nuclei in the cells of developing fetal gut can be organized as a hollow bells (FIG. 8: a,b). Not only the cells with such nuclei are present at ~30% in the fetal gut but they have a very peculiar arrangement pattern in the gut tissue: nuclei are oriented in one direction as "bell upon the bell". They are also enclosed in the structures resembling tubular syncytia. In the normal crypts of adult colonic epithelium the cells with bell-shaped nuclei are rare and, if they are present, their number is not more than one per crypt. The cells with the same bell-shaped nuclei appear in adenomas in larger numbers, in every crypt, normal or aberrant one (see FIG. 8: g,h) and then re-appear at high frequency in aberrant crypts and tumor masses of adenocarcinomas (see Table 1).

Cells with bell-shaped nuclei are observed in large numbers in fetuses, are rare in normal adult colon free of neoplasia, present, in small numbers (<1000) in adenomas of a few cubic millimeters and large numbers (>1,000,000) in adenocarcinomas of several cubic centimeters.

An argument that these cells could be stem cells have been supported by another, also unusual, observations of bell-shaped nuclei divisions. Within the tubular syncytia the bell-shaped nuclei were giving rise to amazingly identical 3D copy of themselves, as if a Xerox™ copy of a 'template' object. All stages of consequential separation of the bell-shaped nuclei (as a separation of a two paper cups), referred to herein as 'nuclear fission' because of the absence of nuclear condensation to form mitotic chromosomes and typical mitotic apparatus, have been detected (FIG. 8: d). This finding has been followed by the observations of all seven nuclear morphotypes previously found in developing human gut (FIG. 8: e,i) as emerging from the bell-shaped nuclear, always in one direction: out of the 'mouth' of the bell. Cells with different nuclear morphotypes are phenotypically different and one can expect to detect the difference in gene expression and protein synthesis profiles between the cells with different nuclear morphotype.

The cells of an embryonic blastomere do not contain nuclei shaped as hollow bells; they have spherical nuclei and they are "embryonic stem cells". At the same time the hollow bell-shaped nuclei are already observed as early as ~5 weeks of gestation. The next stage in human life after fetal gut development where cells with bell-shaped nuclei reappear in large quantities is a pathological condition of adult colon: colon adenoma. An explicit diversity of nuclear morphotypes is also observable in colon tumors, very similar to one in fetal colon. The cells and nuclear morphotypes diversity is another reflection of cells 'heterogeneity' in tumors. Tumors are also characterized by histopathologists as containing immature cells. At different stages in developing of a tumor a single juvenile stem cell in pre-neoplasia and a single fetal stem cell in neoplasia can contribute to heterogeneous phenotype of both but with different fractions of immature cells (Table 2).

TABLE 2

Stem cells and their qualities in embryogenesis and carcinogenesis as observed in histopathological specimens of a colon.

| Stem cell qualities | In fetal 5-7 weeks gut | Adult normal tissue | Pre-neoplastic lesion (adenoma) | Adenocarcinoma |
| --- | --- | --- | --- | --- |
| Differentiation status | The stem cells of organogenesis. | The adult stem cells | The juvenile stem cell | The stem cell of organogenesis |
| Tissue, organ specific number | High fraction (up to 30% in 5 weeks gut) | Low (~4 □ $10^{-5}$) | Low but not as low as in normal epithelium (~2-4 □ $10^{-3}$) | Relatively high (mean value ~0.2%) |
| Net growth rate | Expansion of different cells types in organogenesis | Maintenance of specific cells in adult crypt | First clonal appearance of the cells 'of | Multiple clones of cells morphologically |

TABLE 2-continued

Stem cells and their qualities in embryogenesis and carcinogenesis as observed in histopathological specimens of a colon.

| Stem cell qualities | In fetal 5-7 weeks gut | Adult normal tissue | Pre-neoplastic lesion (adenoma) | Adenocarcinoma |
|---|---|---|---|---|
| | | | fetal gut' type | resembling those of fetal gut. |
| Multiplication and self-renewal by symmetric division | Frequently observed in fetal gut | Not observed | Not observed | Observed but more rare then asymmetrical types of divisions |
| Giving rise to a a different cell lineages (asymmetric division) | Frequently observed in fetal gut | Not observed | Infrequent asymmetrical divisions observed | More frequent asymmetrical divisions observed |
| Cell and/or nuclear polarity | Distinct polarity of the nuclear is observable | The nuclei in crypts niches have 'single way' orientation | Orientation of the nuclei can differ throughout crypts | Probably defines an 'inward' invasive tumor's growth |

Example 4

Described herein are methods to characterize nuclear structures, DNA content and the spatial distribution of chromosomes in bell-shaped nuclei of cells and syncytia by quantitative image cytometry and/or confocal microscopy. These methods allow for the discovery of DNA content and/or chromosome distribution vary among bell-shaped nuclei of differing morphology, tumor type (colonic vs. pancreatic) and niches within tumors. They also allow for the characterization of the progress of DNA synthesis and presence of proteins associated with mitosis in bell-shaped nuclei during symmetrical and the several forms of asymmetrical nuclear fission.

Also described herein are methods useful in isolating cells and syncytia with bell-shaped nuclei as homogeneous samples. Such methods include the use of "catapult" pressure activated laser micro-dissection to create samples of cells homogeneous for nuclear morphology that may be applied to analyses of metabolites and macromolecules. The methods for isolating single cells allow for the discovery of means to recognize nuclear morphology in unfixed tumor preparations so that homogeneous preparations of live cells and syncytia with bell-shaped nuclei can be studied ex vivo. Live bell-shaped nuclei or cells containing them could then be studied to better understand their peculiar DNA synthetic and segregation mechanisms and suggest means to interfere with these processes in cancer therapies.

Described herein is an exploration of how bell-shaped nuclei are spatially organized, how chromatin is dispersed in the nuclei, whether or not specific chromosomes occupy specific territories throughout the interior of nuclear lamina might suggest more specific therapeutic targets research and provide additional understanding of the relationship between nuclear morphotype (shape) and gene expression. Such exploration can be performed by existing methods of immunocytochemistry, molecular biology and related sciences.

Figure 9:
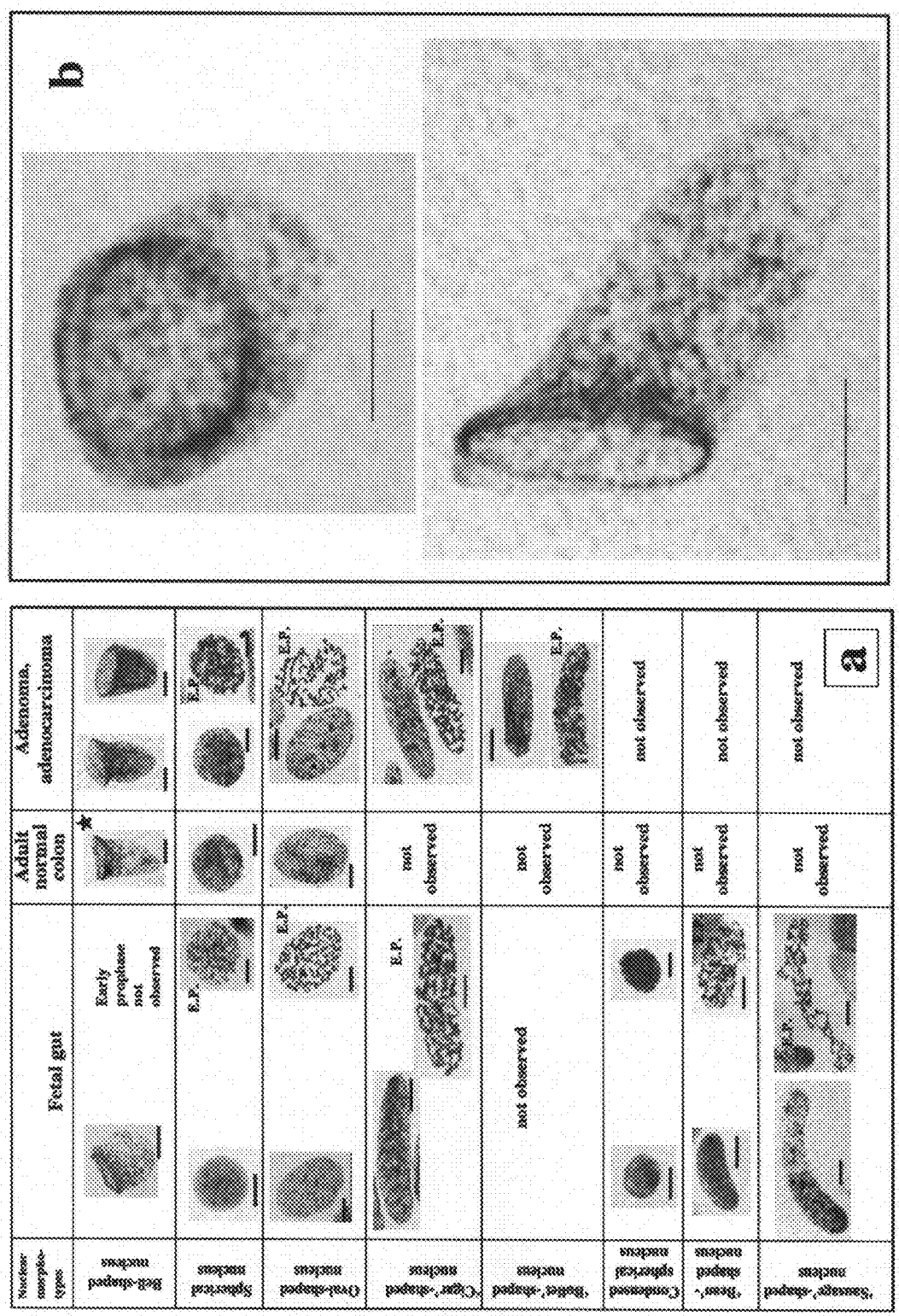
FIG. 9 shows a summary of key images. (a) Examples of nuclear morphotypes observed in interphase and early prophase (E.P.) cells in human fetal gut, normal colonic mucosa, adenomas and adenocarcinomas. (H-Bell-shaped nuclei are rarely observed in adult colon). (b) High resolution image (1400×) of bell-shaped nuclei of fetal gut. Condensed DNA appears to create an anulus that maintains an opening into the hollow bell structure. Scale bar, 5 μm.
Figure 10:
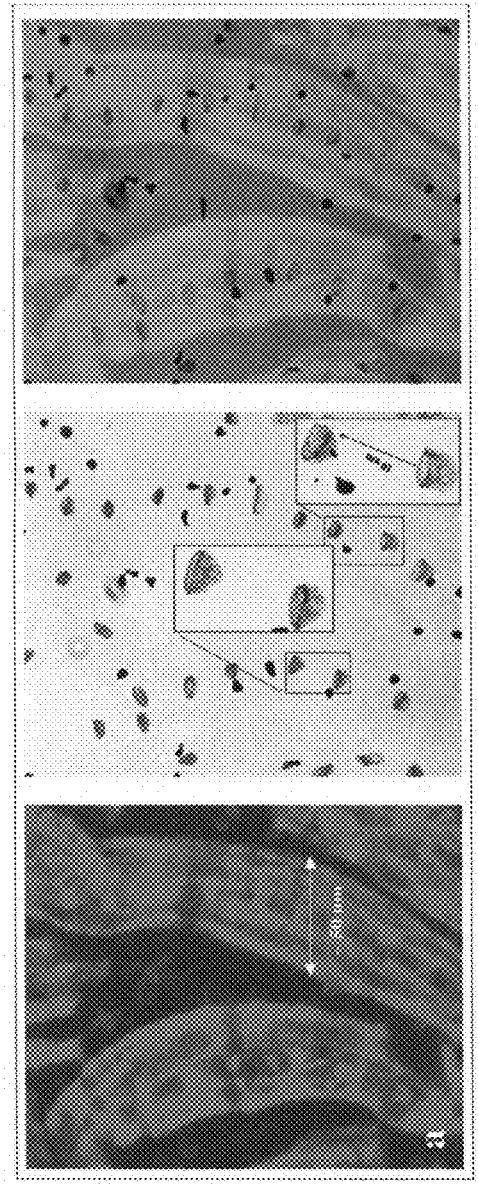
FIG. 10 shows sections of embryonic gut, 5-7 weeks: (a) Phase contrast image (left frame) and stained nuclei image (middle) and the merged image (right) show the linear arrays of nuclei within ~50 micron diameter tubular syncytium; (b) High resolution image of the nuclei shows hollow bell-shaped structures. The 'head to toe' orientation of the bells is preserved in all embryonic tubes observed but tubes snake backwards and forwards such that parallel tubes may have locally anti-parallel bell-shaped nuclei orientation. Scale bars, 50 μm at low and 5 μm at high magnification.
Figure 10:
Figure 11:
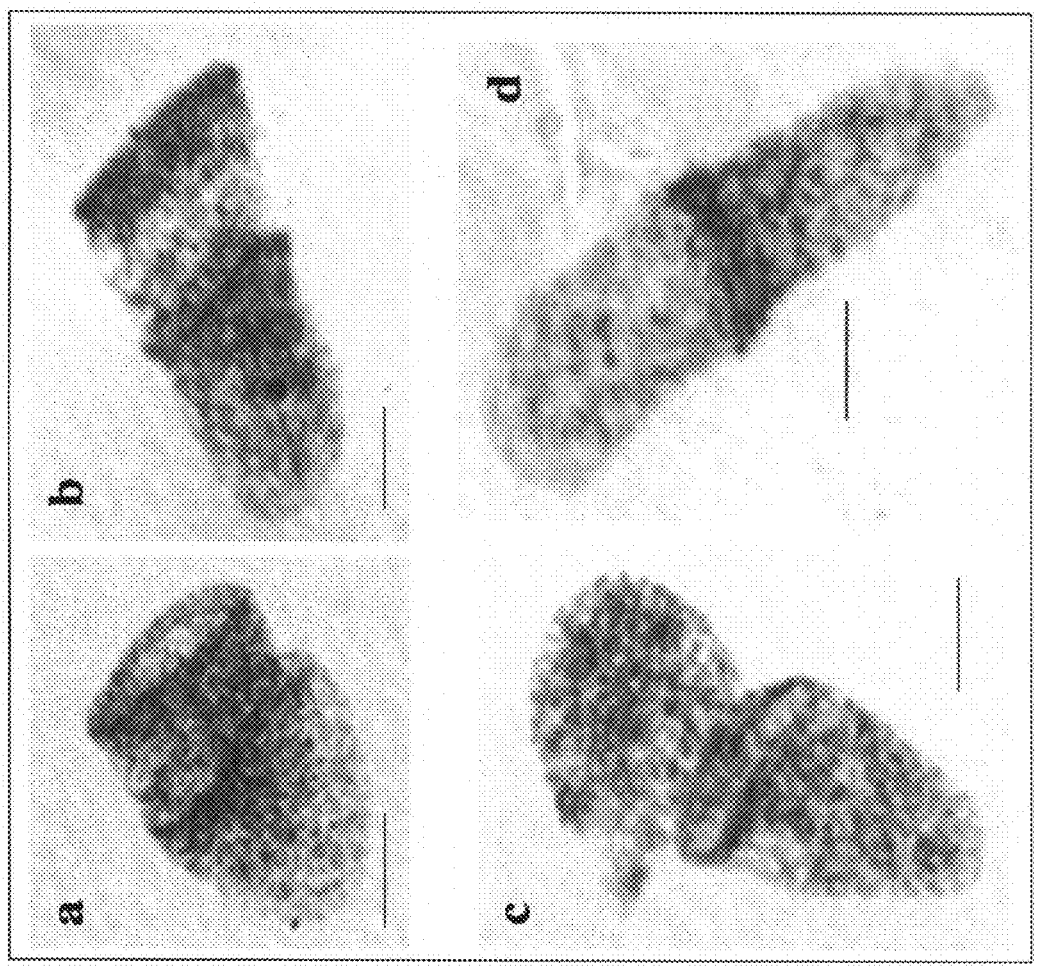
FIG. 11 shows nuclear fission of bell-shaped nuclei in fetal gut. a,b: Symmetrical nuclear fission: bell-shaped nuclei emerges from bell-shaped nuclei of similar shape. c,d: Asymmetrical nuclear fission: a spherical nucleus, and a cigar-shaped nuclei emerging from a bell-shaped nucleus. Scale bar, 5 μm.
Figure 12:
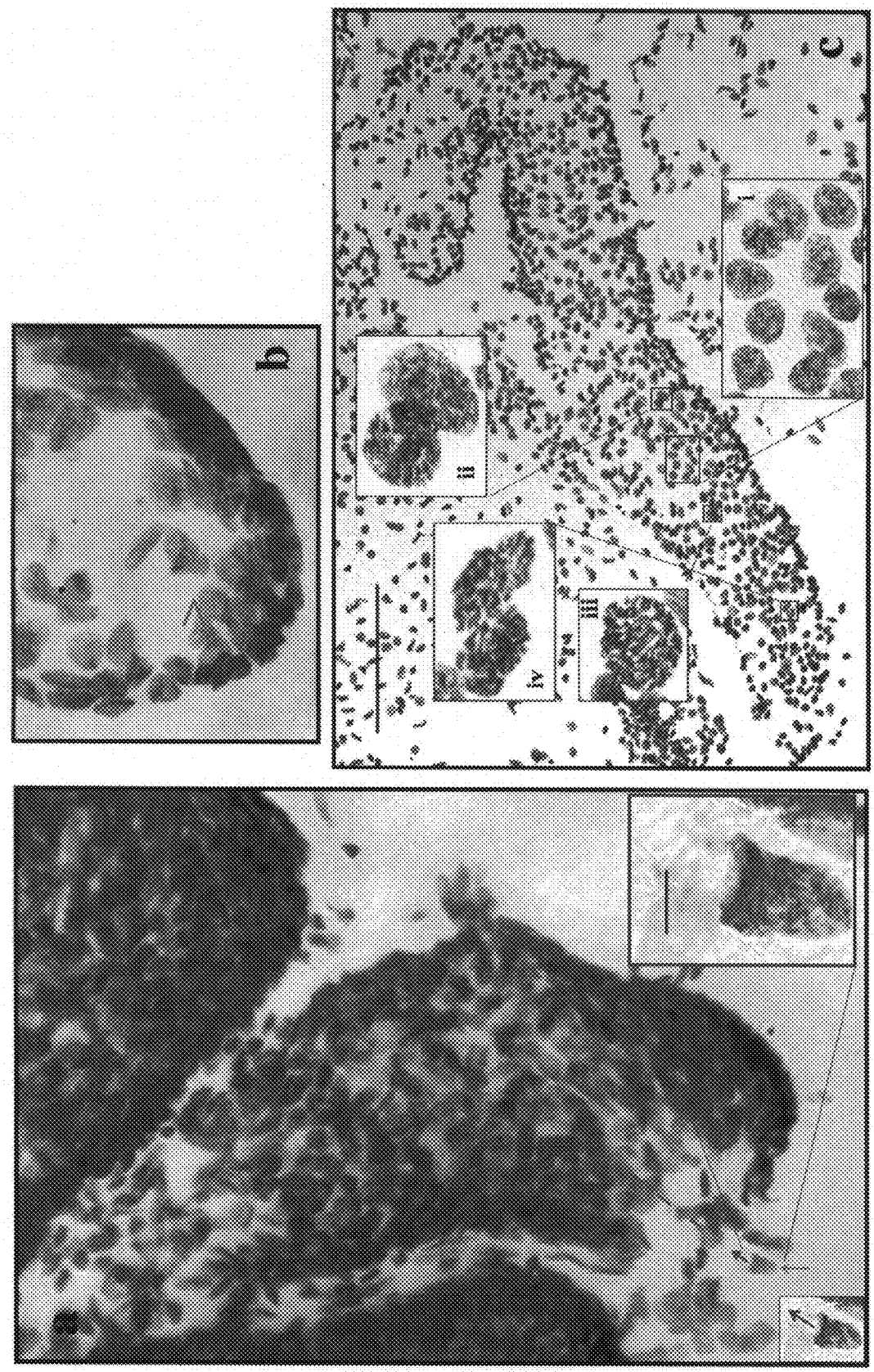
FIG. 12 shows normal adult colonic crypts: (a) Crypts of about 2000 spheroid, spherical or discoid nuclei occasionally (<1/100) contained a recognizable bell-shaped nucleus [arrow] located at the bottom of the crypt; (b) Crypt base showing another bell-shaped nucleus; (c) Morphotypes of interphase and mitotic nuclei of the walls and luminal surface in a well-spread crypt. The enlarged images show: [i] spherical and oval interphase nuclei, [ii, iii] early prophases of spherical- and oval-shaped nuclei, and [iv] an ana-telophase nucleus. Scale bars, 100 μm for low and 5 μm for high magnification images.
Figure 13:
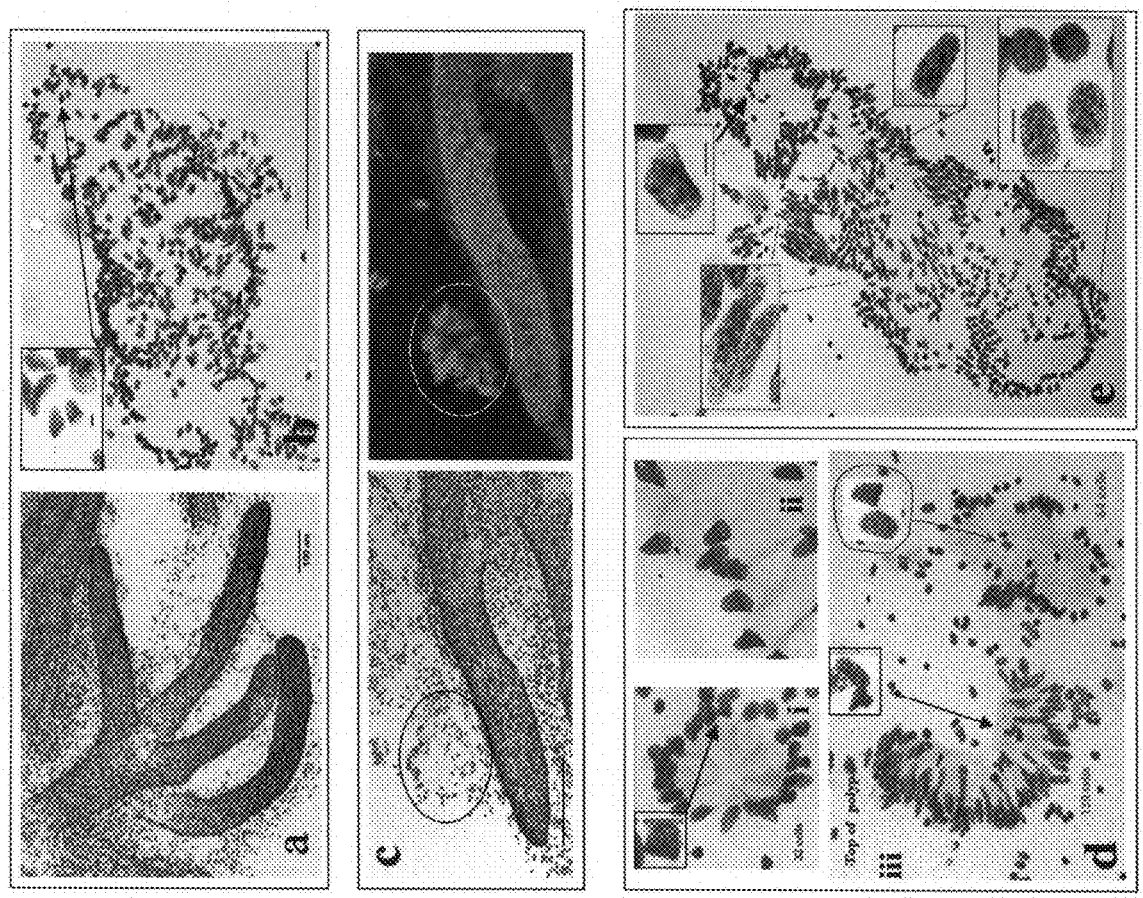
FIG. 13 shows adenomas. (a) Characteristic large branching crypt of adenomas. (b) An irregular crypt-like structure found throughout adenomas. Typically two, but sometimes 1, 4 or even 8, bell-shaped nuclei (insert) appear at the base of these large (>4000 cell) irregular crypt-like structures. (c) A cluster of cells of similar nuclear morphotype containing one bell-shaped nucleus. These forms of clusters contain exactly 16, 32, 64, and 128 total cells. Left panel, Feulgen-Giemsa stain. Right panel, phase contrast autofluorescent image. (d) Contexts in which bell-shaped nuclei appear in adenomas: (i) Cluster with 31 ovoid nuclei and one bell-shaped nucleus, (ii) Multiple bell-shaped nuclei in shoulder to shoulder arrangement, (iii) Bell-shaped nuclei arranged in a side-by-side pattern (arrow) (iii) Irregular mixture of ~250 nuclei of with several bell-shaped nuclei suggestive of nascent crypt bases. (e) Irregular crypt-like structure containing apparently clonal patches of cells of 5 different nuclear morphotypes with one bell-shaped nucleus [arrow] at the base. Scale bars, 100 μm (in 'a,b') and 5 μm (in 'e').
Figure 14:
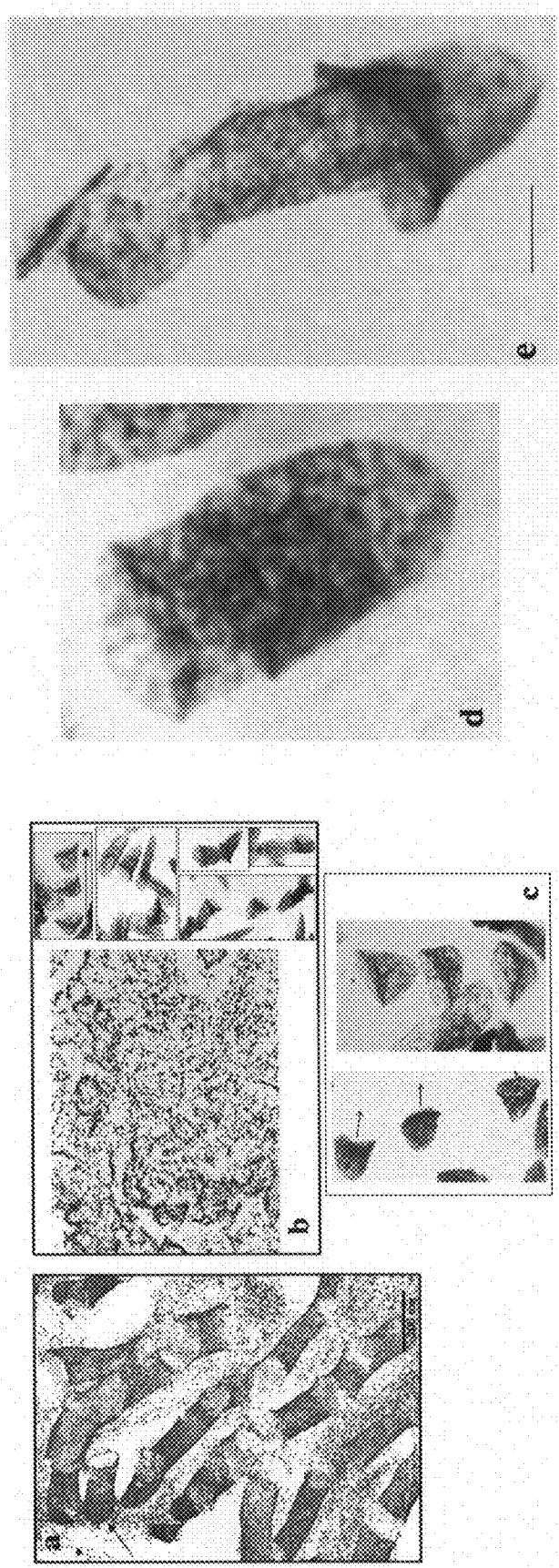
FIG. 14 shows adenocarcinomas. (a) Very large crypt-like structures (>8000 cells), with branches with frequent break points. The arrow indicates an example of an ~250 cell crypt-like structure found primarily near the surface of the tumor. (b) Interior tumor mass with multiple where multiple bell-shaped nuclei (2 □ $10^{-3}$ of all nuclear morphotypes). (c) Bell shaped nuclei in (b) oriented in head-to-toe syncytial and non-syncytial side-by-side configurations. (d) Symmetrical nuclear fission in adenocarcinoma. (e) Asymmetrical nuclear fission of a bell creating a cigar-shaped nucleus in adenocarcinoma. Similar structures have been observed in colonic metastases to the liver. Scale bar, 5 um.
Figure 15:
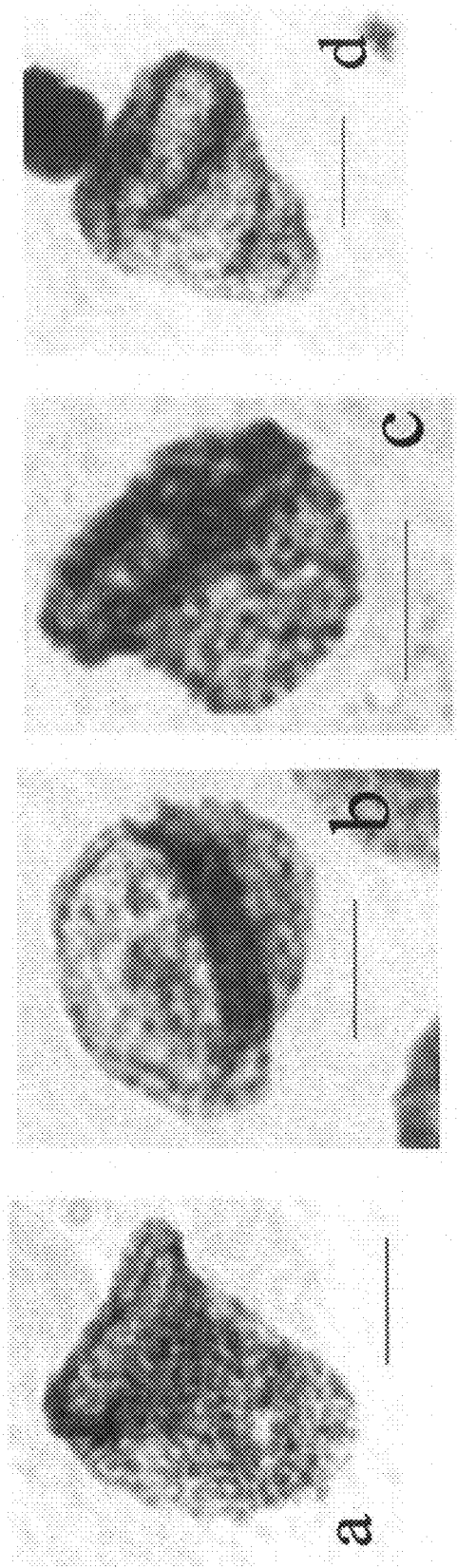
FIG. 15 shows morphological similarity of bell-shaped nuclei (Feulgen DNA stained in purple) as revealed in human tissues of: (a) embryonic gut, (b), colonic adenocarcinoma, (c) liver metastasis of colonic tumor, (d) pancreatic tumor. Condensed chromatin streak seen in lower half of bell in 'd' is seen in all bell-shaped nuclei from pancreatic but not at all in colonic tumors. Bar scale, 5 microns.
Figure 16:
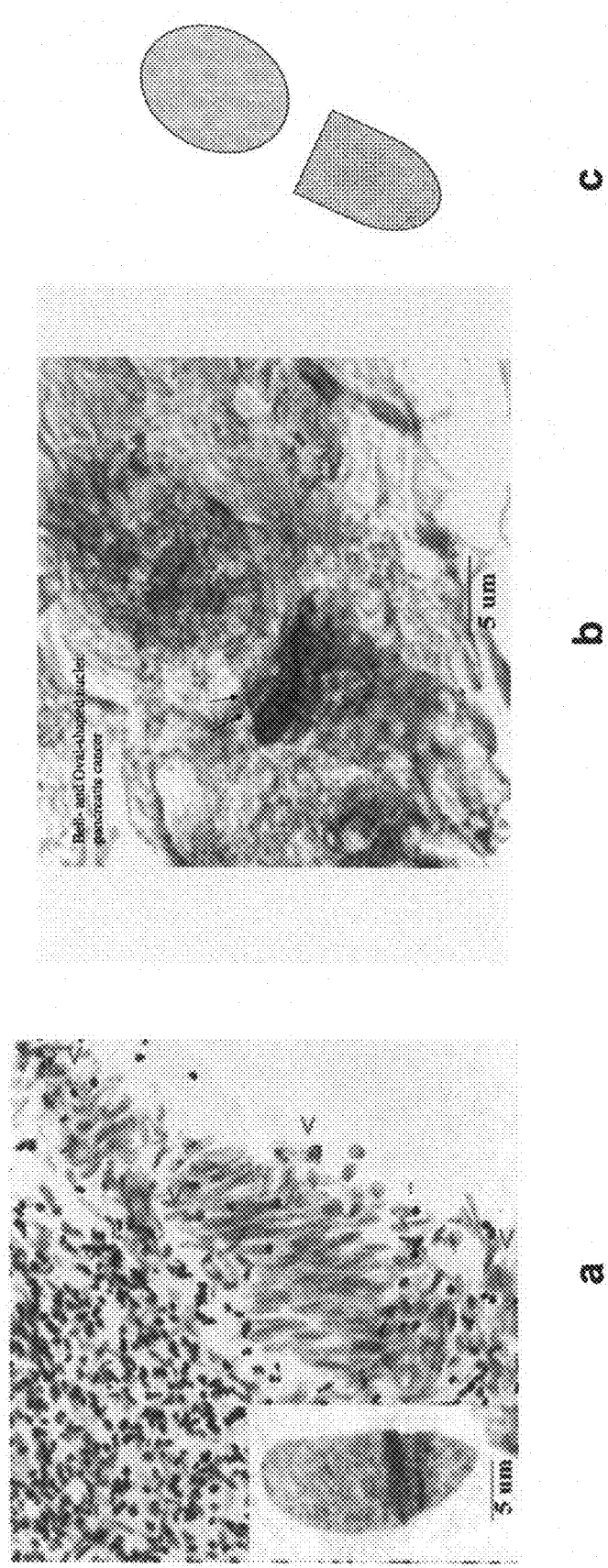
FIG. 16 shows bell-shaped nuclei detected readily by the histological procedure disclosed herein (Feulgen stain) and rarely (only example as yet) by standard histological procedures creating microtome sections of 5 microns sections (hematoxylin and eosin stain (H&E)). Same tumor, fixation within 30 minutes of resection.: (a) The bell-shaped nuclei giving rise to cigar-shaped nuclei (×100 magnification image to the left) present as a colony at the edge of a pancreatic tumor containing a number of asymmetrically dividing cells (arrowheads). (b) The single example found to date of bell- and oval-shaped nuclei visible on a standard tissue section slide in juxtaposition suggesting a recent asymmetrical nuclear division. The bell-shaped nucleus appears to have chromatin strands still attaching it to the oval nucleus (arrows). (c) Cartoon of the original picture showing this interpretation.
Figure 17:
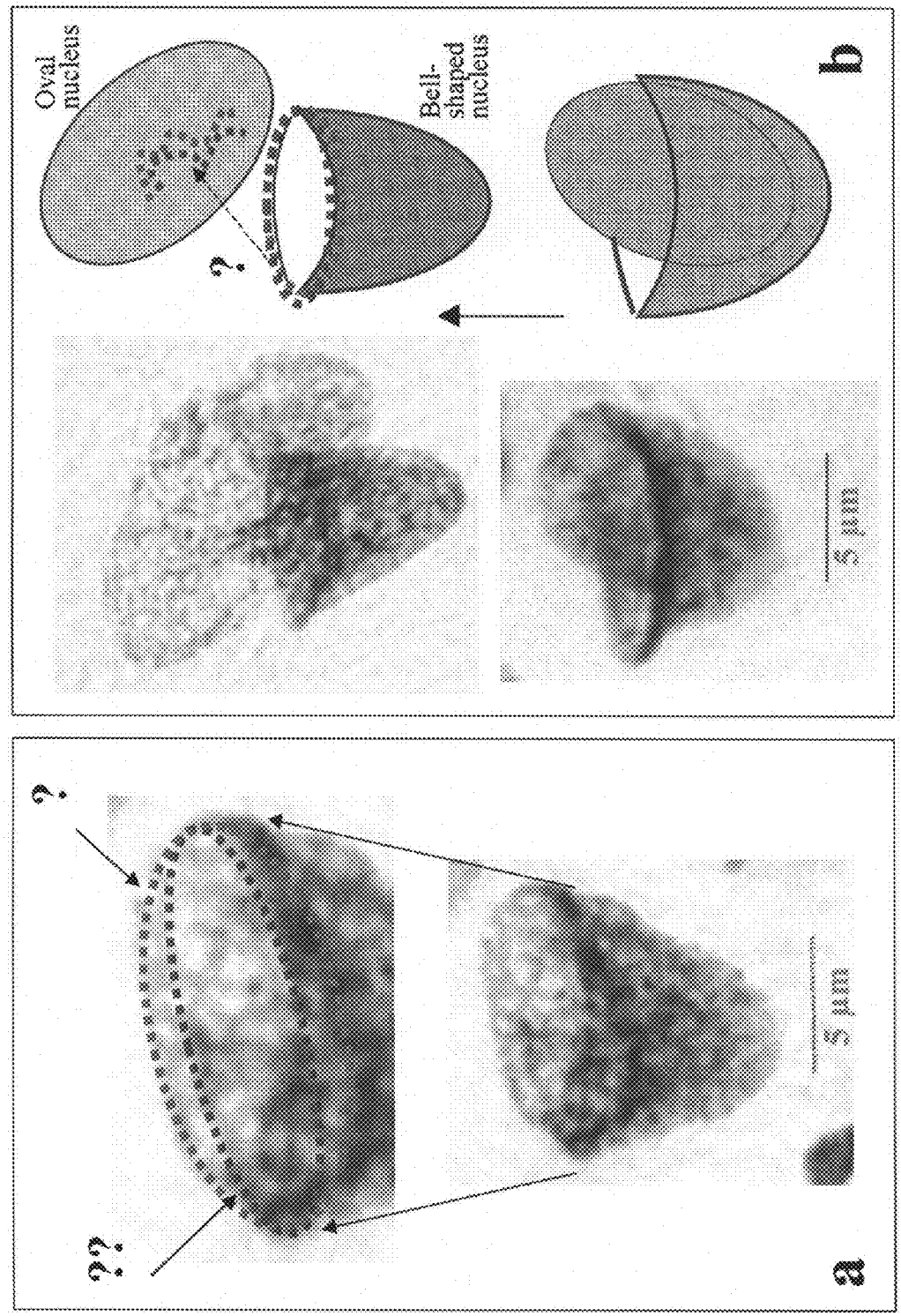
FIG. 17 is an illustration of a 'target of interest' in application of FISH to explore non-dividing and dividing bell-shaped nuclei in tumors: (a) Chromatin, stained darker because of higher concentration of DNA per square micron in the nuclear, creates the unique structure as a part of bell-shaped morphology, resembling prophase chromosomes arranged as two parallel circles. These circles put into drawing (above) illustrate the prediction of that specific chromosomes might be found at this specific site of bell-shaped nuclei in colon tumors, (b) Chromatin distribution and specific chromosome positioning changes as imaginary transformation (bell-to-oval shaped nuclei here) taking place throughout asymmetrical division of the bell-shaped nuclei.
Figure 18:
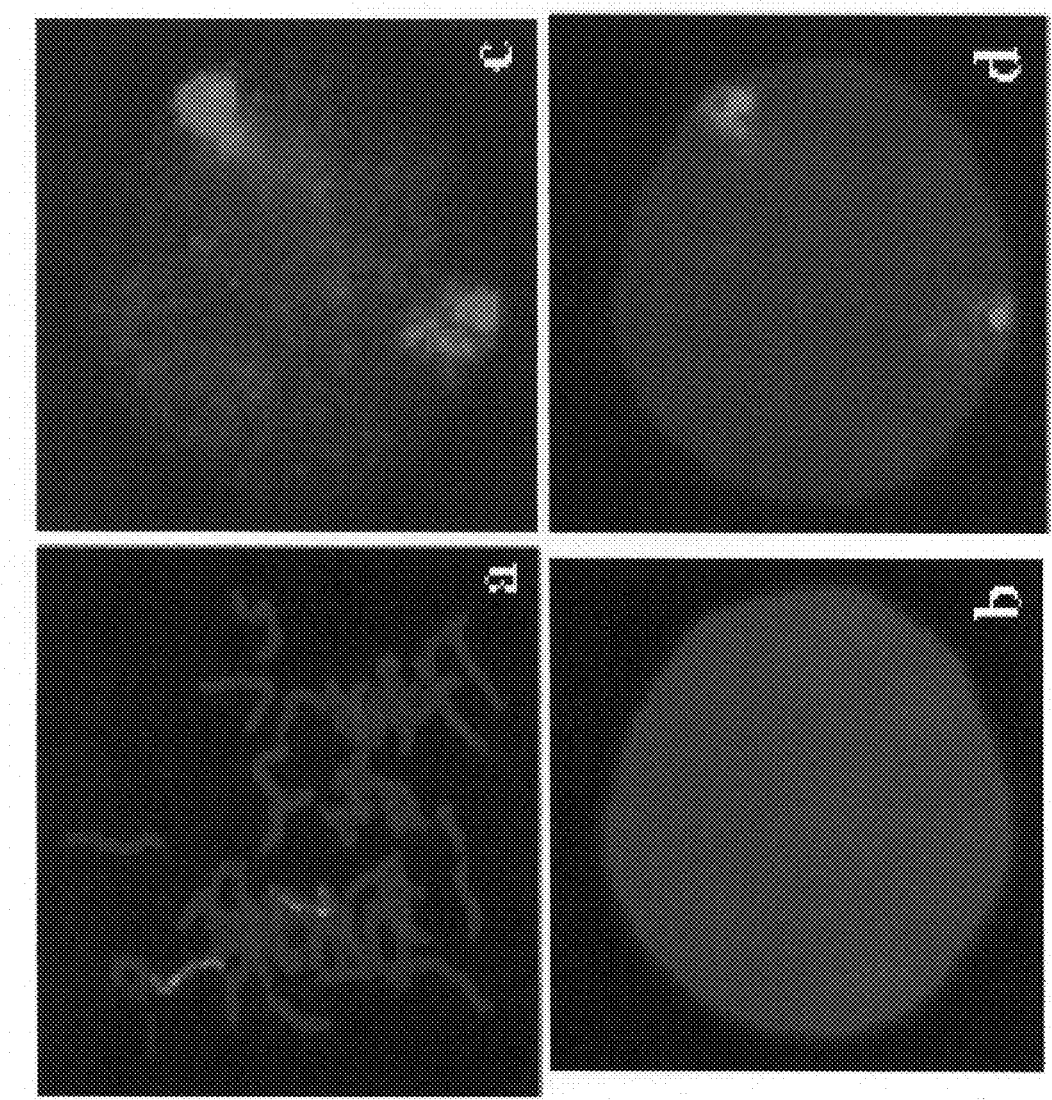
FIG. 18 shows the results of fluorescent in situ hybridization of chromosome 11 in spherical nuclei of TK-6 human cells. (a) two pairs of chromosomes in prophase chromosome spreads, (b) spherical nuclei DAPI nuclear stain, (c) same chromosome pair hybridized with FITC fluorescence probe, (d) merged image of DAPI and FITC interphase chromosomes stain.
Figure 19:
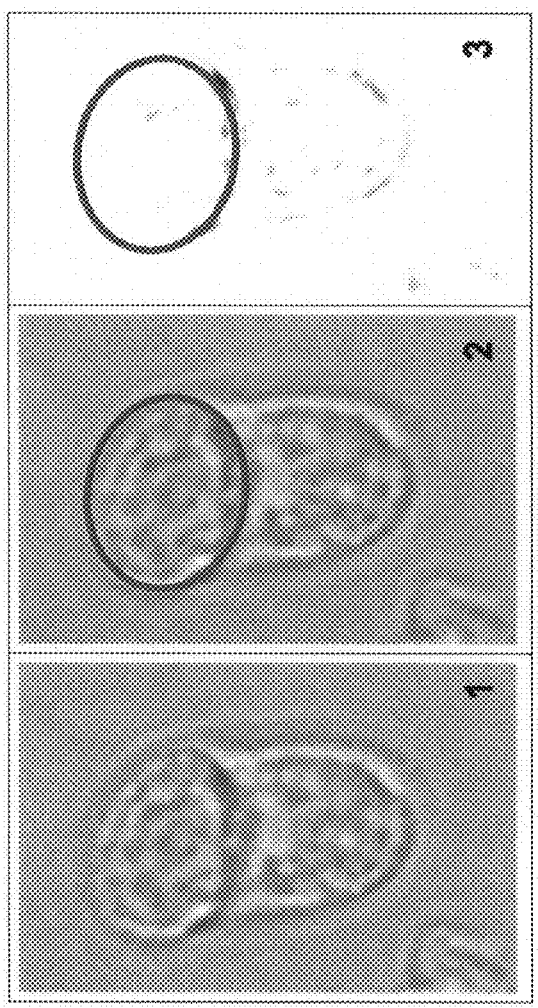
FIG. 19 shows bell-shaped nuclei as 'targets' in collection by laser pressure catapulting system ("laser pressure microdissection"): (a) The microscopic slide with cell spreads positioned in front of pulsed UV A laser that is coupled to a microscope. (b) Single nuclei can be seen through a microscope as shown for the cells spread of colon tumor tissue with bell-shaped nuclei in vision; (c) Same nuclei with recognizable morphology of the bell in non-stained slides (parts 1-3).
Figure 19:
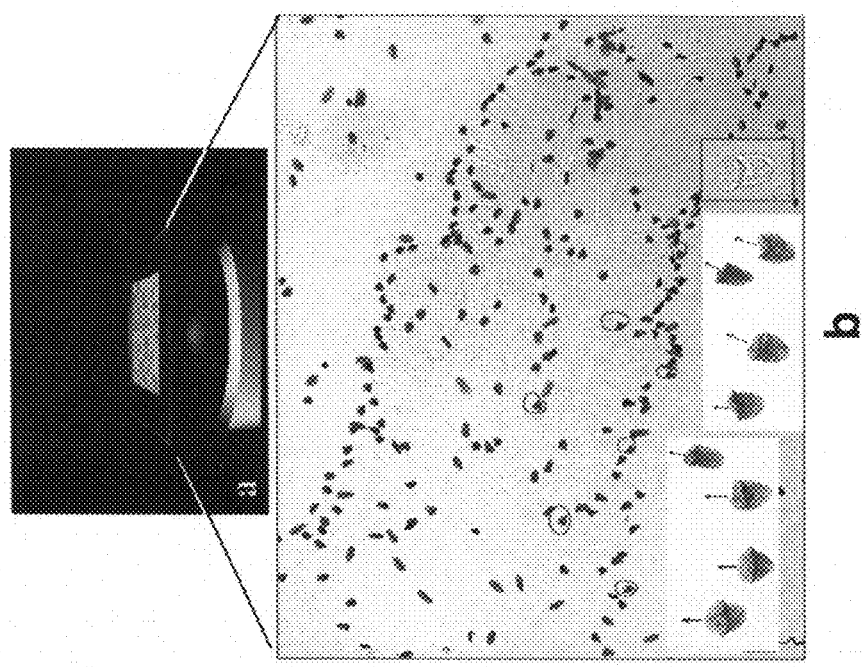

An array of distinct closed nuclear forms has been found in fetal hindgut, colonic adenomas and adenocarcinomas that appear to arise ab initio from asymmetrical nuclear fission from bell-shaped nuclei but subsequently divide by mitosis and die by apoptosis. The shared set of nuclear forms in fetuses and tumors that are absent in adult tissue support the $19^{th}$ century hypothesis that tumors were "embryonic" growths in adult organs (FIG. 9). These findings coupled with computer based image analysis and laser-assisted micro-dissection make the recognition and collection of large numbers of cells with specific nuclear morphologies possible. The characterization of the arrays of molecular and biochemical constituents in cells with bell-shaped nuclei as well as cells of other nuclear morphotypes peculiar to tumors should provide a previously unexpected set of potential therapeutic targets.

Oncogenesis like ontogenesis appears to proceed by lineal descent through an expanding set of stem cells. Only a small fraction of cells from a human tumor have the capacity to form new tumors as xenografts in immuno-suppressed rodents. Limiting dilution xenograft experiments have shown that the putative tumorigenic cells displayed stem cell-like properties in that they were capable of generating new tumors containing additional stem cells as well as regenerating the phenotypically mixed populations of cells present in the original tumor (Singh, S. et al., 2004. Oncogene, 23:7267-7273; Clarke, M., 2005. Biol. Blood Marrow Transplant., 11: 14-26).

Nearly all forms of late onset cancer pass through an extended period of preneoplasia and these preneoplastic colonies are monoclonal resulting from more than one rare genetic mutation from the germinal DNA. By the beginning of 21st century, direct attempts to enrich tumor cell populations with stem cells for transplant/dilution experiments had demonstrated that not only were tissue stem cells the likely cells of origin of preneoplasia but tumors themselves contained stem cells (Pardal, R. et al., 2003. Nature Rev., 3:895-902). Modern restatement of the hypothesis that tumors are in fact reasonably well organized heterogeneous fetal structures has been reviewed and extended (Sell, S., 2004. Crit. Rev. Oncol. Hematol., 51:1-28). 'Carcinoembryonic' stem cells would be expected to increase in number and give rise to differentiated cell types populating the highly heterogeneous niches within the tumor mass.

Various antigenic markers employed throughout the stem cell field have been used to enrich for cells capable of regenerating tissues or tumors often to a high degree, but no cells within these enriched populations have demonstrated any microscopic morphological cellular property that marks them as stem cells. If it is true that tumors arise from a single stem cell, a means is required to identify them and to collect them as homogeneous population of stem cells sufficient for analysis of molecular and biochemical analytes.

One method to achieve this goal relies on laser capture microdissection (LCM) to select and collect the tens of thousands of cells necessary for macromolecular array analyses and homogeneous with regard to microhistological properties that identify tumor stem cells. Alternately, dispersed cells with stem cell-associated surface markers of tumors have been enriched by flow cytometry and cell sorting from heterogeneous cell populations (Morrison, S. et al., 1999. *Cell*, 96:737-749; Suzuki, A. et al., 2004. *Diabetes*, 53:2143-2152).

The primary targets of existing methods of cancer therapeutics are cells transiting the cell cycle (Gomez-Vidal, J. et al., 2004. *Curr. Top. Med. Chem.*, 4:175-202; Fischer, P. and Gianella-Borradori, A., 2005. *Expert Opin. Investig. Drugs*, 14:457-477). No distinction is made between cells in transit between adult maintenance stem cells that divide to provide transition cells to replace the loss of terminal cells lost by programmed cell death and tumor stem cells. Therapy aims at the narrow window of regimens that kill all tumor stem cells without killing the patient, but adult maintenance stem cells would logically be expected to have the property of zero net cell growth while tumor stem cells, like fetal stem cells, are by definition involved in rapid net cell growth. Adult maintenance stem cell divisions would seem per force to be asymmetrical in nature giving rise to a new maintenance stem cell and a first differentiated transition cell. Tumor stem cells would require successive symmetrical nuclear divisions to support net tumor growth. It is in the discovery of bell-shaped nuclei undergoing symmetrical 'cup-from-cup' nuclear division in tumors that a specific target for cytostatic or cytocidal therapies has been identified.

One theory lending support to this is the theory that tumors could by asphyxiated by preventing angiogenesis (Folkman, J. and Ingber, D., 1992. *Sem. Cancer Biol.*, 3:88-96). Creating hypoxia may recreate the conditions of early embryogenesis so far as tumor stem cells are concerned and may explain the palliative but not curative effects of anti-angiogenic tactics. Blocking differentiation in tumors may block differentiation in normal tissues with undesirable consequences. Understanding that current cancer therapies are only minimally effective because the stem cells can repopulate tumors in a short period of time has become a powerful stimulus to the search for molecular and biochemical characteristics peculiar to tumor stem cells as opposed to adult maintenance stem cells. Such molecular and/or biochemical characteristics of tumor stem cells serve as targets in cancer therapeutics.

A key aspect of testing such theories and characterizing (molecular and biochemical properties) neoplastic stem cells and other neoplastic cell types is their isolation in sufficient numbers and degree of purity to permit quantitative chemical and biochemical analyses. Several means can be employed to obtain such cellular isolates. Laser capture microdissection, for example, is a method known in the art that allows one of skill in the art to manually select and microdissect batches of 10,000 bell-shaped nuclei from undifferentiated niches of colonic and pancreatic tumors. Cells 'catapulted' into the receiving vial are spread on microscope slides and scored as "bell", "not-bell" or "indeterminate" on the basis of morphology. When a reasonable level of enrichment is reached (>75% of isolated nuclei scored as "bell"), the procedure is varied to preserve mRNA, proteins etc. for further analyses.

Existing protocols to isolate live colonic epithelium cells isolation have been adapted for continued observations in cell culture that preserve their structural and functional characteristics (Stich, M. et al., 2003. *Pathol. Res. Pract.*, 199:405-409; Micke, P. et al., 2004. *J. Pathol.*, 202:130-138). Isolated cells or syncytia with bell-shaped nuclei can be placed in slowly-stirred microcarrier flasks with varying oxygen concentrations to mimic the oxygen levels expected in early embryos and unvascularized tumor niches. Medium replete with glutamine but lower in glucose than "standard" cell culture media formulations is also used to encourage growth of cells and syncytia with these bell-shaped nuclei so they can be studied under controlled laboratory conditions. Application of these methodologies is reasonably expected to yield a homogeneous cellular preparation with regard to nuclear morphology, mode of division and/or presence in special forms of multicellular aggregates or syncytia. These cells can also be isolated in a manner such that they can be propagated and studied in cell or tissue culture.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying one or more candidate anti-tumorigenic agents comprising:
    a) treating a mammal having a tumor with one or more candidate agents;
    b) determining the nuclear morphology of cells contained within a tumor sample obtained from the mammal; and
    c) comparing the nuclear morphology of the cells within the tumor sample obtained from the mammal treated with the one or more candidate agents with cells within a tumor sample obtained from a mammal having a tumor but not treated with the one or more candidate agents, wherein elimination of, or a decrease in the number of, stem cells comprising bell-shaped nuclei within the tumor sample obtained from the mammal treated with the one or more candidate agents is indicative of the effectiveness of the one or more candidate agents as an anti-tumorigenic agent.

2. The method of claim 1, wherein the mammal is a human.

3. The method of claim 1, wherein the mammal is a rat or mouse.

4. The method of claim 1, wherein the tumor in the mammal arises de novo.

5. The method of claim 1, wherein the tumor in the mammal is a xenotransplant.

6. The method of claim 5, wherein the xenotransplant is from a human tumor.

7. A method of identifying one or more candidate anti-tumorigenic agents comprising:
    a) treating a mammal having a tumor with one or more candidate agents;
    b) determining the nuclear morphology of multi-nuclear syncytia comprising one or more bell-shaped nuclei contained in a tumor sample obtained from the mammal; and
    c) comparing the nuclear morphology of the multi-nuclear syncytia in the tumor sample obtained from the mammal treated with the one or more candidate agents with multi-nuclear syncytia in a tumor sample obtained from a mammal having a tumor but not treated with the one or more candidate agents, wherein the elimination of, or a decrease in the number of, multi-nuclear syncytia comprising bell-shaped nuclei in the tumor sample obtained from the mammal treated with the one or more candidate agents is indicative of the effectiveness of the one or more candidate agents as an anti-tumorigenic agent.

8. A method of identifying one or more candidate anti-tumorigenic agents comprising treating a cultured tumor tissue or cell sample with one or more candidate agents and evaluating the nuclear morphology of cells contained in the sample, wherein the cells comprise heteromorphic nuclear morphotypes including stem cells comprising bell-shaped nuclei, wherein in the absence of an anti-tumorigenic agent, the cultured tumor cells maintain their heteromorphic nuclear morphotypes including bell-shaped nuclei, and wherein the elimination of, or a decrease in the number of stem cells comprising bell-shaped nuclei is indicative of the effectiveness of the one or more candidate agents as an anti-tumorigenic agent.

9. A method of identifying one or more candidate anti-tumorigenic agents comprising treating a cultured tumor tissue or cell sample with one or more candidate agents and evaluating the nuclear morphology of multi-nuclear syncytia comprising one or more bell-shaped nuclei contained in the sample, wherein in the absence of an anti-tumorigenic agent, the multi-nuclear syncytia maintain their bell-shaped nuclei and the elimination of, or a decrease in the number of, syncytia comprising bell-shaped nuclei is indicative of the effectiveness of the one or more candidate agents as an anti-tumorigenic agent.

10. A method of identifying one or more candidate agents that eliminate, or decrease the number of, stem cells comprising bell-shaped nuclei comprising:
   a) treating a cultured sample of cells having heteromorphic nuclear morphotypes including stem cells comprising bell-shaped nuclei with one or more candidate agents; and
   b) comparing the nuclear morphotype of the cells treated with the one or more candidate agents with the nuclear morphotype of control cells not treated with the one or more candidate agents, wherein elimination of, or a decrease in the number of, stem cells comprising bell-shaped nuclei is indicative of the effectiveness of the one or more candidate agents to eliminate, or decrease the number of, stem cells comprising bell-shaped nuclei.

11. The method of claim 10, wherein the cultured sample of cells are mammalian cells.

12. The method of claim 11, wherein the mammalian cells are human cells.

13. The method of claim 10, wherein the agent interferes with the division of stem cells comprising bell-shaped nuclei.

14. A method of identifying one or more candidate agents that eliminate, or decrease the number of, multi-nuclear syncytia comprising bell-shaped nuclei comprising:
   a) treating a cultured sample of cells comprising multi-nuclear syncytia comprising one or more bell-shaped nuclei with one or more candidate agents; and
   b) comparing the nuclear morphotype of the multi-nuclear syncytia treated with the one or more candidate agents with the nuclear morphotype of control multi-nuclear syncytia not treated with the one or more candidate agents, wherein elimination of, or a decrease in the number of, multi-nuclear syncytia comprising bell-shaped nuclei is indicative of the effectiveness of the one or more candidate agents to eliminate, or decrease the number of, multi-nuclear syncytia comprising bell-shaped nuclei.

* * * * *